United States Patent
Yen et al.

(10) Patent No.: US 11,038,124 B2
(45) Date of Patent: Jun. 15, 2021

(54) ORGANIC COMPOUND AND ORGANIC ELECTROLUMINESCENCE DEVICE USING THE SAME

(71) Applicants: Feng-Wen Yen, Taipei (TW); Li-Chieh Chuang, Nantou (TW)

(72) Inventors: Feng-Wen Yen, Taipei (TW); Li-Chieh Chuang, Nantou (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 316 days.

(21) Appl. No.: 16/150,287

(22) Filed: Oct. 3, 2018

(65) Prior Publication Data

US 2020/0111971 A1    Apr. 9, 2020

(51) Int. Cl.
*H01L 51/50* (2006.01)
*H01L 51/00* (2006.01)
*C07D 333/76* (2006.01)
*C07D 307/91* (2006.01)

(52) U.S. Cl.
CPC ........ *H01L 51/0073* (2013.01); *C07D 307/91* (2013.01); *C07D 333/76* (2013.01); *H01L 51/0058* (2013.01); *H01L 51/0074* (2013.01); *H01L 51/5012* (2013.01)

(58) Field of Classification Search
None
See application file for complete search history.

(56) References Cited

U.S. PATENT DOCUMENTS

| 9,947,879 B2 | 4/2018 | Ito et al. |
| 2016/0351817 A1 | 12/2016 | Kim et al. |
| 2018/0314376 A1* | 11/2018 | Chen ............ G06F 3/0416 |

FOREIGN PATENT DOCUMENTS

| KR | 2012072784 | * | 7/2012 | ............ H01L 50/51 |
| WO | 2013055132 A2 | | 4/2013 | |

* cited by examiner

*Primary Examiner* — Gregory D Clark

(57) ABSTRACT

The present invention discloses an organic compound and an organic electroluminescence device employing the organic compound as the fluorescent host material in the light emitting layer of the organic electroluminescence device. The organic electroluminescence device employing the organic compound of the present invention can operate under reduced driving voltage, increase current efficiency, and prolong half-life time.

10 Claims, 1 Drawing Sheet

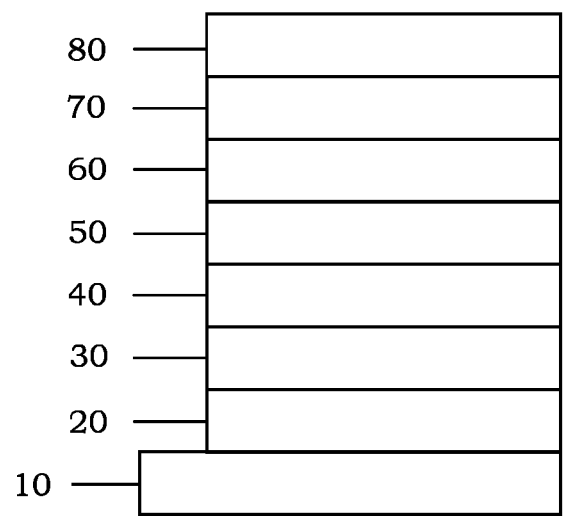

ORGANIC COMPOUND AND ORGANIC ELECTROLUMINESCENCE DEVICE USING THE SAME

FIELD OF INVENTION

The present invention relates to an organic compound and, more particularly, to an organic electroluminescence device using the organic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

Typically, the organic EL device is composed of organic material layers sandwiched between two electrodes. The organic material layers include, e.g., hole injection layer (HIL), hole transporting layer (HTL), emitting layer (EML), electron transporting layer (ETL), and electron injection layer (EIL). The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light out-coupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

For full-colored displays using organic EL devices, the organic materials used in the organic EL devices are still unsatisfactory in half-lifetime, driving voltage, and current efficiency. Therefore, there is still a need for an organic compound that can lower the driving voltage, increase the current efficiency, and prolong the half-life time for the organic EL device.

SUMMARY OF THE INVENTION

Accordingly, an object of the present invention is to provide an organic compound, which can be used as a fluorescent host material in the emitting layer of the organic EL device to improve the power consumption, current efficiency, and life time of the device.

Another object of the invention is to provide an organic compound and an organic EL device using the same, which can operate under reduced voltage and exhibit higher current efficiency and longer half-life time.

According to the present invention, an organic compound which can be used in organic EL devices is disclosed. The organic compound is represented by the following formula (A):

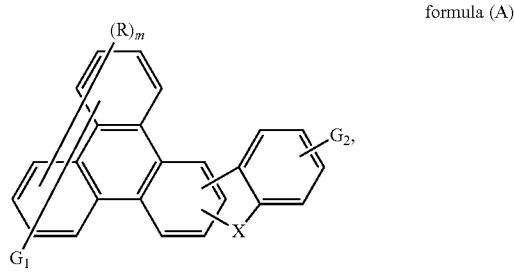

formula (A)

wherein at least one of $G_1$ and $G_2$ exists and represents formula (B) below:

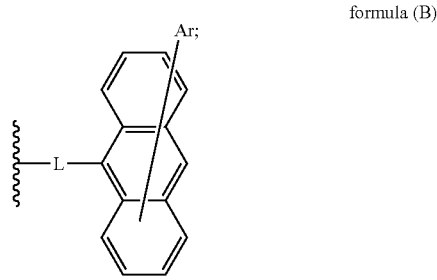

formula (B)

X is a divalent bridge selected from the group consisting of O and S; m is an integer of 0 to 8; L represents a single bond, a substituted or unsubstituted divalent arylene group having 6 to 30 ring carbon atoms, or a substituted or unsubstituted divalent heteroarylene group having 6 to 30 ring carbon atoms; Ar represents a halogen, a substituted or unsubstituted aryl group having 6 to 30 carbon atoms, or a substituted or unsubstituted heteroaryl group having 3 to 30 carbon atoms; and R represents a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms.

The present invention further discloses an organic electroluminescence device. The organic electroluminescence device comprises a pair of electrodes composed of a cathode and an anode, and a light emitting layer between the pair of electrodes. The light emitting layer comprises the organic compound of formula (A).

BRIEF DESCRIPTION OF THE DRAWINGS

The FIGURE is a schematic view showing an organic EL device according to an embodiment of the present invention.

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an organic compound which can be used as the fluorescent host material of the light emitting layer in the organic EL device is disclosed. The organic compound is represented by the following formula (A):

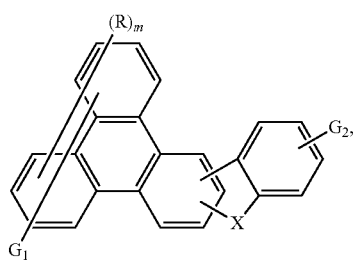

formula (A)

wherein at least one of $G_1$ and $G_2$ exists and represents formula (B) below:

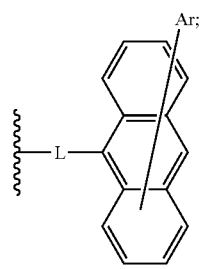

formula (B)

X is a divalent bridge selected from the group consisting of O and S; m is an integer of 0 to 8; L represents a single bond, a substituted or unsubstituted divalent arylene group having 6 to 30 ring carbon atoms, or a substituted or unsubstituted divalent heteroarylene group having 6 to 30 ring carbon atoms; Ar represents a halogen, a substituted or unsubstituted aryl group having 6 to 30 carbon atoms, or a substituted or unsubstituted heteroaryl group having 3 to 30 carbon atoms; and R represents a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms.

In some embodiments, the organic compound can be represented by one of the following formula (1) to formula (12):

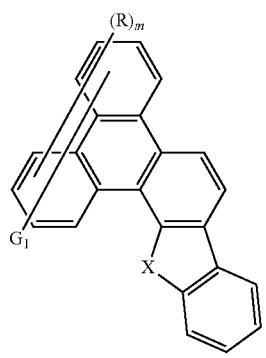

formula (1)

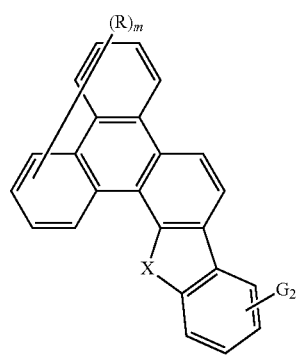

formula (2)

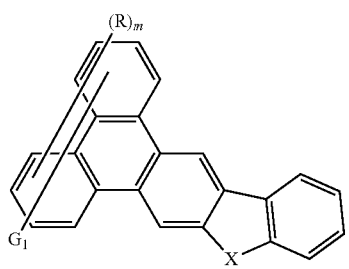

formula (3)

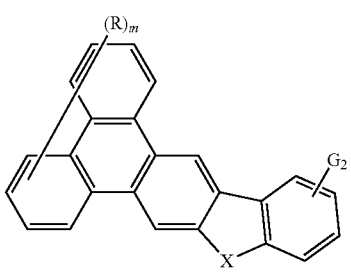

formula (4)

-continued formula (5)
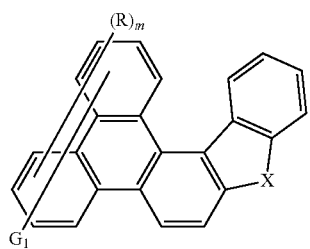

formula (6)
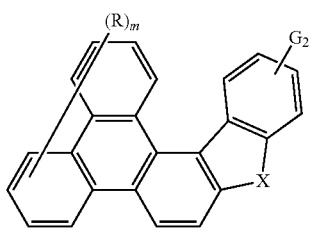

formula (7)
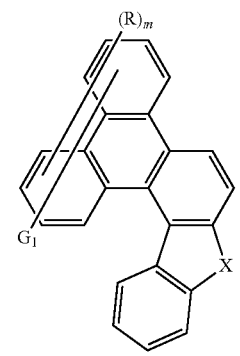

formula (8)
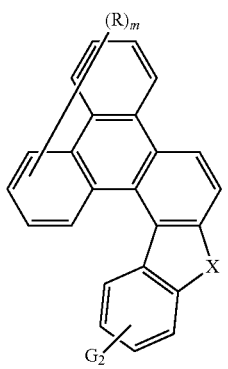

formula (9)
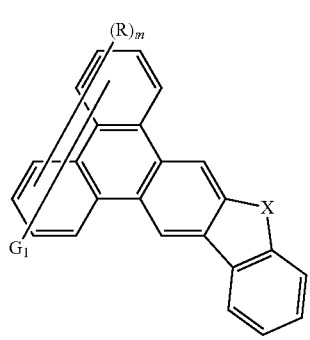

formula (10)
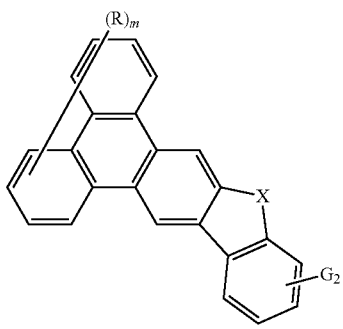

formula (11)
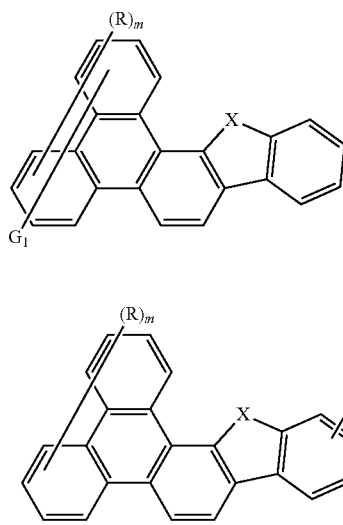

and formula (12)
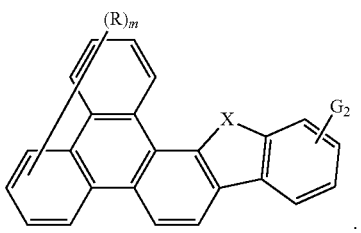

In some embodiments, the alkyl group, aralkyl group, aryl group, or heteroaryl group may be substituted by a halogen, an alkyl group, an aryl group, or a heteroaryl group.

In some embodiments, Ar may represent a substituted or unsubstituted phenyl group, a substituted or unsubstituted biphenyl group, a substituted or unsubstituted terphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, or a substituted or unsubstituted chrysenyl group.

In some embodiments, Ar may represent one of the following substituents:

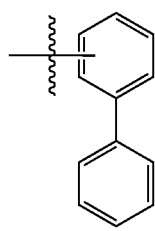

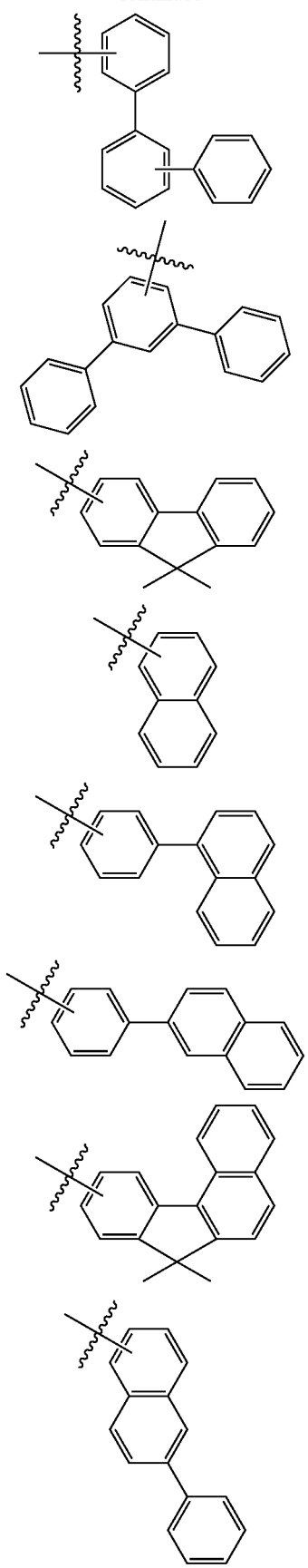
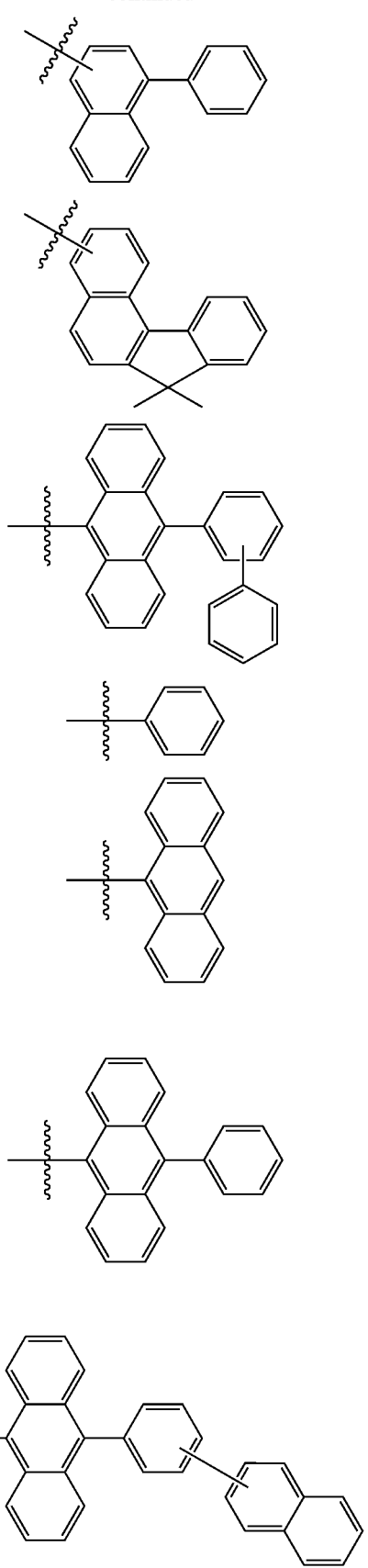

-continued
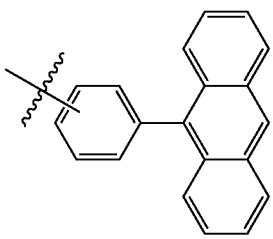
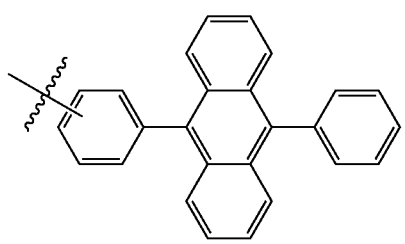
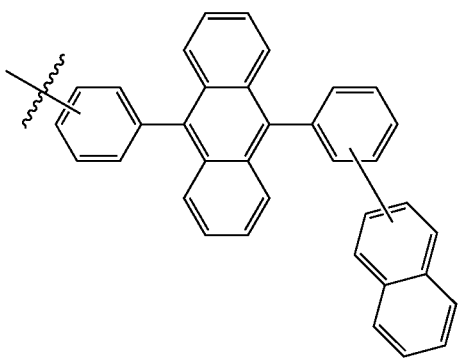
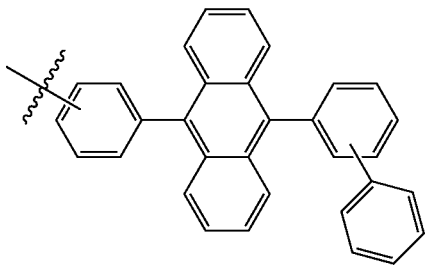
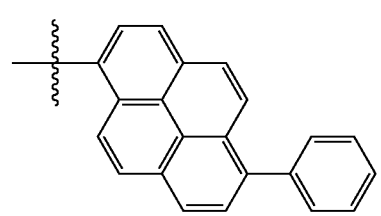
-continued
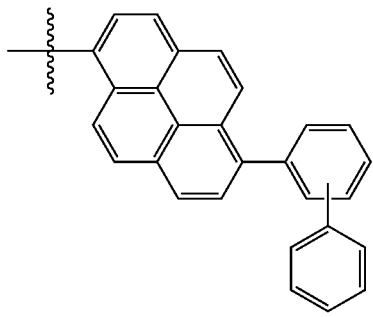
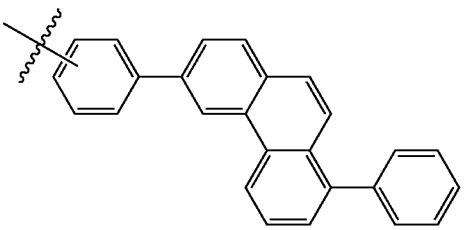
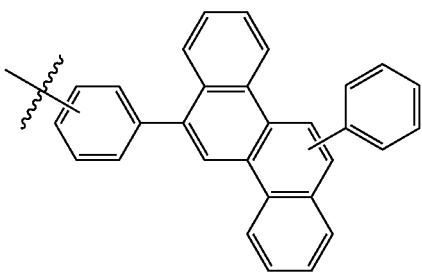
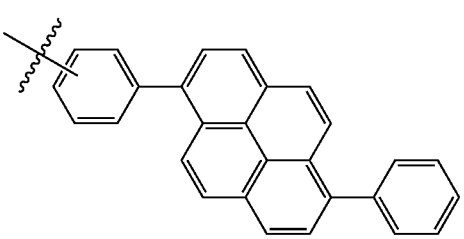
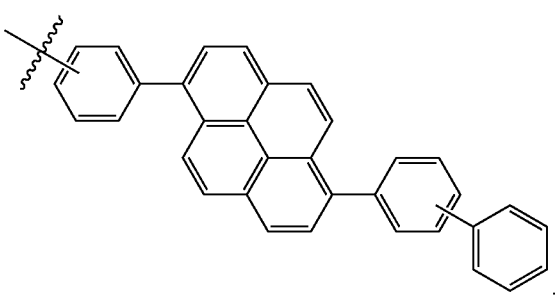
Preferably, the organic compound is one of the following compounds:

Compound 1
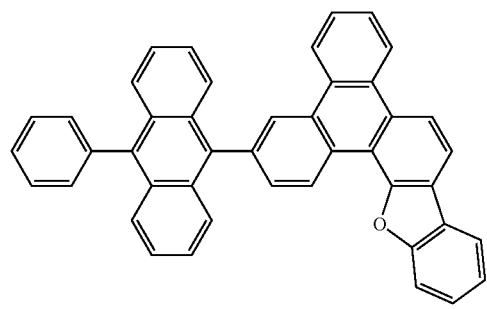
Compound 2
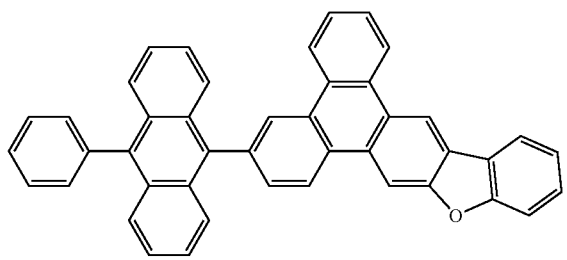
Compound 3
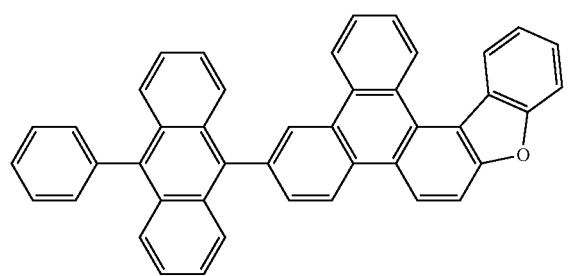
Compound 4
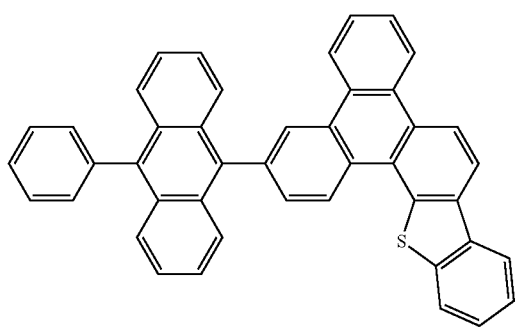
Compound 5
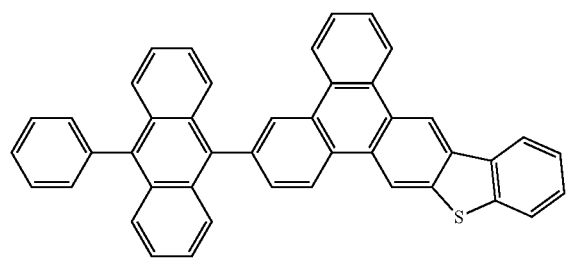
Compound 6
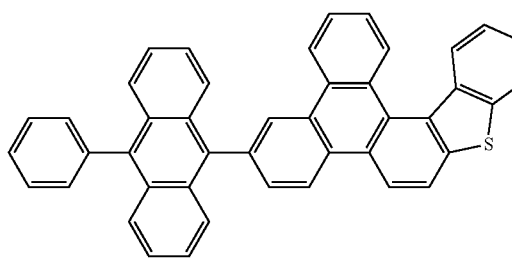
Compound 7
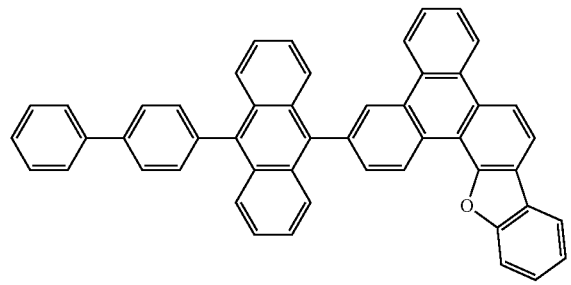
Compound 8
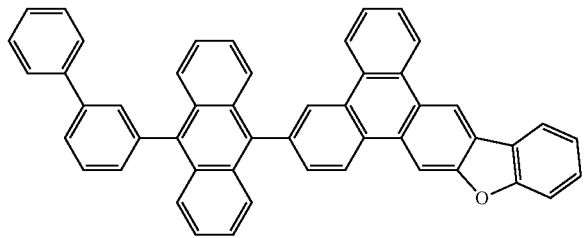
Compound 9
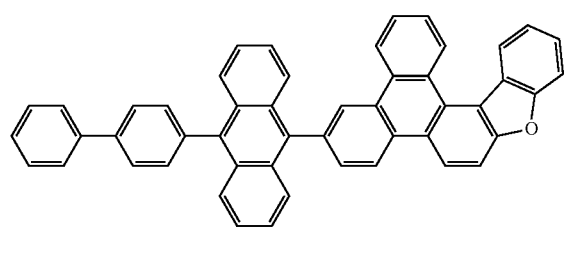
Compound 10
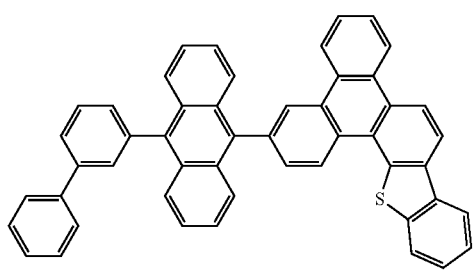

-continued
Compound 11
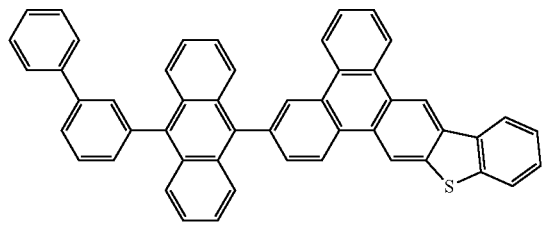
Compound 12
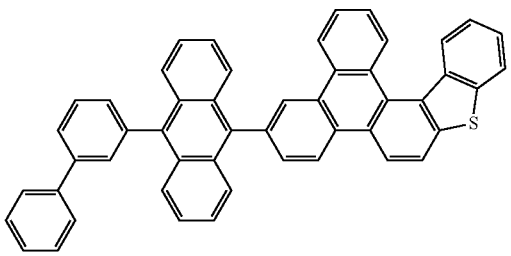
Compound 13
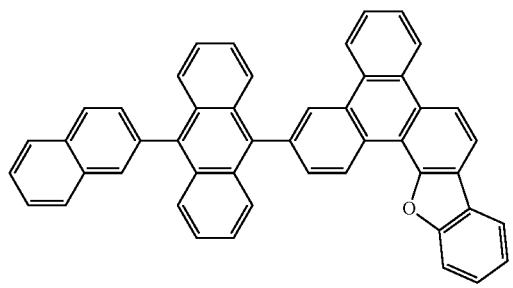
Compound 14
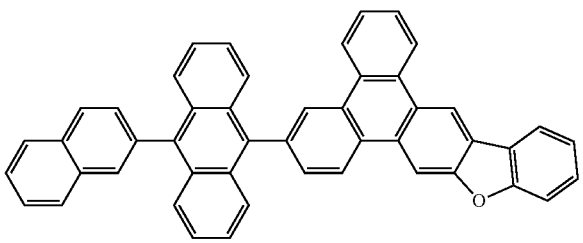
Compound 15
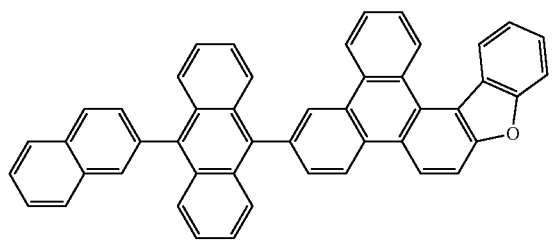
Compound 16
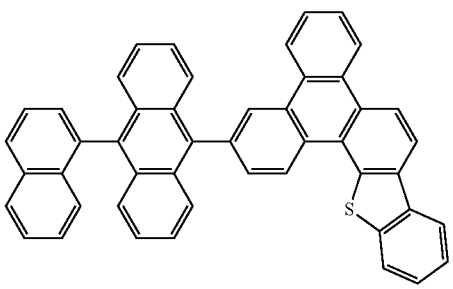
Compound 17
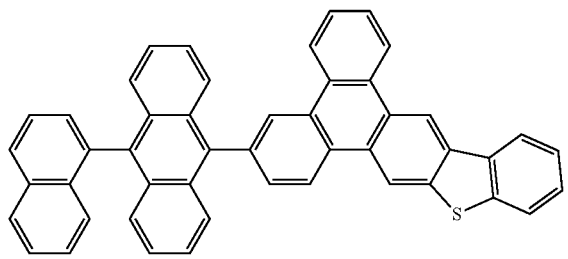
Compound 18
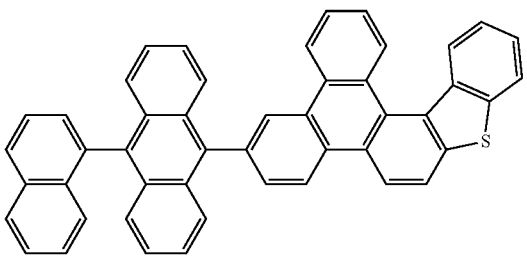
Compound 19
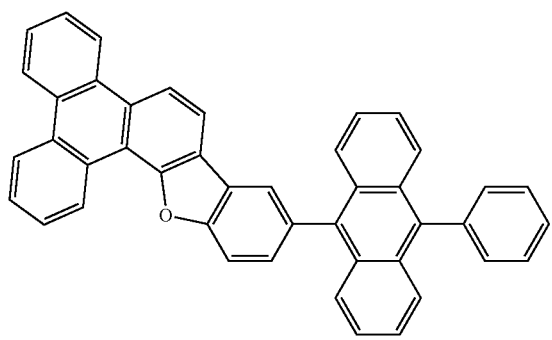
Compound 20
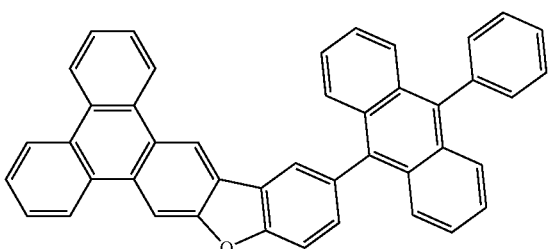

-continued
Compound 21
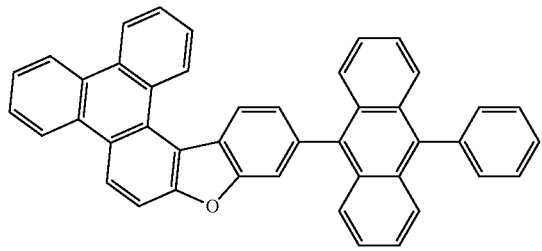 [SMILES: c1ccc(-c2c3ccccc3c(-c3ccc4c(c3)oc3ccc5c6ccccc6c6ccccc6c5c34)c3ccccc23)cc1]
Compound 22
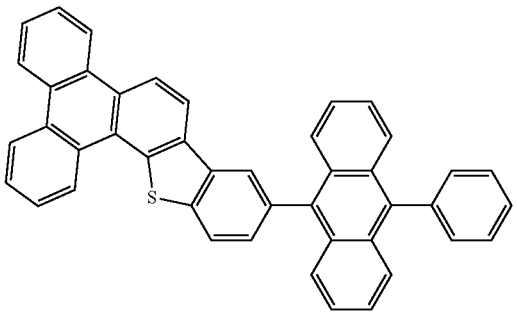 [SMILES: c1ccc(-c2c3ccccc3c(-c3ccc4sc5c(ccc6c7ccccc7c7ccccc7c65)c4c3)c3ccccc23)cc1]
Compound 23
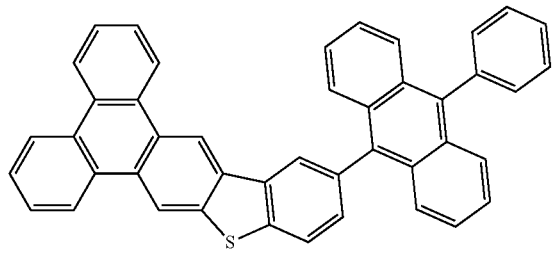
Compound 24
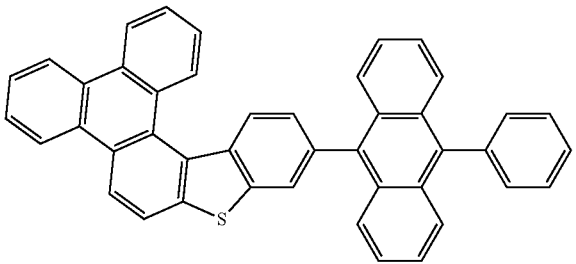
Compound 25
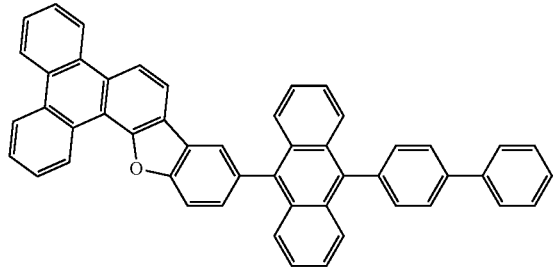
Compound 26
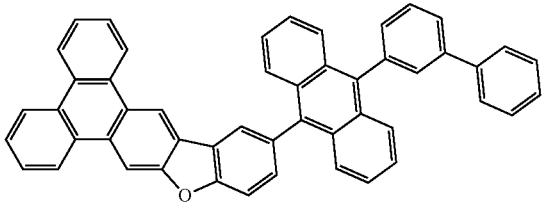
Compound 27
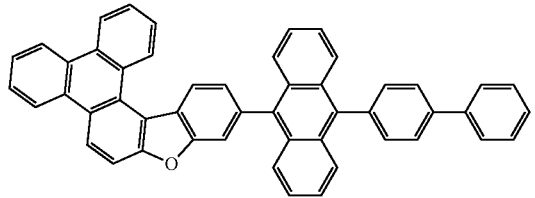
Compound 28
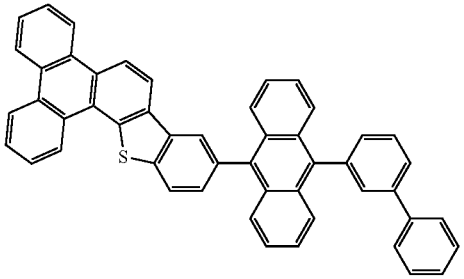
Compound 29
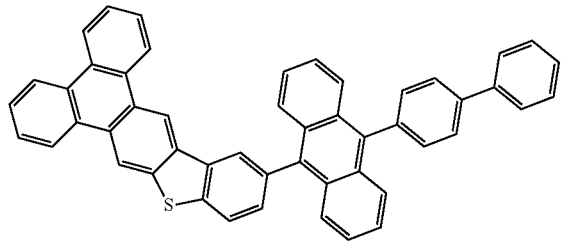
Compound 30
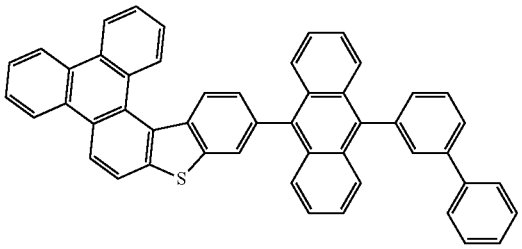

-continued
Compound 31
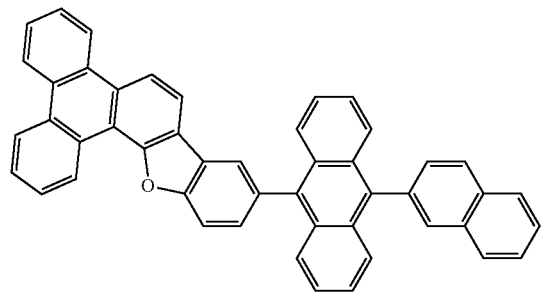
Compound 32
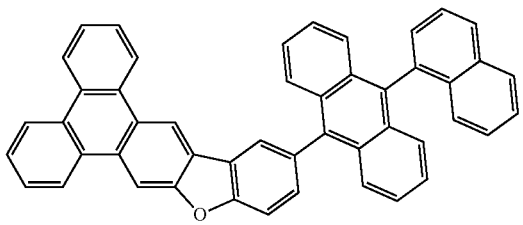
Compound 33
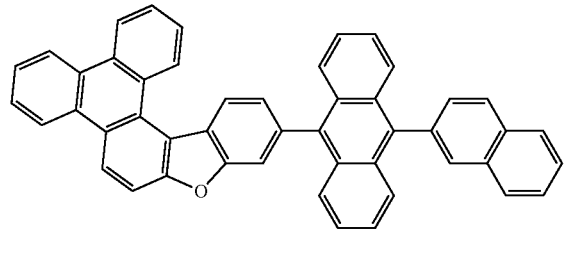
Compound 34
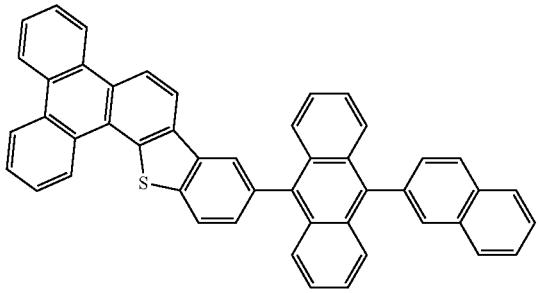 [SMILES: c1ccc2cc(-c3c4ccccc4c(-c4ccc5oc6c(ccc7c8ccccc8c8ccccc8c76)c5c4)c4ccccc34)ccc2c1]
Compound 35
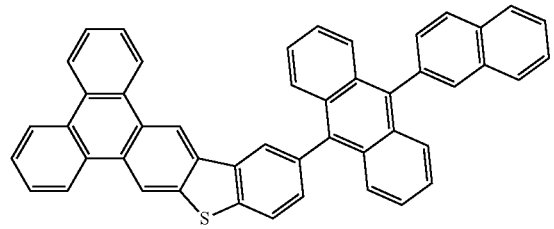 [SMILES: c1ccc2cc(-c3c4ccccc4c(-c4ccc5sc6cc7c8ccccc8c8ccccc8c7cc6c5c4)c4ccccc34)ccc2c1]
Compound 36
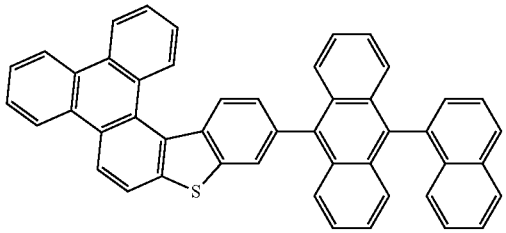
Compound 37
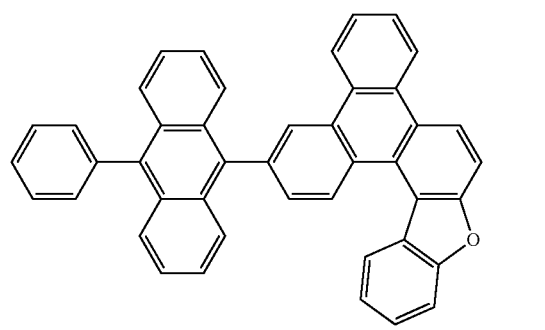
Compound 38
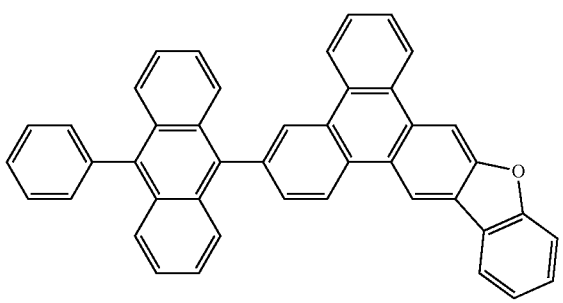
Compound 39
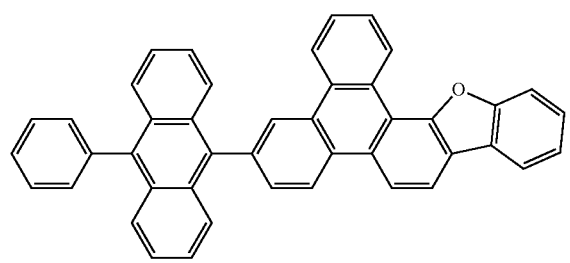
Compound 40
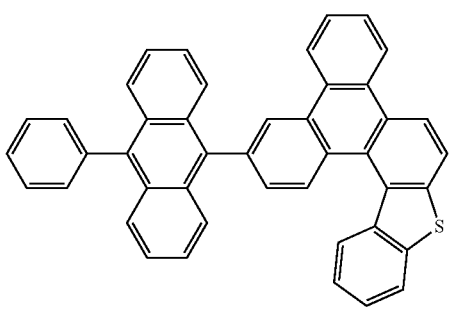

Compound 41
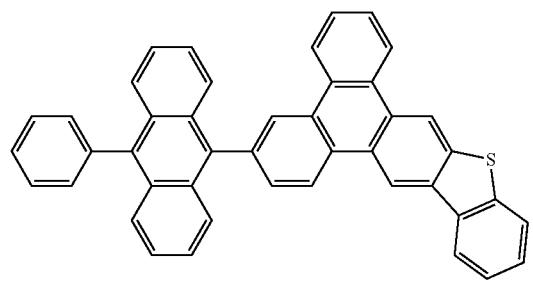
Compound 42
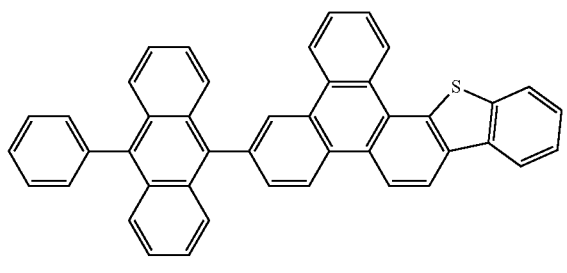
Compound 43
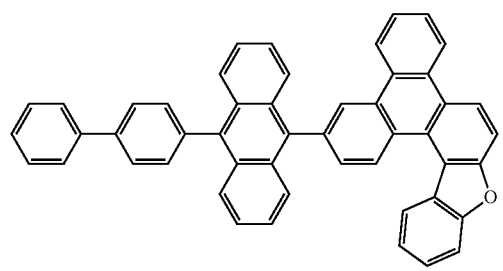
Compound 44
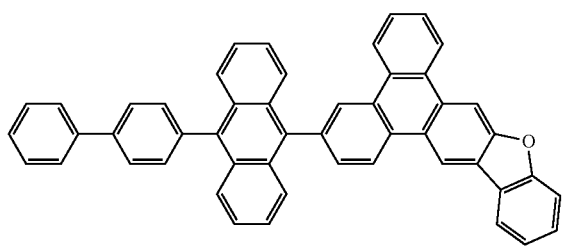
Compound 45
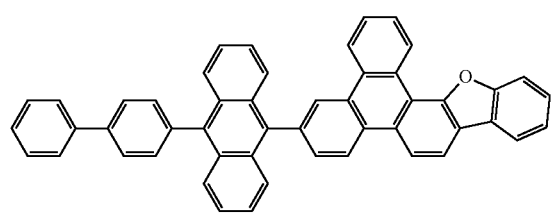
Compound 46
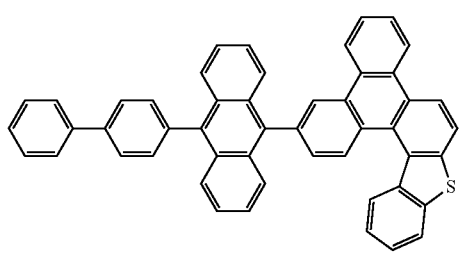
Compound 47
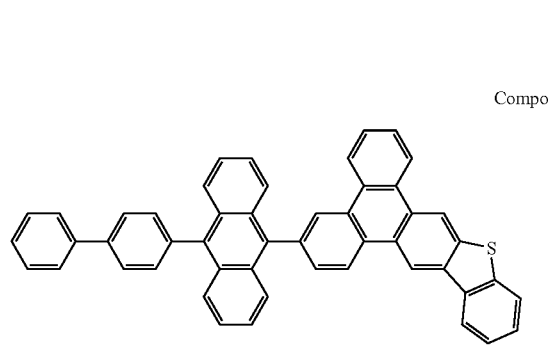
Compound 48
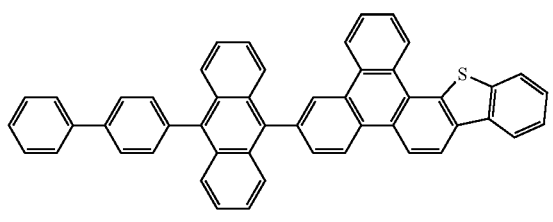
Compound 49
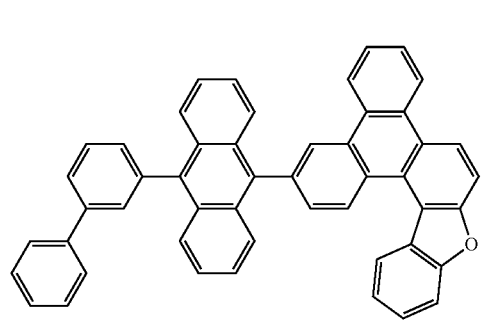
Compound 50
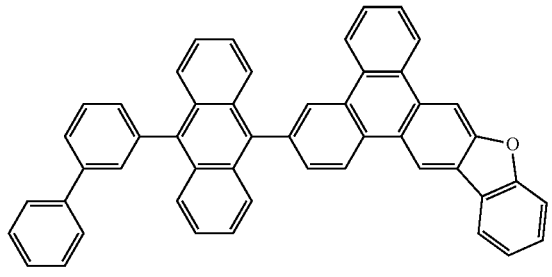

-continued
Compound 51
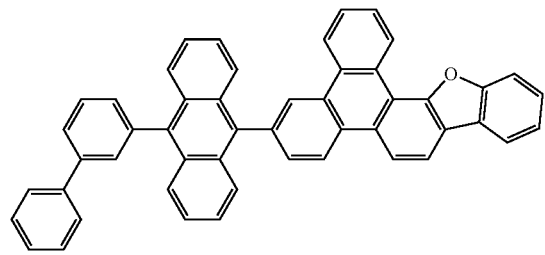
Compound 52
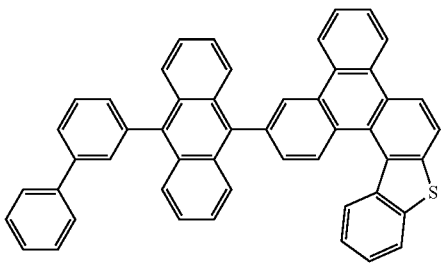
Compound 53
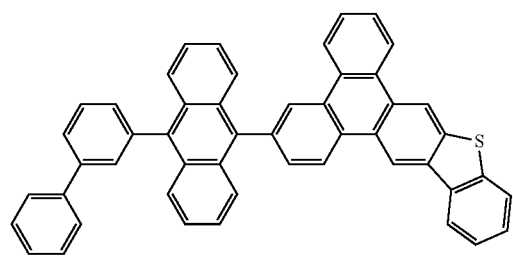
Compound 54
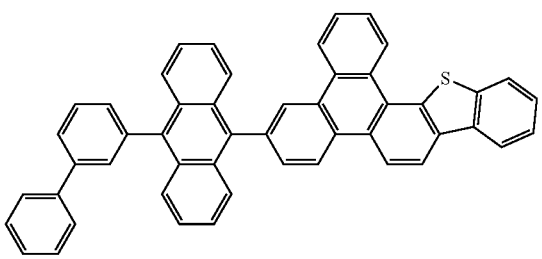
Compound 55
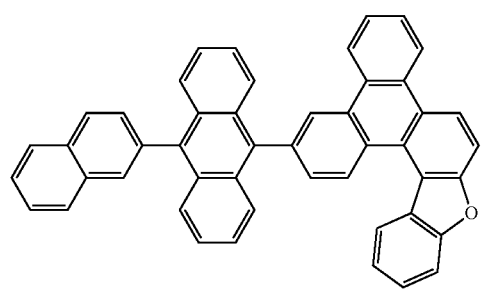
Compound 56
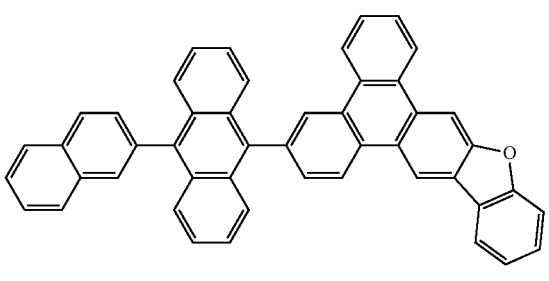
Compound 57
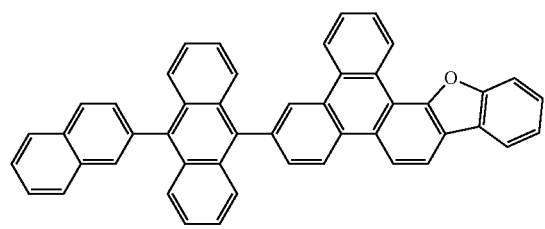
Compound 58
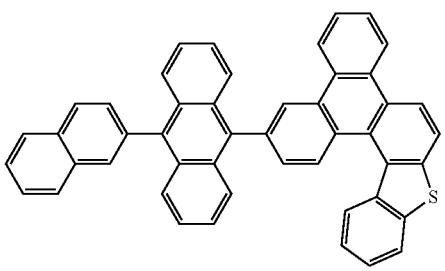
Compound 59
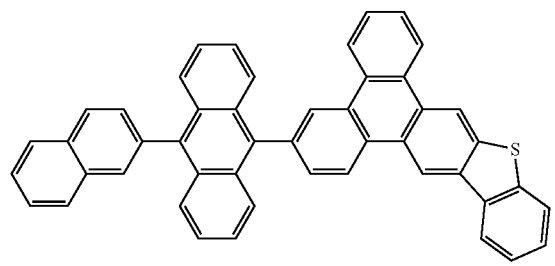
Compound 60

-continued
Compound 61
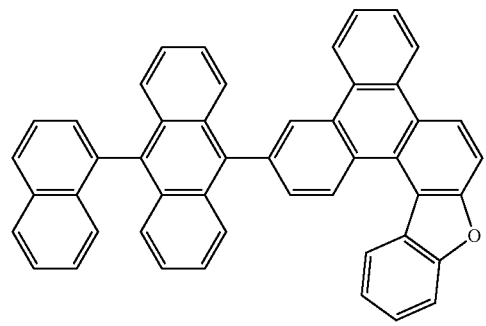
Compound 62
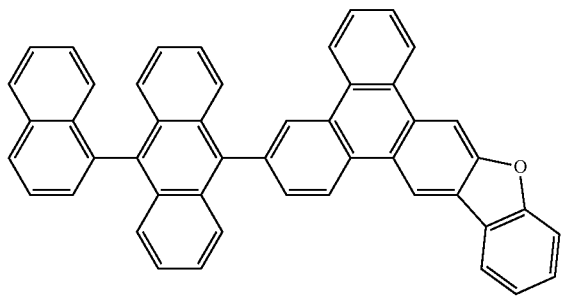
Compound 63
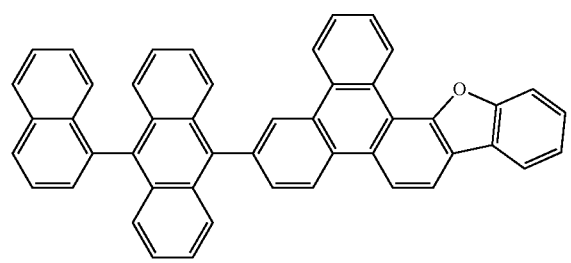
Compound 64
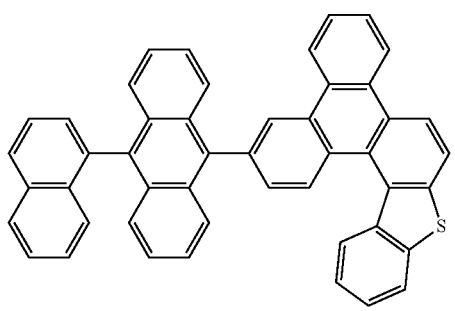
Compound 65
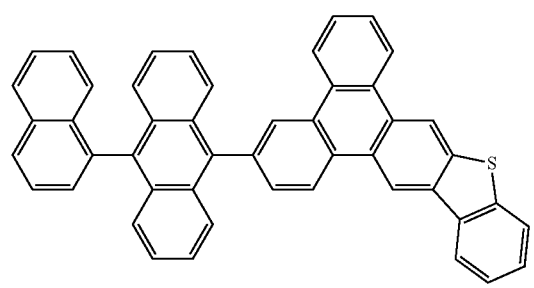
Compound 66
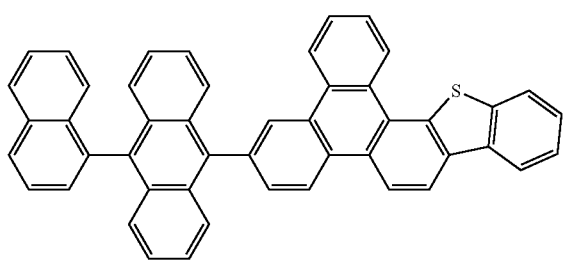
Compound 67
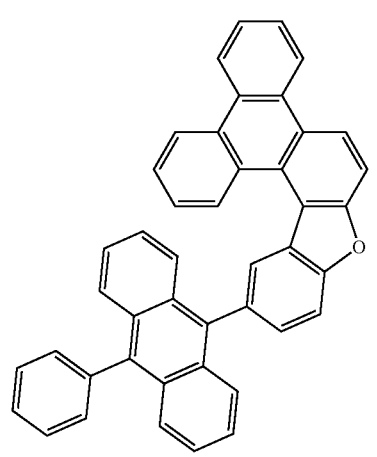
Compound 68
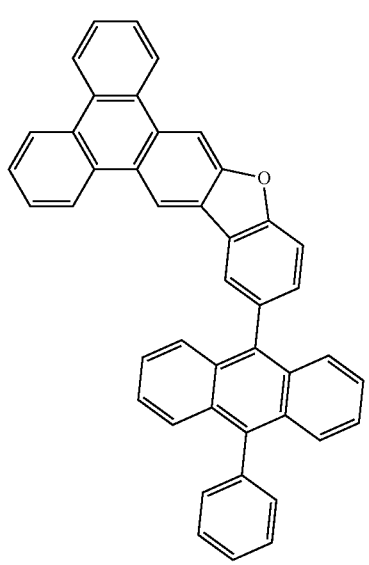

-continued
Compound 69
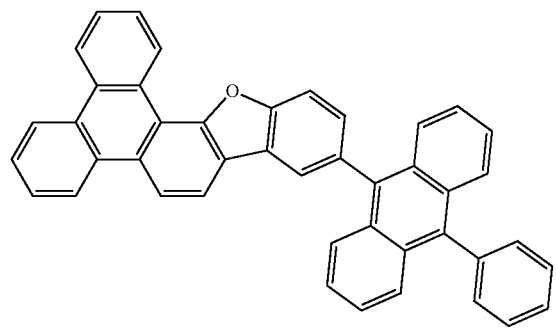 [SMILES: c1ccc(-c2c3ccccc3c(-c3ccc4oc5c(ccc6c7ccccc7c7ccccc7c65)c4c3)c3ccccc23)cc1]
Compound 70
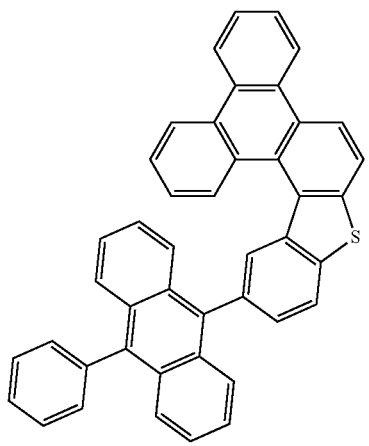
Compound 71
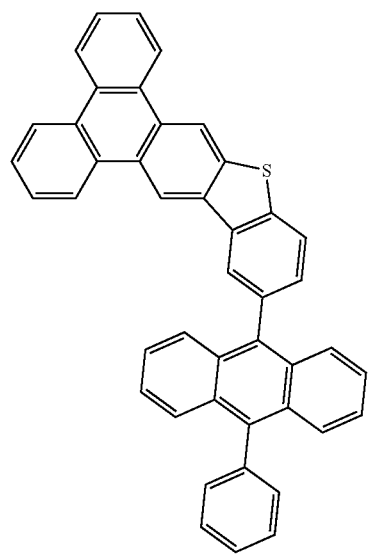
Compound 72
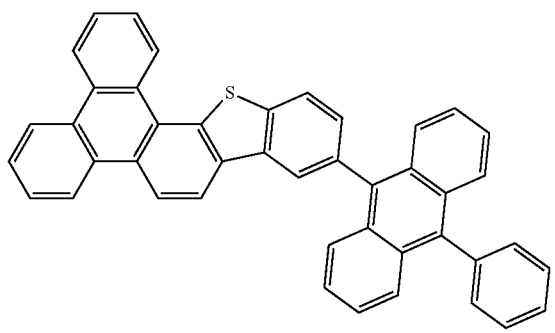 [SMILES: c1ccc(-c2c3ccccc3c(-c3ccc4sc5c(ccc6c7ccccc7c7ccccc7c65)c4c3)c3ccccc23)cc1]
Compound 73
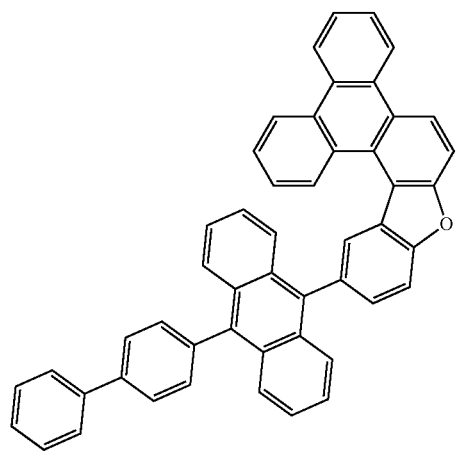
Compound 74
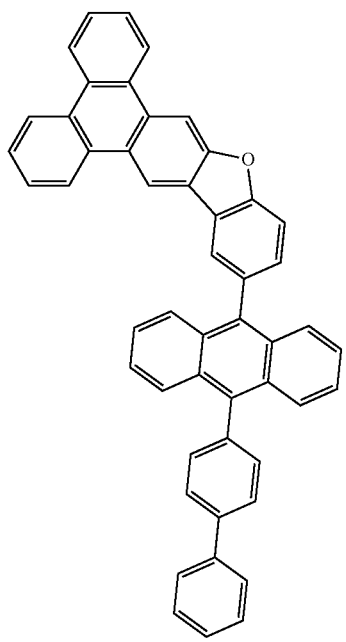

-continued
Compound 75
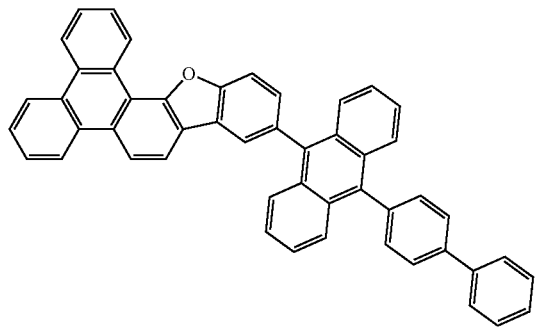
Compound 76
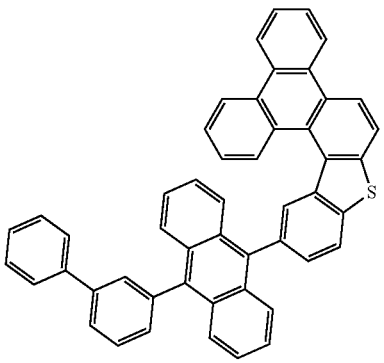
Compound 77
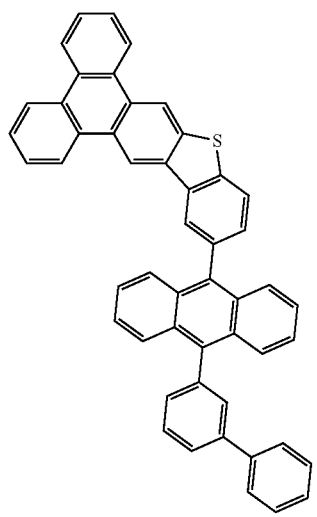
Compound 78
Compound 79
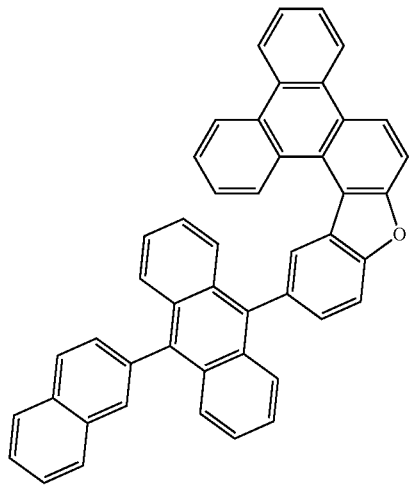
Compound 80
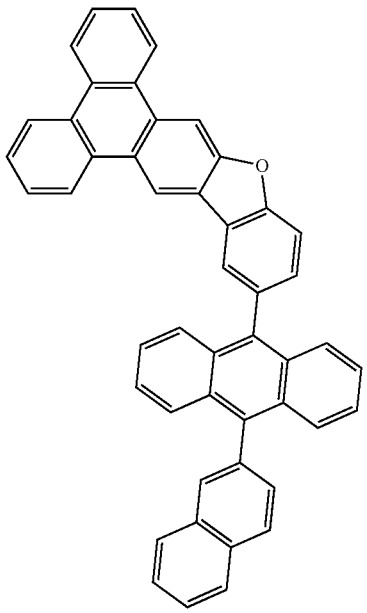

-continued
Compound 81
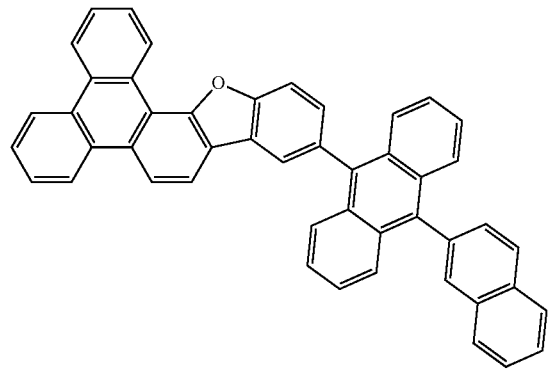
Compound 82
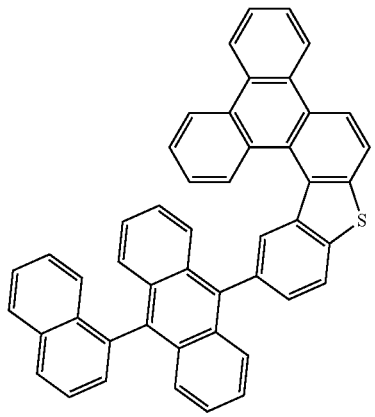
Compound 83
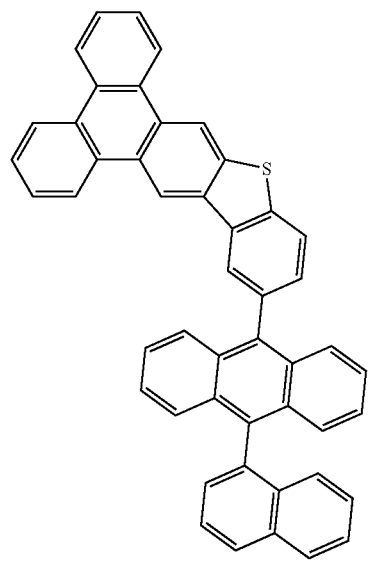
Compound 84
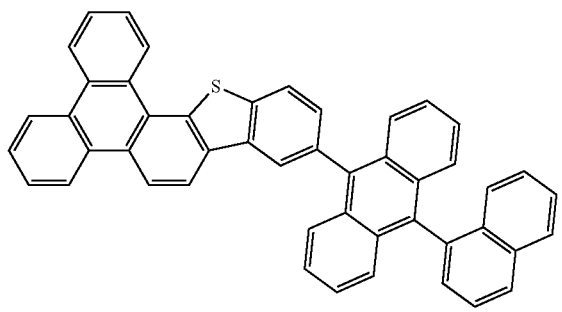
Compound 85
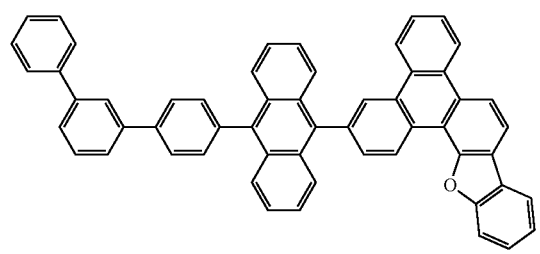
Compound 86
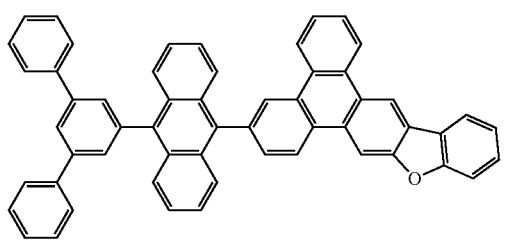
Compound 87
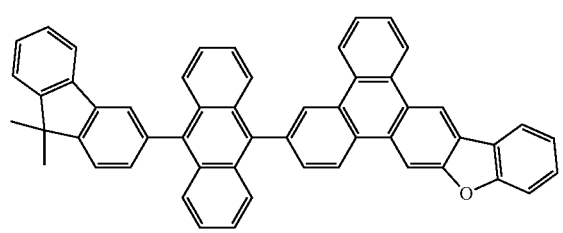
Compound 88
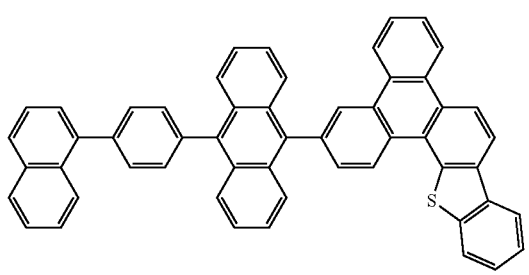

-continued
Compound 89
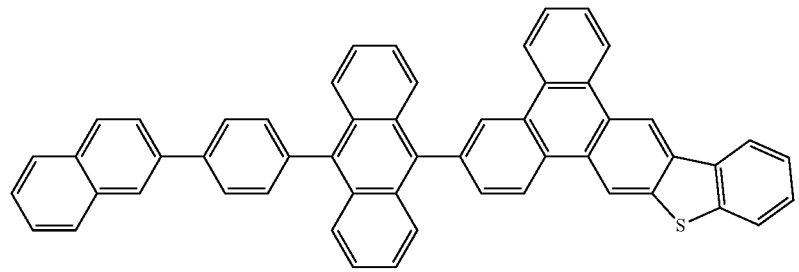
Compound 90
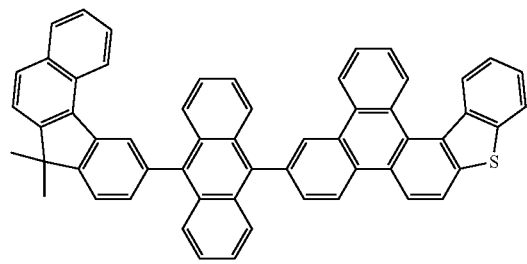
Compound 91
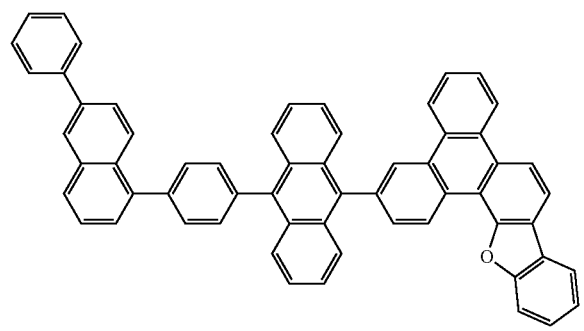
Compound 92
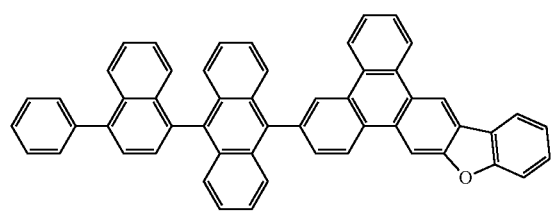
Compound 93
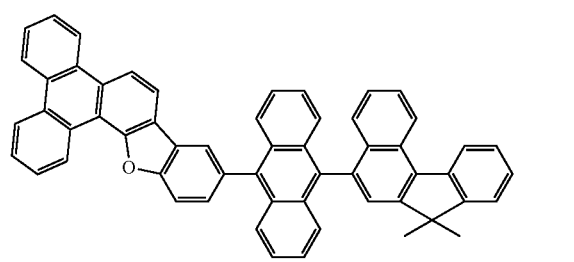
Compound 94
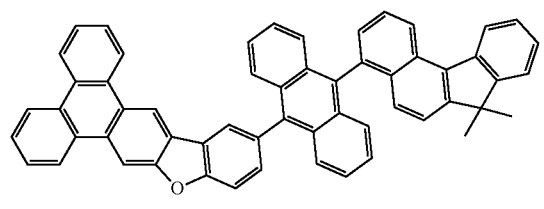
Compound 95
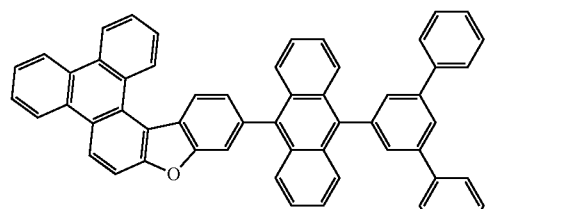
Compound 96
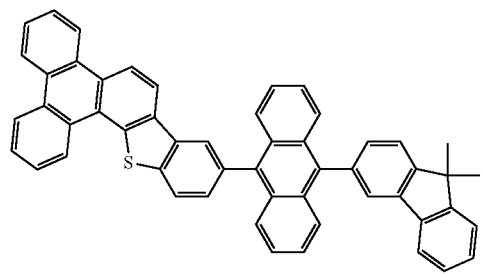 [SMILES: CC1(C)c2ccccc2-c2cc(-c3c4ccccc4c(-c4ccc5sc6c(ccc7c8ccccc8c8ccccc8c76)c5c4)c4ccccc34)ccc21]
Compound 97

-continued
Compound 98
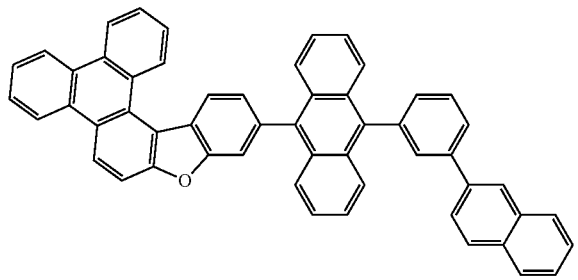 [SMILES: c1cc(-c2ccc3ccccc3c2)cc(-c2c3ccccc3c(-c3ccc4c(c3)sc3ccc5c6ccccc6c6ccccc6c5c34)c3ccccc23)c1]
Compound 99
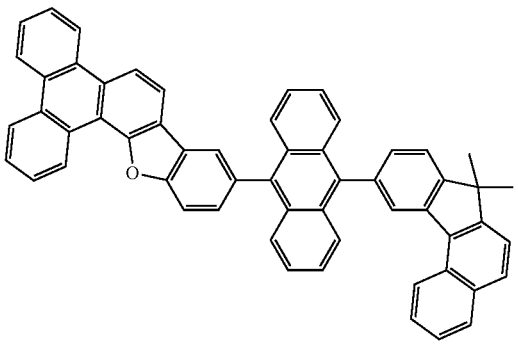
Compound 100
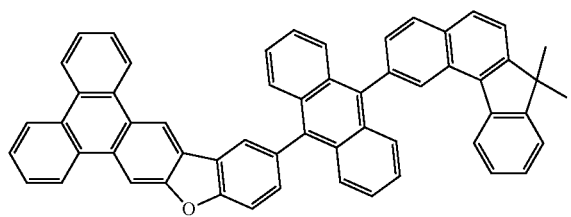
Compound 101
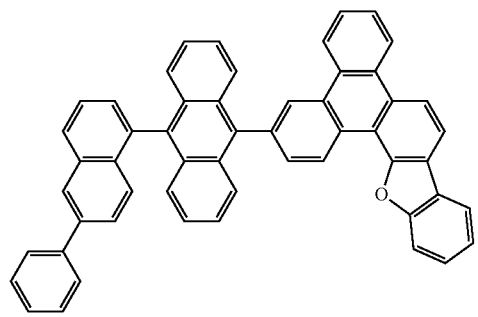
Compound 102
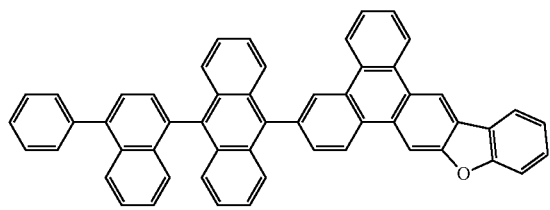
Compound 103
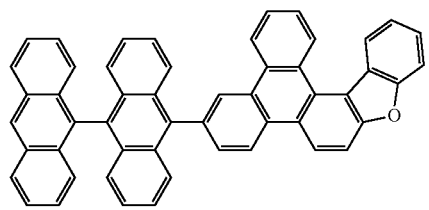
Compound 104
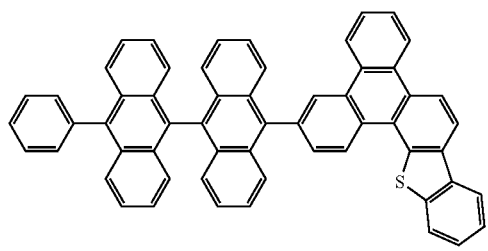
Compound 105
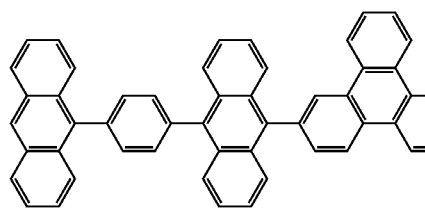
Compound 106
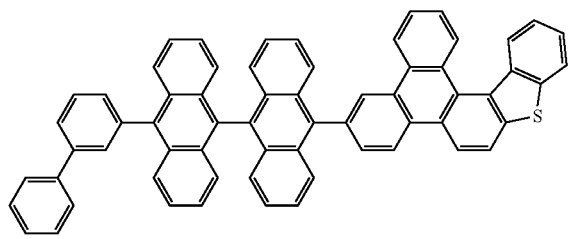
Compound 107
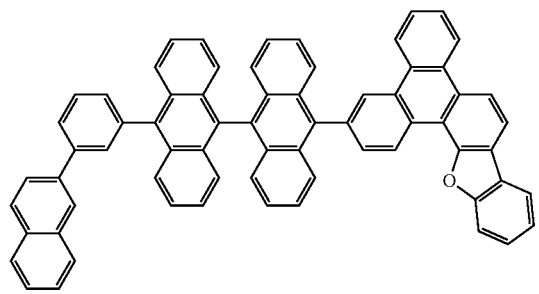

Compound 108
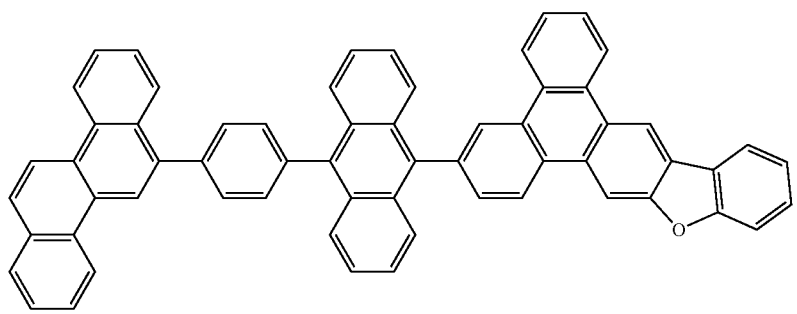
Compound 109
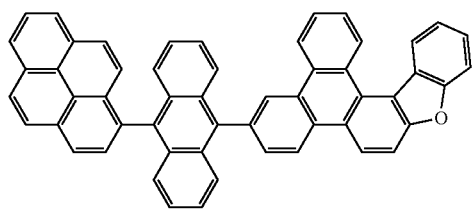
Compound 110
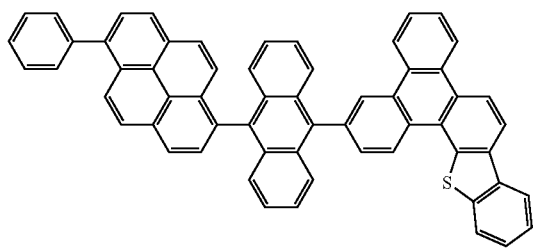
Compound 111
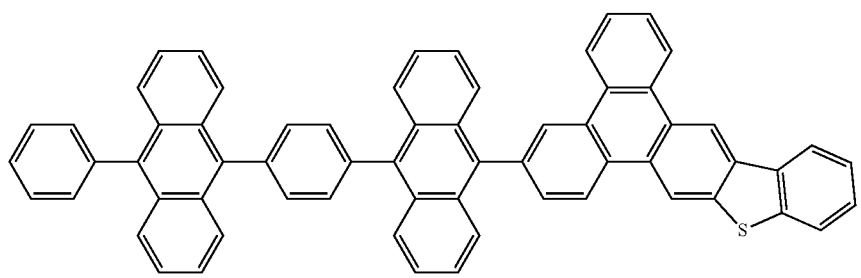
Compound 112
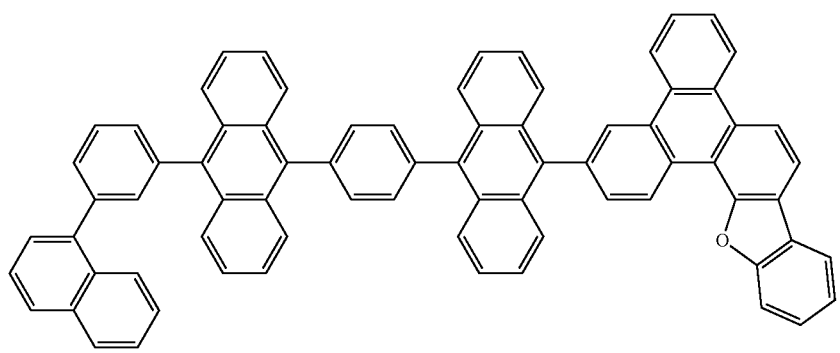
Compound 113
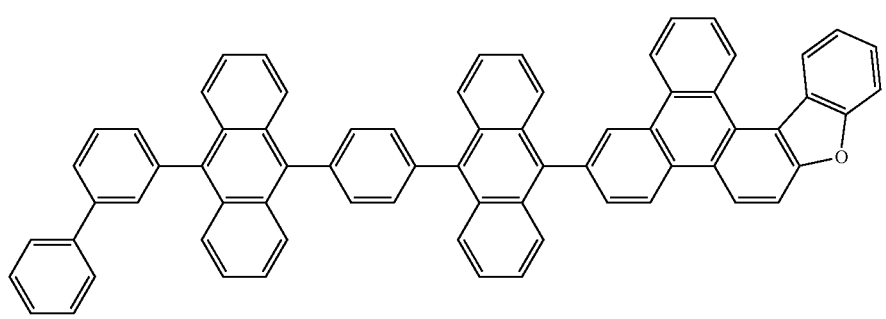

Compound 114
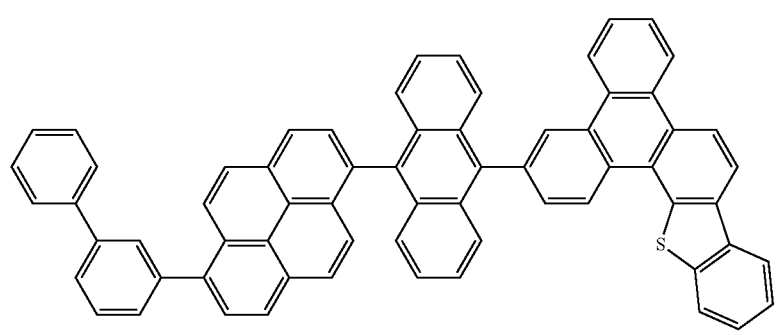
Compound 115
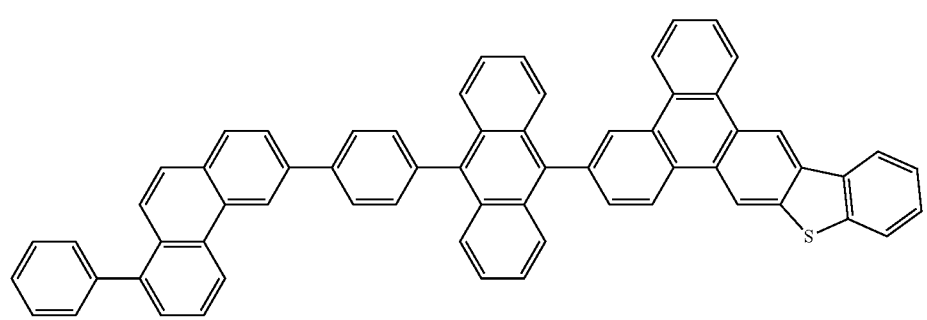
Compound 116
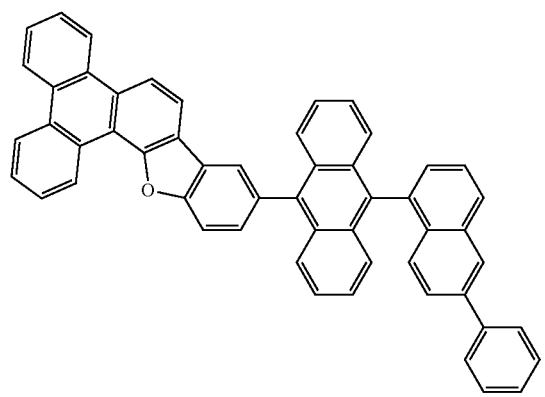
Compound 117
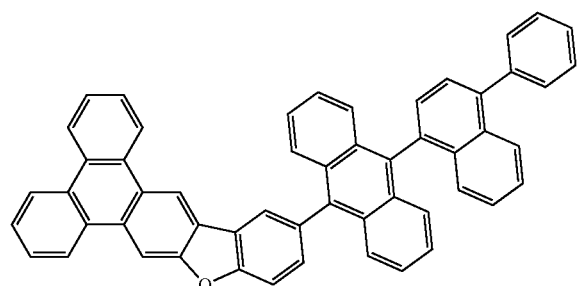
Compound 118
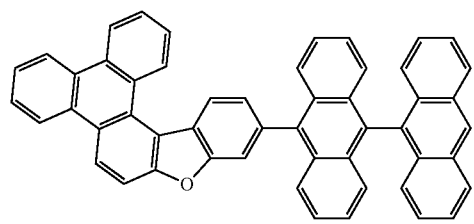
Compound 119
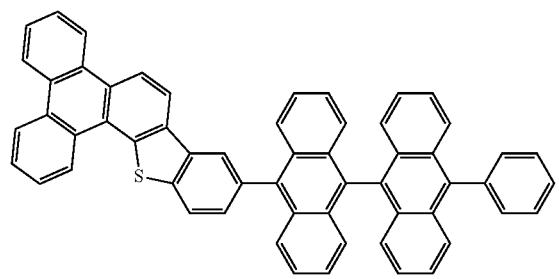

-continued
Compound 120
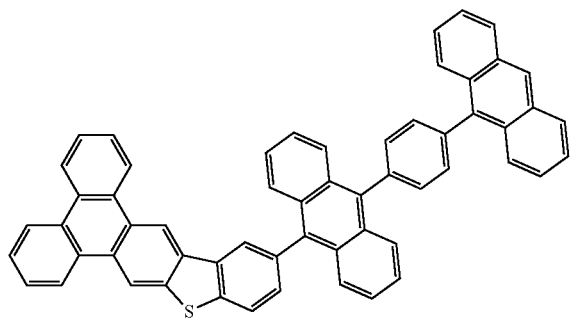
Compound 121
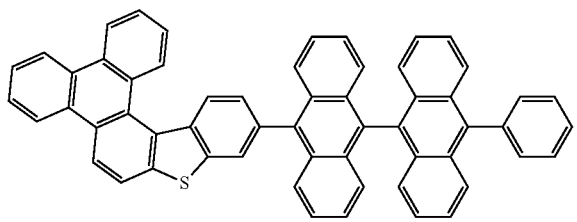 [SMILES: c1ccc(-c2c3ccccc3c(-c3c4ccccc4c(-c4ccc5c(c4)sc4ccc6c7ccccc7c7ccccc7c6c45)c4ccccc34)c3ccccc23)cc1]
Compound 122
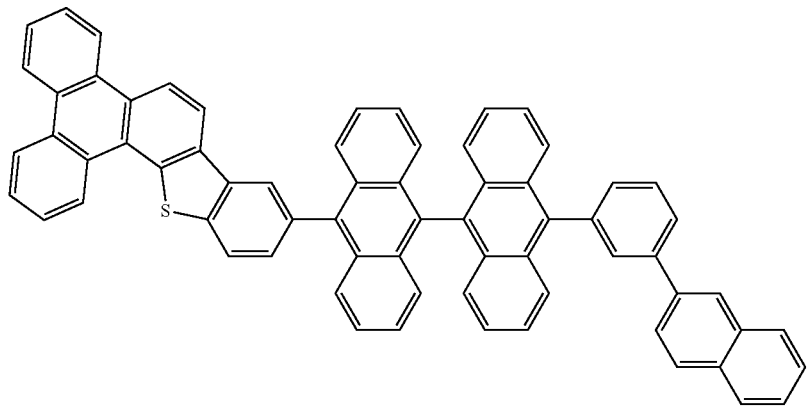
Compound 123
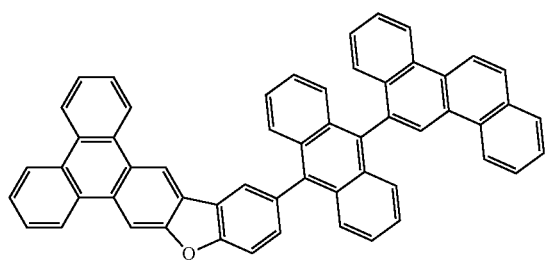
Compound 124
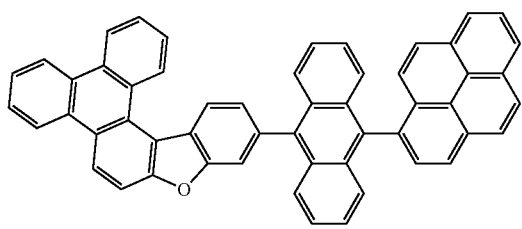
Compound 125
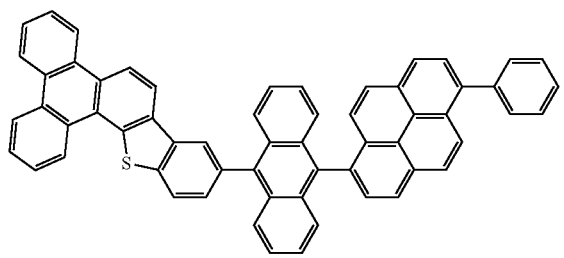
Compound 126
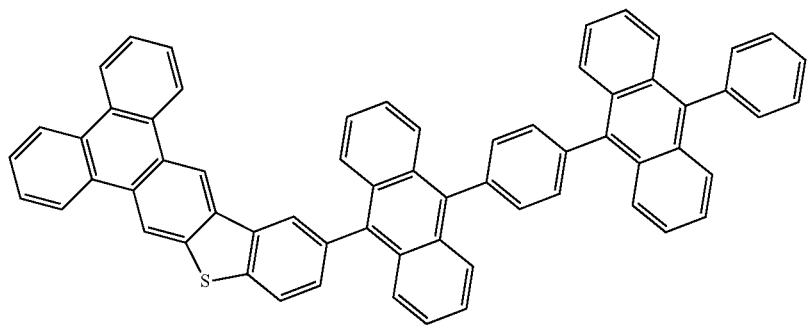

-continued
Compound 127
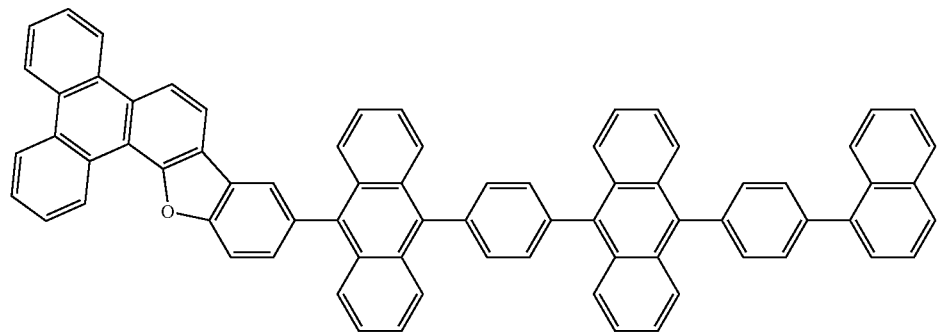
Compound 128
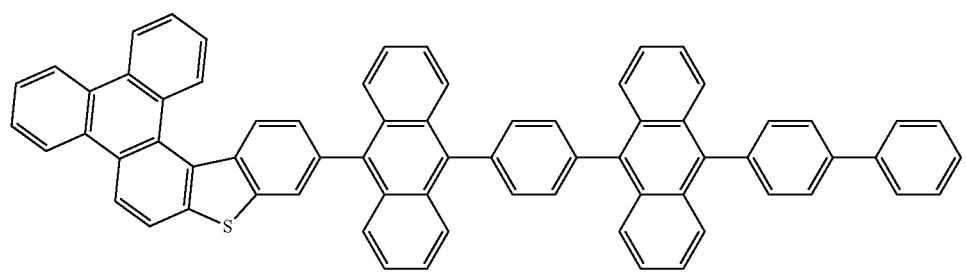
Compound 129
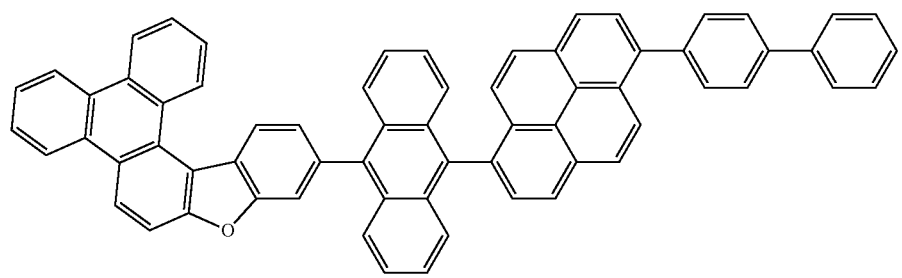
Compound 130
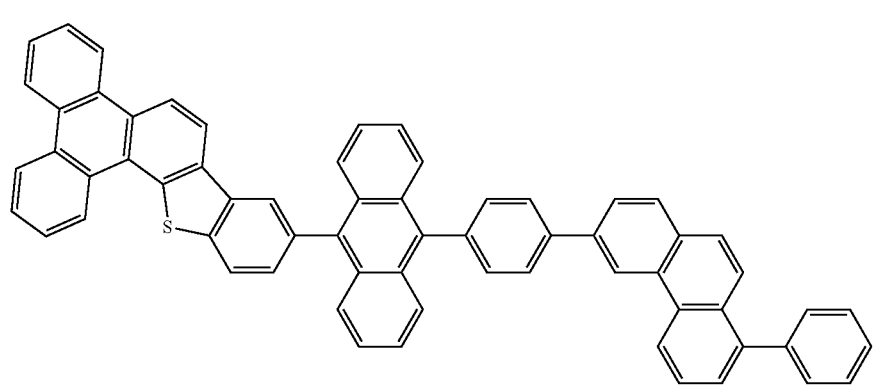 [SMILES: c1ccc(-c2cccc3c2ccc2ccc(-c4ccc(-c5c6ccccc6c(-c6ccc7sc8c(ccc9c%10ccccc%10c%10ccccc%10c98)c7c6)c6ccccc56)cc4)cc23)cc1]

Compound 131
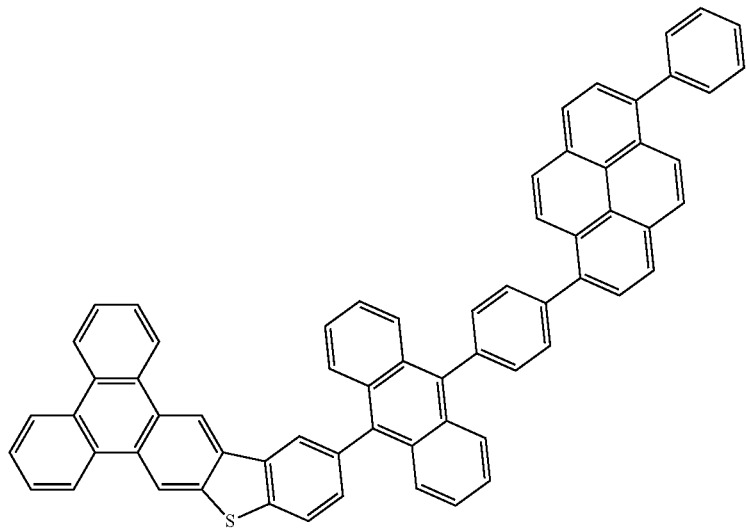
Compound 132
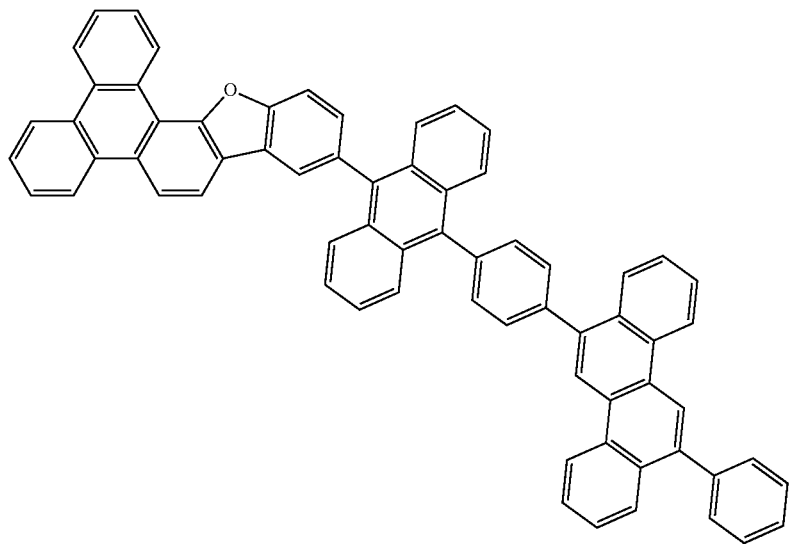
Compound 133
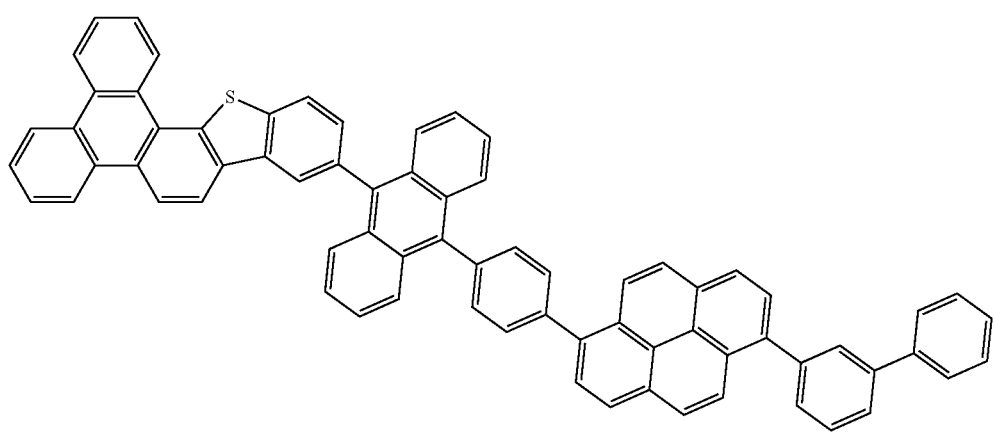

Compound 134
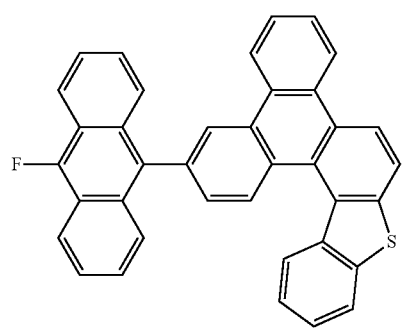
Compound 135
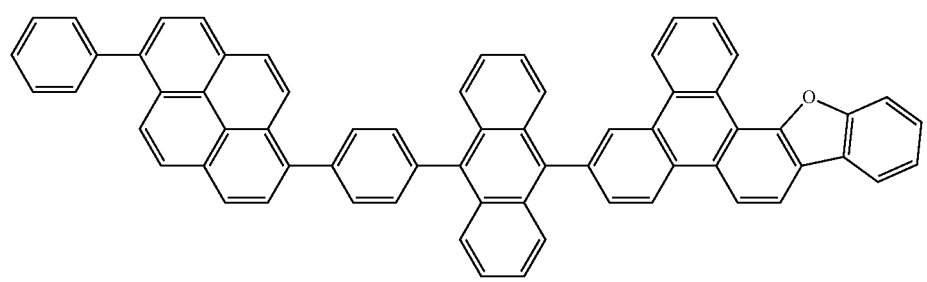
Compound 136
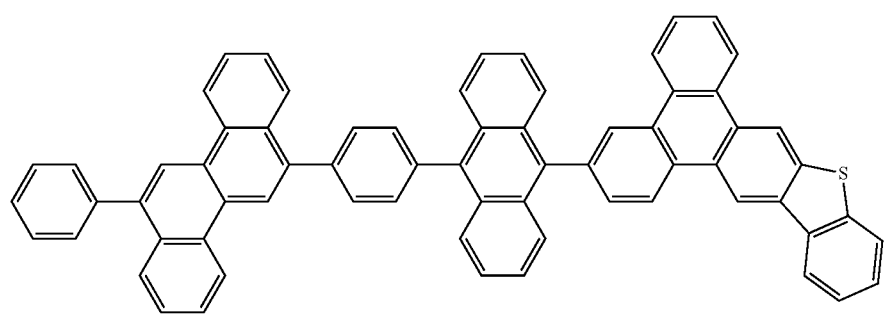
Compound 137
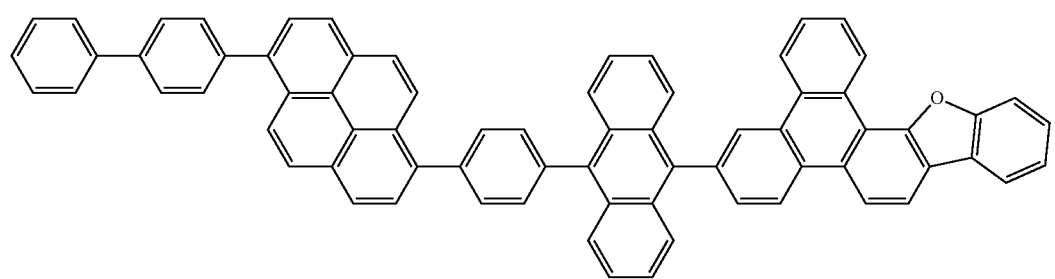
Compound 138
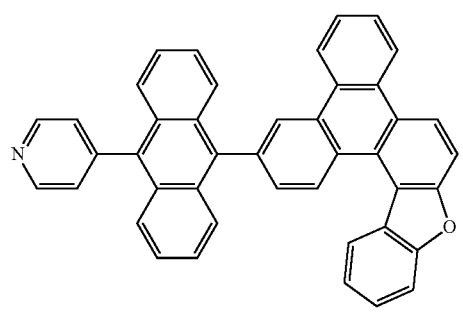
Compound 139
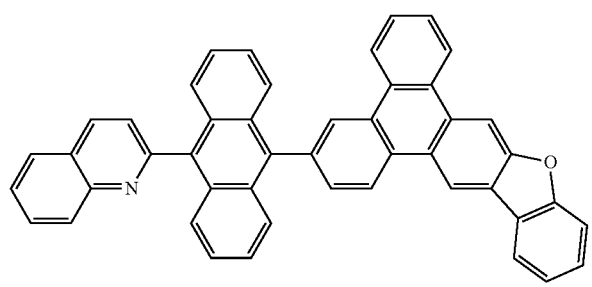

-continued
Compound 140
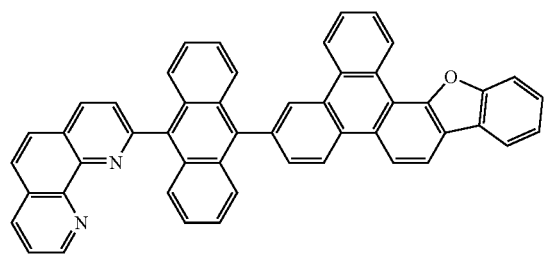
Compound 141
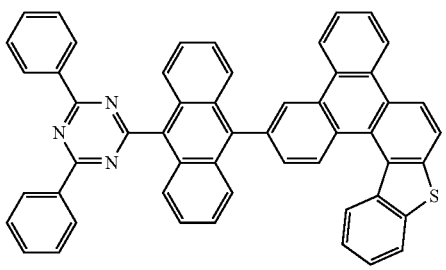
Compound 142
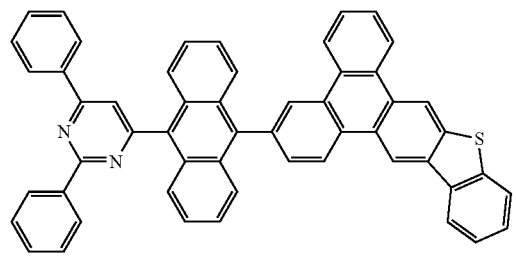
Compound 143
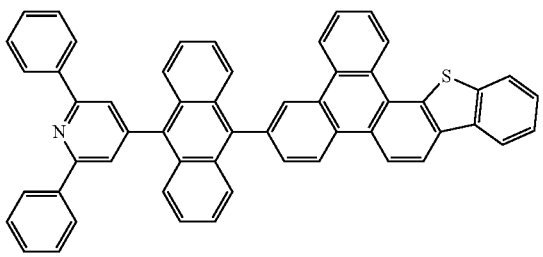
Compound 144
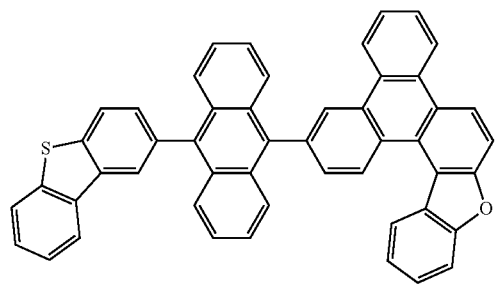
Compound 145
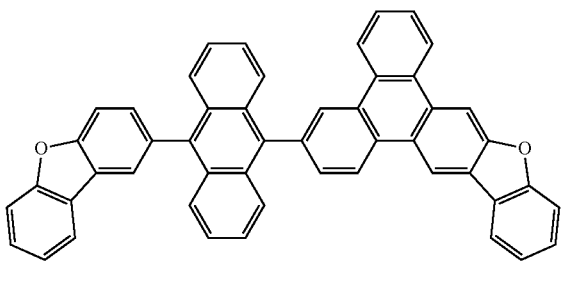
Compound 146
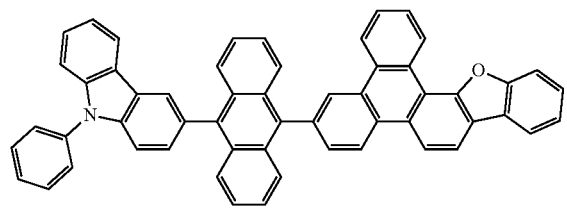
Compound 147
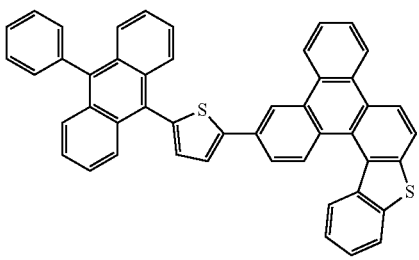

-continued
Compound 148
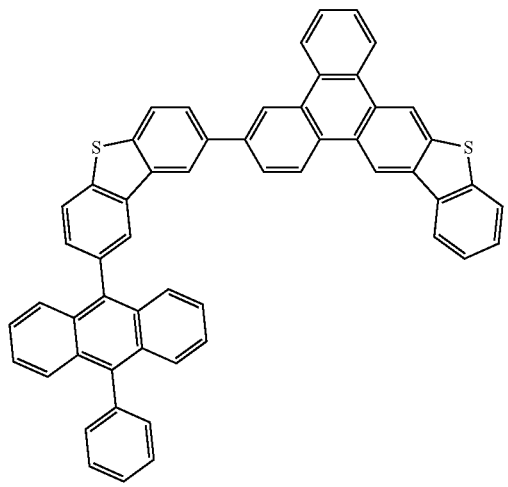
Compound 149
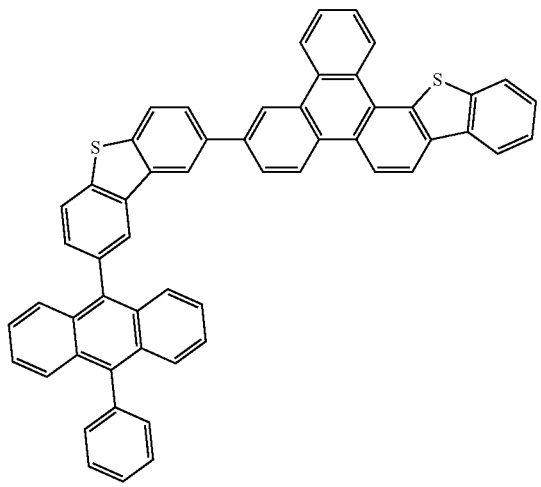
Compound 150
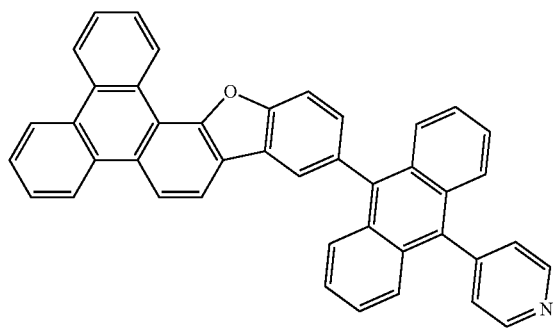
Compound 151
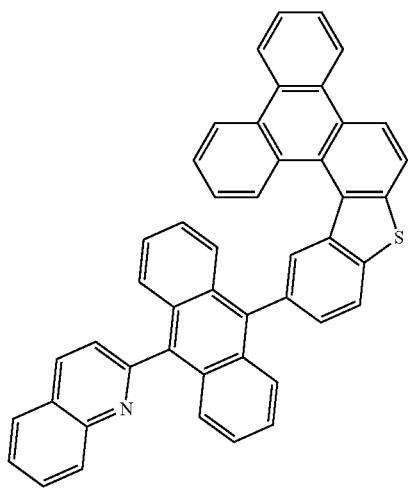
Compound 152
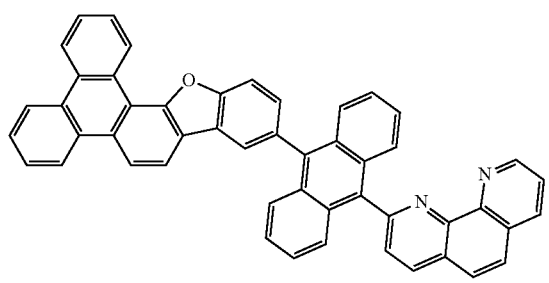 [SMILES: c1cnc2c(c1)ccc1ccc(-c3c4ccccc4c(-c4ccc5sc6c(ccc7c8ccccc8c8ccccc8c76)c5c4)c4ccccc34)nc12]
Compound 153
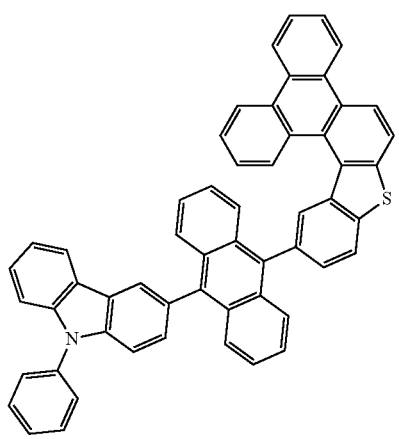

-continued
Compound 154
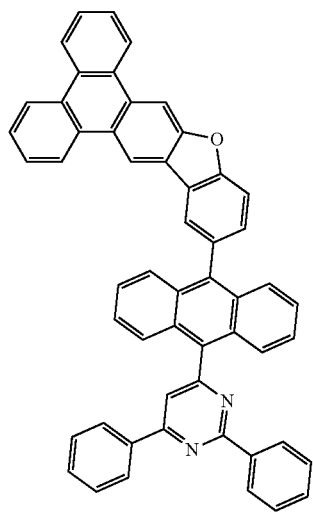
Compound 155
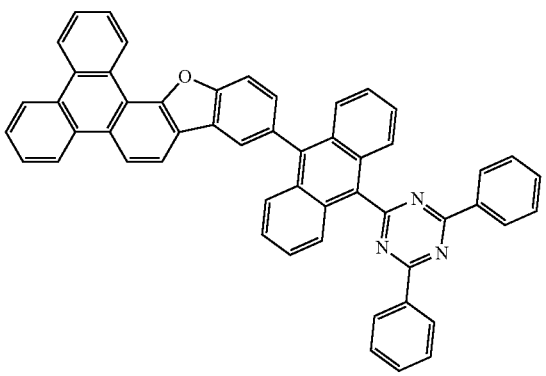
Compound 156
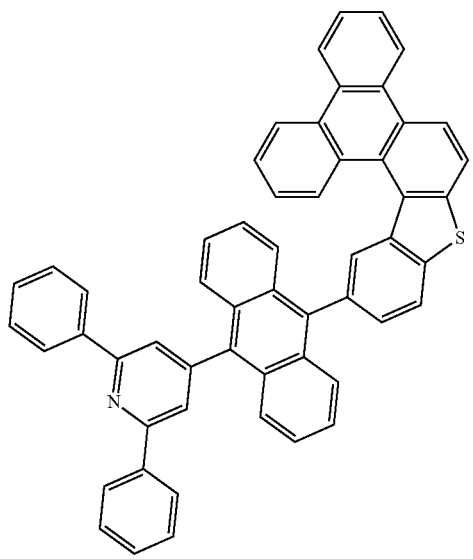 [SMILES: c1ccc(-c2cc(-c3c4ccccc4c(-c4ccc5sc6ccc7c8ccccc8c8ccccc8c7c6c5c4)c4ccccc34)cc(-c3ccccc3)n2)cc1]
Compound 157
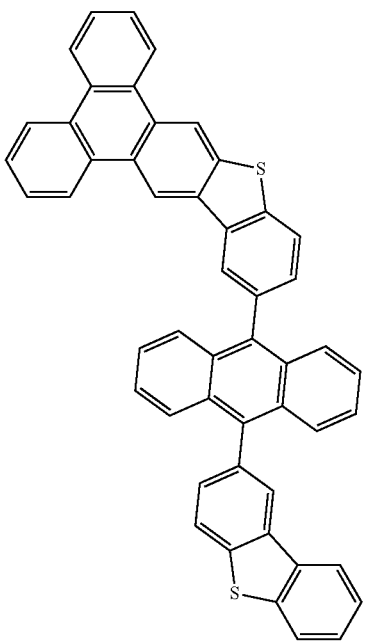
Compound 158
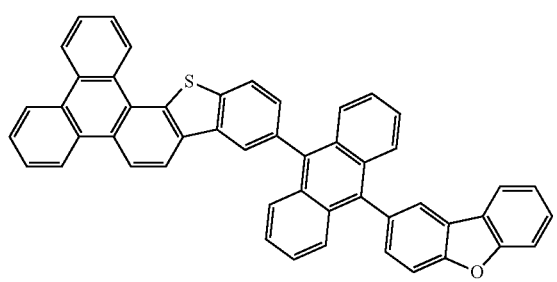
Compound 159
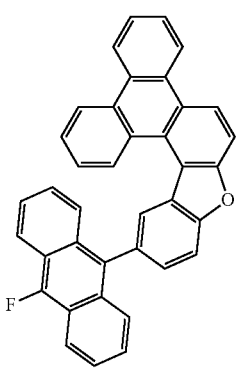

-continued
Compound 160
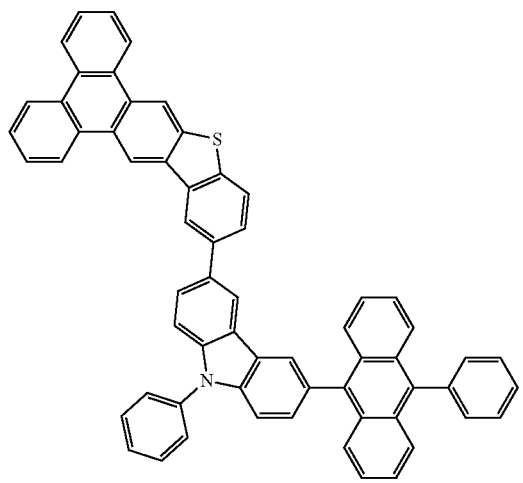
Compound 161
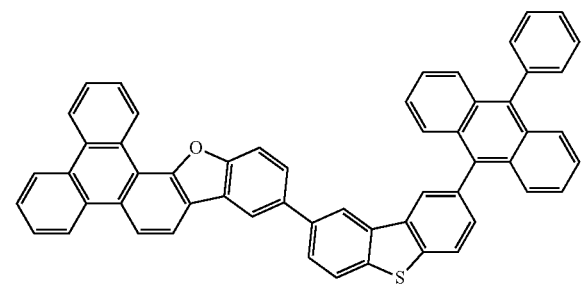
Compound 162
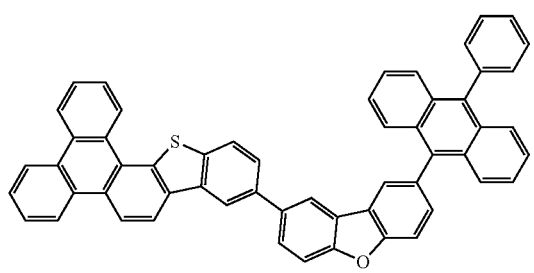
Compound 163
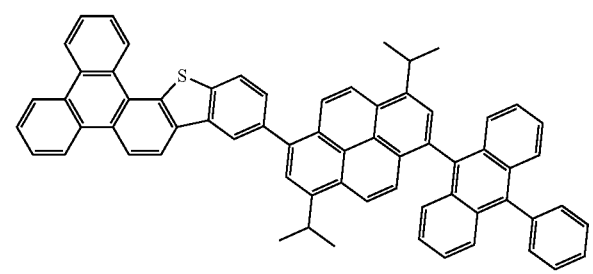
Compound 164
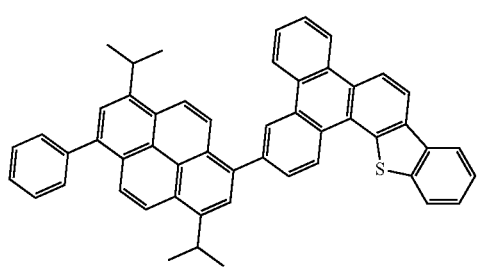
Compound 165
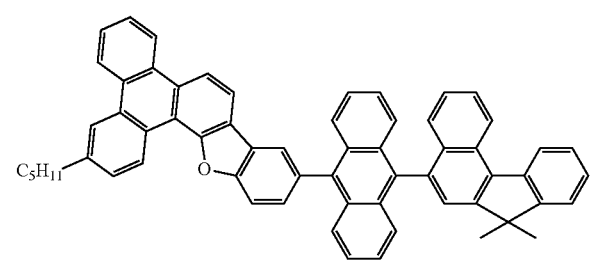
Compond 166
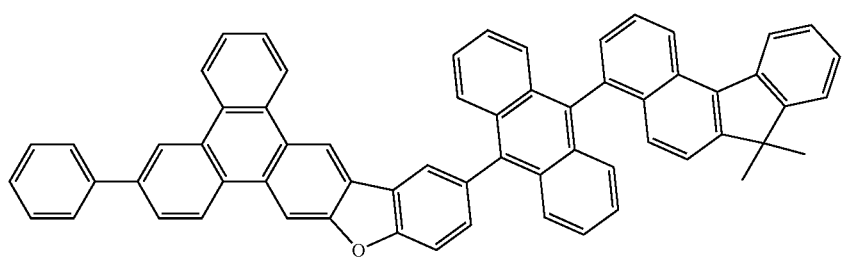

Compound 167
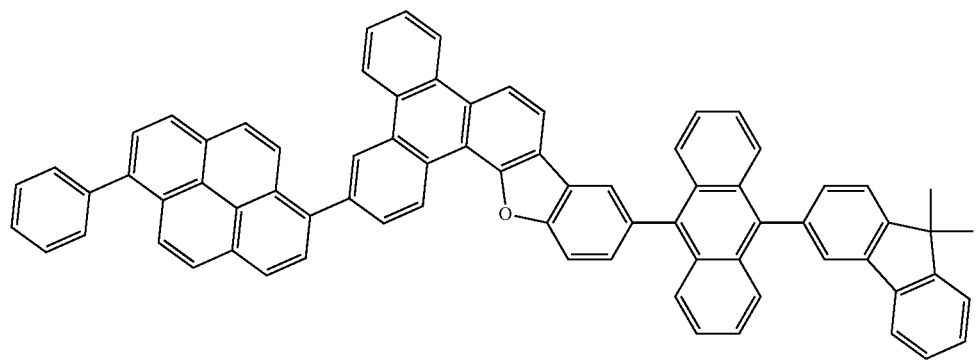
Compound 168
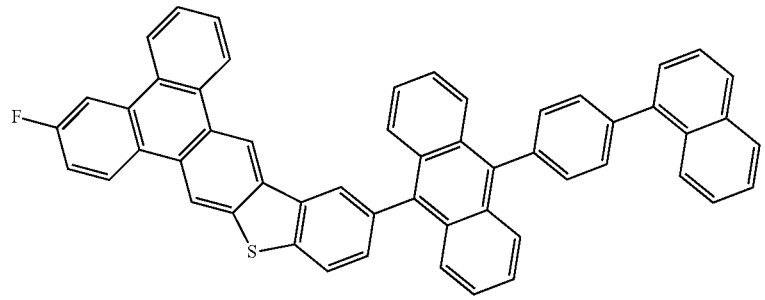
Compound 169
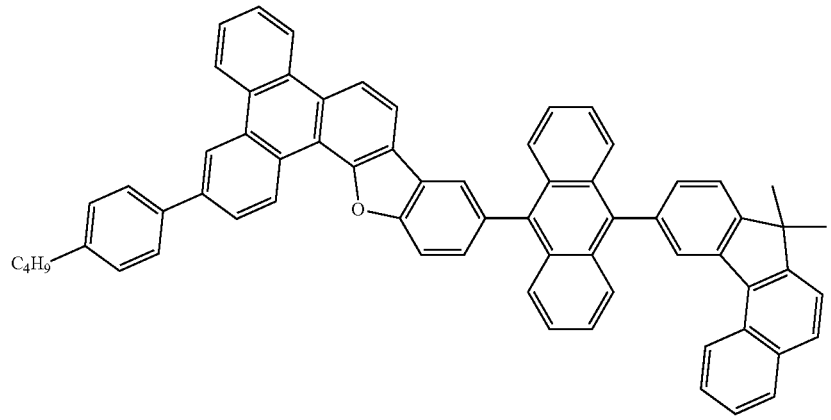
Compound 170
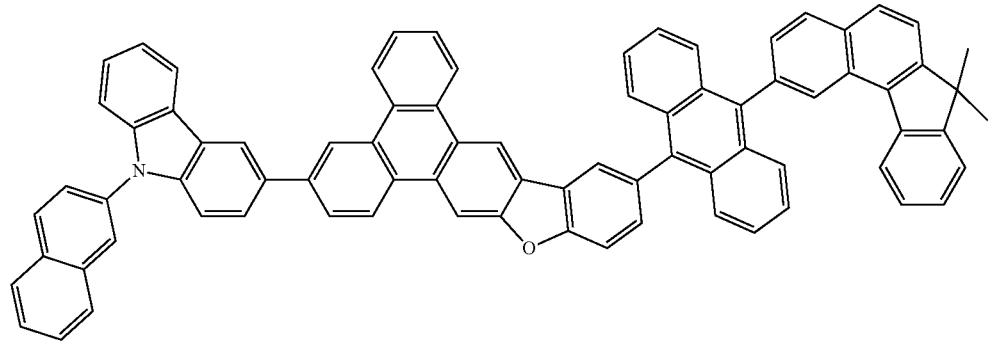

-continued

Compound 171

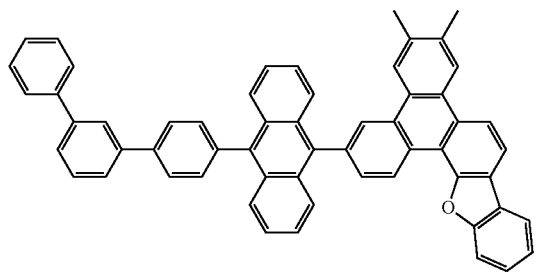

Compound 172

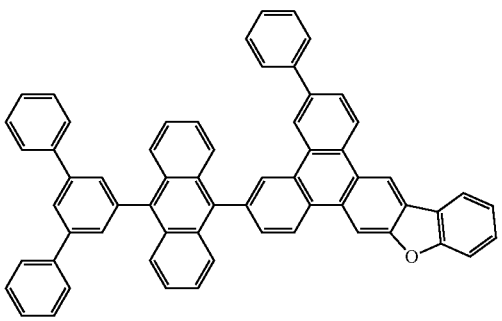

Compound 173

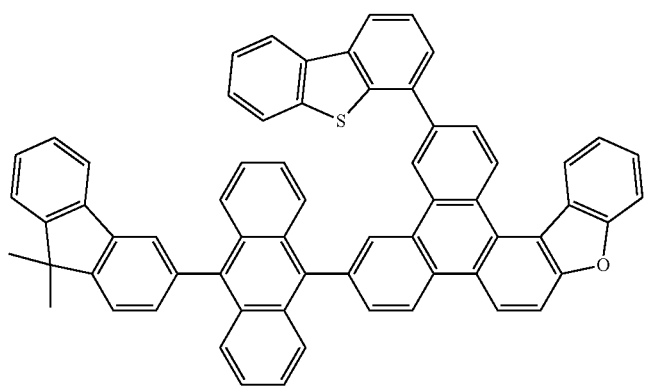

Compound 174

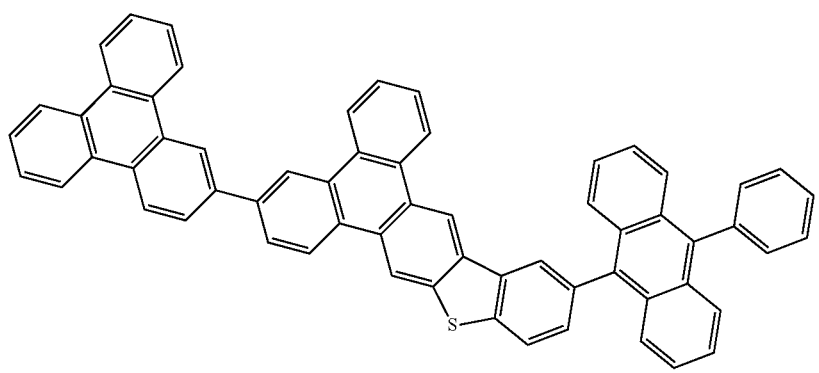

In another embodiment of the present invention, an organic electroluminescence device is disclosed. The organic electroluminescence device comprises a pair of electrodes composed of a cathode and an anode, and a light emitting layer between the pair of electrodes. The light emitting layer comprises the organic compound of formula (A).

In some embodiments, the light emitting layer comprising the organic compound of formula (A) is a fluorescent host material. In particular, the light emitting layer emits blue fluorescence.

In a further embodiment of the present invention, the organic electroluminescence device is a lighting panel. In other embodiment of the present invention, the organic electroluminescence device is a backlight panel.

Detailed preparation of the organic compounds of the present invention will be clarified by exemplary embodiments below, but the present invention is not limited thereto. EXAMPLES 1 to 35 show the preparation of the organic compounds of the present invention, and EXAMPLE 36 shows the fabrication and test reports of the organic EL devices.

Example 1

Synthesis of 2-([1,1'-biphenyl]-2-yl)-8-bromodibenzo[b,d]furan

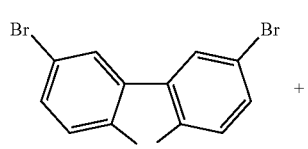

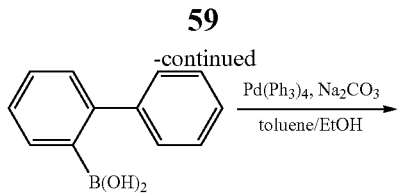

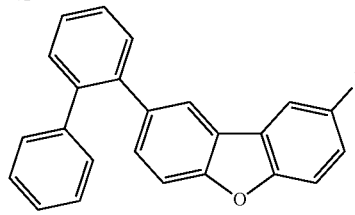

A mixture of 10 g (30.7 mmol) of 2,8-dibromodibenzo[b,d]furan, 6.07 g (30.7 mmol) of [1,1'-biphenyl]-2-ylboronic acid, 0.35 g (0.3 mmol) of Pd(Ph$_3$)$_4$, 30.7 ml of 2M Na$_2$CO$_3$, 80 ml of EtOH and 160 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 6.8 g of 2-([1,1'-biphenyl]-2-yl)-8-bromodibenzo[b,d]furan as white solid (55.5%). $^1$H NMR (CDCl$_3$, 400 MHz): chemical shift (ppm) 8.19 (s, 1H), 7.88-7.81 (m, 5H), 7.74-7.72 (s, 2H), 7.52-7.39 (m, 7H).

Synthesis of
13-bromotriphenyleno[2,3-b]benzofuran

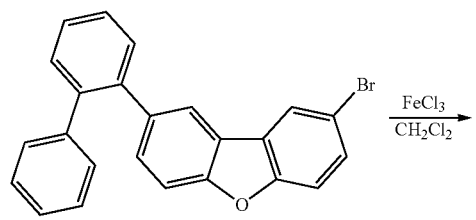

The compound 2-([1,1'-biphenyl]-2-yl)-8-bromodibenzo[b,d]furan (6.8 g, 17 mmol) was mixed with 100 ml of CH$_2$Cl$_2$. To the mixture, 27.6 g of FeCl$_3$ (170 mmol) was added and the mixture was stirred for 1 hrs. After the reaction finished, the solvent was removed under reduced pressure, and the crude product was purified by column chromatography, yielding 2.9 g of 13-bromotriphenyleno[2,3-b]benzofuran as white solid (43%). $^1$H NMR (CDCl$_3$, 400 MHz): chemical shift (ppm) 8.95-8.91 (m, 3H), 8.19-8.14 (m, 4H), 7.87-7.83 (m, 4H), 7.58 (d, 1H), 7.39 (d, 1H).

Synthesis of 4,4,5,5-tetramethyl-2-(triphenyleno[2,3-b]benzofuran-13-yl)-1,3,2-dioxaborolane

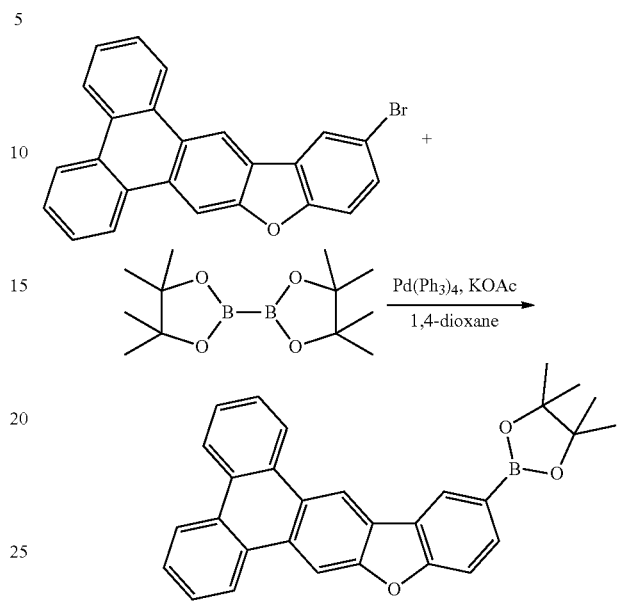

A mixture of 5 g (12.6 mmol) of 13-bromotriphenyleno[2,3-b]-benzofuran, 3.84 g (15.1 mmol) of bis(pinacolato)diboron, 0.58 g (0.5 mmol) of Pd(Ph$_3$)$_4$, 2.47 g (25.1 mmol) of potassium acetate, and 50 ml of 1,4-dioxane was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 4.1 g of 4,4,5,5-tetramethyl-2-(triphenyleno[2,3-b]benzofuran-13-yl)-1,3,2-dioxaborolane as white solid (73.2%). $^1$H NMR (CDCl$_3$, 400 MHz): chemical shift (ppm) 8.93-8.89 (m, 3H), 8.14-8.12 (m, 3H), 7.89-7.83 (m, 5H), 7.64 (d, 1H), 7.48 (d, 1H), 1.28 (s, 12H).

Synthesis of 13-(10-phenylanthracen-9-yl)triphenyleno[2,3-b]-benzofuran (Compound 20)

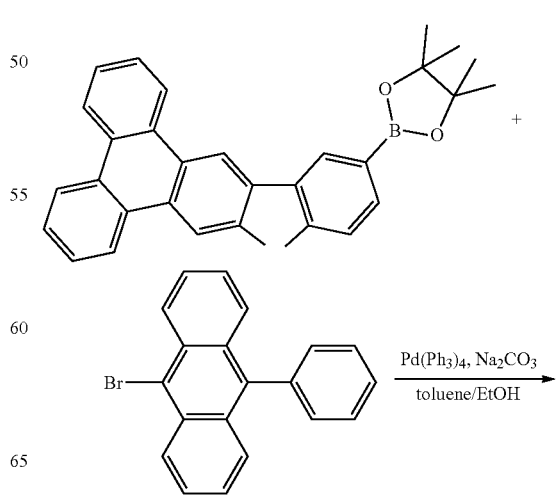

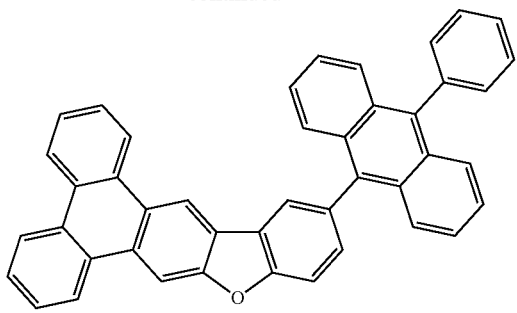

A mixture of 3 g (6.75 mmol) of 4,4,5,5-tetramethyl-2-(triphenyleno[2,3-b]benzofuran-13-yl)-1,3,2-dioxaborolane, 2.7 g (8.1 mmol) of 9-bromo-10-phenylanthracene, 0.16 g (0.14 mmol) of Pd(Ph$_3$)$_4$, 6.8 ml of 2M Na$_2$CO$_3$, 20 ml of EtOH and 40 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 2.4 g of 2-([1,1'-biphenyl]-2-yl)-8-bromodibenzo[b,d]furan as white solid (62.3%). $^1$H NMR (CDCl$_3$, 400 MHz): chemical shift (ppm) 8.92-8.87 (m, 3H), 8.12-8.09 (m, 3H), 7.88-7.85 (m, 6H), 7.84-7.81 (m, 3H), 7.70 (s, 2H), 7.49-7.43 (m, 4H), 7.40-7.36 (m, 5H).

Example 2-17

We have used the same synthesis methods to get a series of intermediates and the following compounds are synthesized analogously.

| Ex. | Intermediate I | Intermediate II | Product | Yield |
|---|---|---|---|---|
| 2 | | | Compound 21 | 61% |
| 3 | | | Compound 22 | 59% |
| 4 | | | Compound 26 | 63% |

-continued
| Ex. | Intermediate I | Intermediate II | Product | Yield |
|---|---|---|---|---|
| 5 | 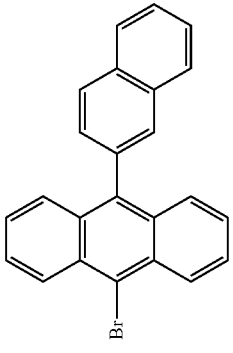 | 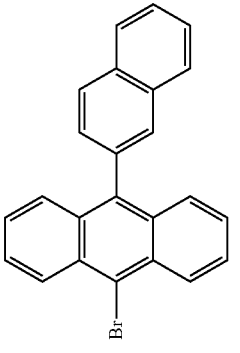 | 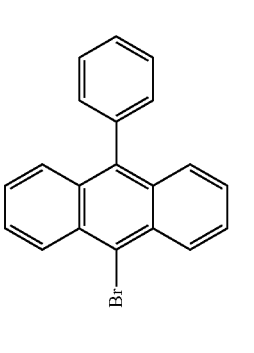
Compound 31 | 57% |
| 6 | 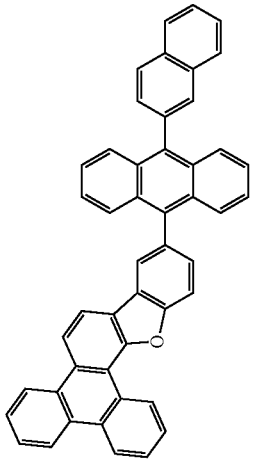 | 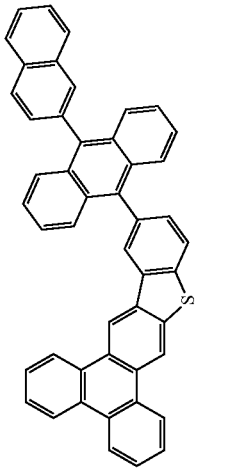 | 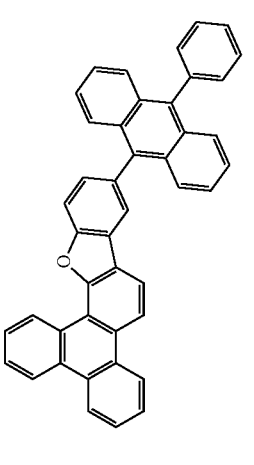
Compound 35 | 65% |
| 7 | 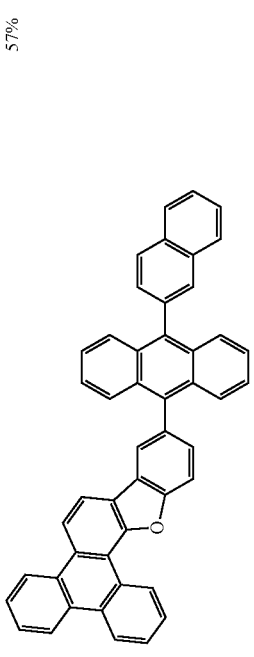 | 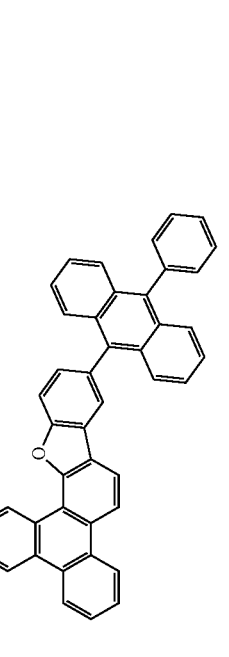 | 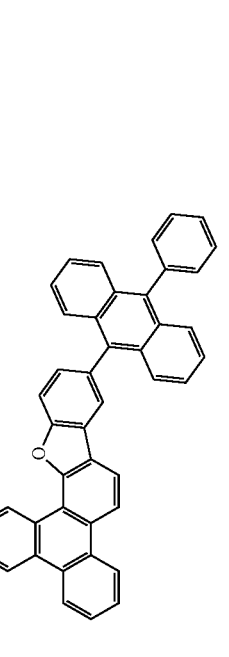
Compound 69 | 58% |

-continued

| Ex. | Intermediate I | Intermediate II | Product | Yield |
|---|---|---|---|---|
| 8 | | | Compound 72 | 55% |
| 9 | | | Compound 95 | 60% |
| 10 | | | Compound 96 | 52% |

-continued

| Ex. | Intermediate I | Intermediate II | Product | Yield |
|---|---|---|---|---|
| 11 | | | Compound 98 | 54% |
| 12 | | | Compound 117 | 52% |
| 13 | | | Compound 121 | 50% |

-continued

| Ex. | Intermediate I | Intermediate II | Product | Yield |
|---|---|---|---|---|
| 14 | | | | 61% |
| 15 | | | Compound 130 | 57% |
| 16 | | | Compound 152 | 44% |

| Ex. | Intermediate I | Intermediate II | Product | Yield |
|---|---|---|---|---|
| 17 | *(structure)* | *(structure)* | Compound 156 | 41% |
| | | | Compound 163 | |

Example 18

Synthesis of 1-bromo-2-iodo-4-methoxybenzene

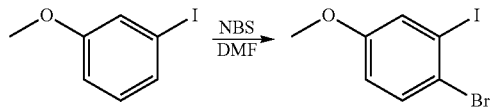

A mixture of 40 g (171 mmol) of 1-iodo-3-methoxybenzene, 32 g (179 mmol) of N-bromosuccinimide, and 600 ml of DMF was degassed and placed under nitrogen, and then heated at 80° C. for 12 hrs. After the reaction finished, the mixture was allowed to cool to room temperature. Subsequently, the solvent was removed under reduced pressure, and the crude product was purified by column chromatography, yielding 45 g of 1-bromo-2-iodo-4-methoxybenzene as yellow oil (84.1%). $^1$H NMR (CDCl$_3$, 400 MHz): chemical shift (ppm) 7.43 (dd, 1H), 7.35 (dd, 1H), 6.73 (dd, 1H), 3.74 (s, 3H).

Synthesis of 2-bromo-5-methoxy-1,1'-biphenyl

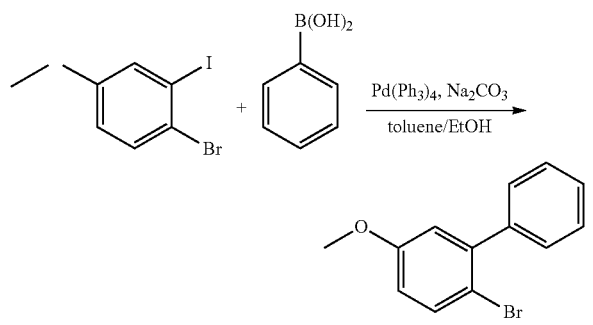

A mixture of 40 g (127.8 mmol) of 1-bromo-2-iodo-4-methoxybenzene, 15.6 g (127.8 mmol) of phenylboronic acid, 2.95 g (2.56 mmol) of Pd(Ph$_3$)$_4$, 155 ml of 2M Na$_2$CO$_3$, 100 ml of EtOH and 300 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 30 g of 2-bromo-5-methoxy-1,1'-biphenyl as colorless liquid (89.2%). $^1$H NMR (CDCl$_3$, 400 MHz): chemical shift (ppm) 7.55 (d, 1H), 7.46-7.38 (m, 5H), 6.89 (d, 1H), 6.79 (dd, 1H), 3.81 (s, 3H).

Synthesis of (5-methoxy-[1,1'-biphenyl]-2-yl)boronic acid

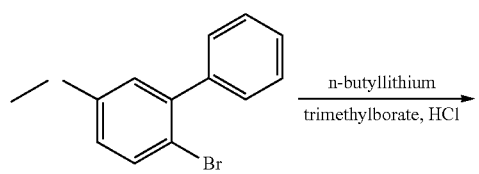

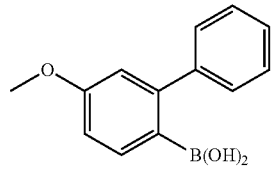

The compound 2-bromo-5-methoxy-1,1'-biphenyl (30 g, 114 mmol) was mixed with 600 ml of dry THF. To the mixture, 54.7 ml of N-butyllithium (137 mmol) was added at −60° C. and the mixture was stirred for 1 hrs. After the reaction finished, 17.8 g (171 mmol) of trimethyl borate was added and the mixture was stirred overnight. 228 ml (228 mmole) of 1M HCl was added and the mixture was stirred for 1 hrs. The mixture was extracted with ethyl acetate/H$_2$O, and the organic layer was removed under reduced pressure. The crude product was washed by hexane, yielding 19.5 g of (5-methoxy-[1,1'-biphenyl]-2-yl)boronic acid as white solid (75%).

Synthesis of 3-(5-methoxy-[1,1'-biphenyl]-2-yl)dibenzo[b,d]-thiophene

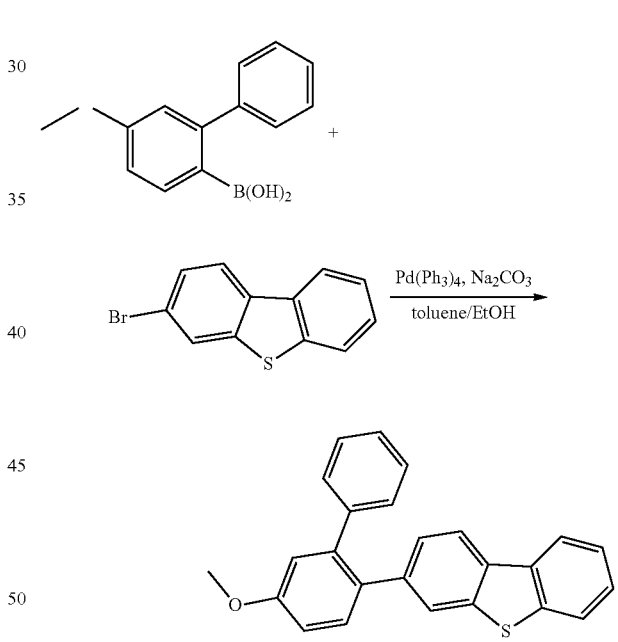

A mixture of 20 g (87.7 mmol) of (5-methoxy-[1,1'-biphenyl]-2-yl)-boronic acid, 25.4 g (96.5 mmol) of 3-bromodibenzo[b,d]thiophene, 2.03 g (1.75 mmol) of Pd(Ph$_3$)$_4$, 87.7 ml of 2M Na$_2$CO$_3$, 200 ml of EtOH and 400 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 23.1 g of 3-(5-methoxy-[1,1'-biphenyl]-2-yl)-dibenzo[b,d]thiophene as white solid (71.9%). $^1$H NMR (CDCl$_3$, 400 MHz): chemical shift (ppm) 8.47 (d, 1H), 8.12-8.06 (m, 3H), 8.01 (d, 1H), 7.77-7.74 (m, 3H), 7.49-7.45 (m, 4H), 7.41-7.38 (m, 2H), 7.02 (d, 1H), 3.81 (s, 3H).

Synthesis of 6-methoxybenzo[b]triphenyleno[2,3-d]thiophene

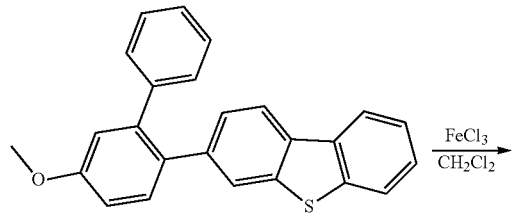

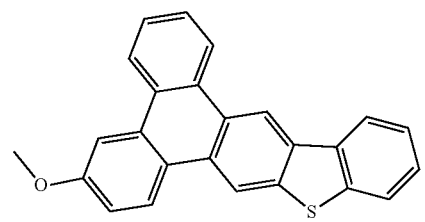

The compound 3-(5-methoxy-[1,1'-biphenyl]-2-yl)dibenzo[b,d]-thiophene (20 g, 54.6 mmol) was mixed with 700 ml of CH₂Cl₂. To the mixture, 88.5 g of FeCl₃ (546 mmol) was added and the mixture was stirred for 1 hrs. After the reaction finished, the solvent was removed under reduced pressure, and the crude product was purified by column chromatography, yielding 8.5 g of 6-methoxybenzo[b]triphenyleno[2,3-d]-thiophene as white solid (42.7%). ¹H NMR (CDCl₃, 400 MHz): chemical shift (ppm) 8.91-8.89 (m, 2H), 8.81 (d, 1H), 8.49 (d, 1H), 8.14 (m, 2H), 7.99 (d, H), 7.89-7.85 (m, 2H), 7.62 (s, 1H), 7.54-7.51 (m, 2H), 7.36 (d, 1H), 3.82 (s, 3H).

Synthesis of benzo[b]triphenyleno[2,3-d]thiophen-6-ol

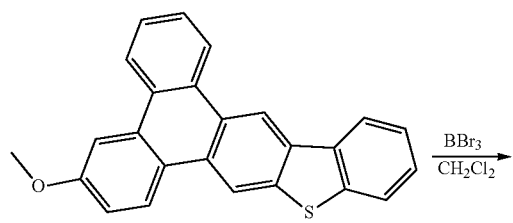

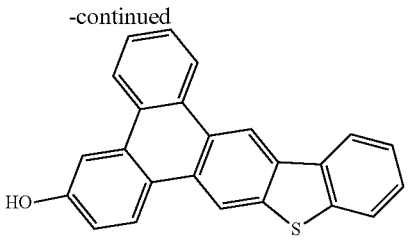

The compound 6-methoxybenzo[b]triphenyleno[2,3-d]-thiophene (10 g, 27.4 mmol) was mixed with 400 ml of CH₂Cl₂. To the mixture, 8.25 g of BBr₃ (32.9 mmol) was added and the mixture was stirred overnight. After the reaction finished, the solvent was removed under reduced pressure, and the crude product was purified by column chromatography, yielding 8.8 g of benzo[b]triphenyleno[2,3-d]thiophen-6-ol as white solid (91.5%). ¹H NMR (CDCl₃, 400 MHz): chemical shift (ppm) 8.89-8.87 (m, 2H), 8.78 (d, 1H), 8.45 (d, 1H), 8.09 (m, 2H), 7.94 (d, H), 7.86-7.83 (m, 2H), 7.58 (s, 1H), 7.51-7.48 (m, 2H), 7.31 (d, 1H), 5.41 (s, 1H).

Synthesis of benzo[b]triphenyleno[2,3-d]thiophen-6-yl trifluoro-methanesulfonate

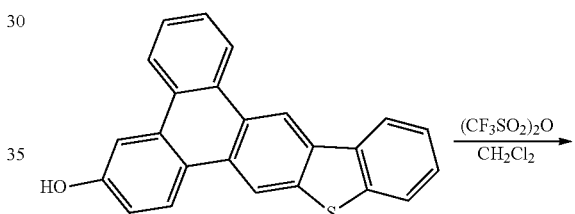

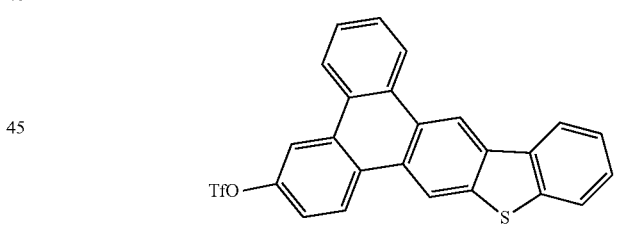

The compound benzo[b]triphenyleno[2,3-d]thiophen-6-ol (10 g, 28.5 mmol) was mixed with 450 ml of CH₂Cl₂. To the mixture, 3.4 g of pyridine (42.8 mmol) was added and the mixture was stirred for 1 hrs. To the mixture, 13.7 g of (CF₃SO₂)₂O (48.5 mmol) was added and the mixture was stirred for 1 hrs. After the reaction finished, the solvent was removed under reduced pressure, and the crude product was purified by column chromatography, yielding 10.5 g of benzo[b]triphenyleno[2,3-d]thiophen-6-yl trifluoro-methanesulfonate as yellow solid (55.9%). ¹H NMR (CDCl₃, 400 MHz): chemical shift (ppm) 8.99-8.95 (m, 3H), 8.47 (d, 1H), 8.14-8.11 (m, 3H), 7.97 (d, H), 7.88-7.85 (m, 2H), 7.58 (s, 1H), 7.53-7.51 (m, 2H).

Synthesis of 2-(benzo[b]triphenyleno[2,3-d]thiophen-6-yl)-4,4,5,5-tetramethyl-1,3,2-dioxaborolane

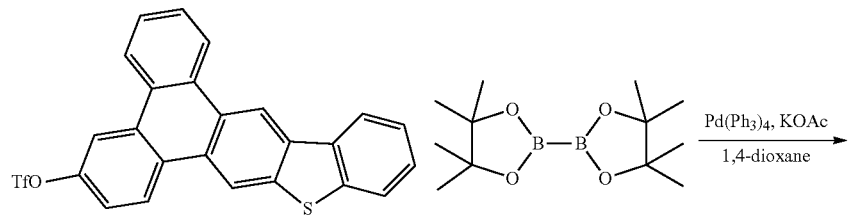

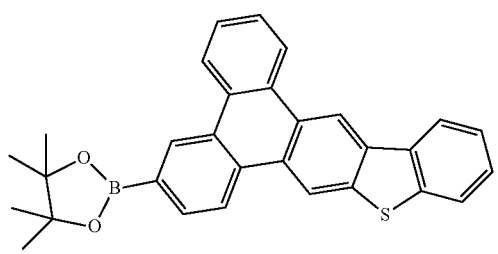

A mixture of 5 g (10.4 mmol) of benzo[b]triphenyleno[2,3-d]thiophen-6-yl trifluoromethanesulfonate, 3.16 g (12.4 mmol) of bis(pinacolato)diboron, 0.48 g (0.4 mmol) of Pd(Ph$_3$)$_4$, 2.04 g (20.8 mmol) of potassium acetate, and 60 ml of 1,4-dioxane was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 3.1 g of 2-(benzo[b]triphenyleno[2,3-d]thiophen-6-yl)-4,4,5,5-tetramethyl-1,3,2-dioxaborolane as white solid (65%). $^1$H NMR (CDCl$_3$, 400 MHz): chemical shift (ppm) 8.94-8.88 (m, 3H), 8.47 (d, 1H), 8.15-8.12 (m, 3H), 7.99 (d, 1H), 7.87-7.84 (m, 3H), 7.54-7.52 (m, 2H), 1.27 (s, 12H).

Synthesis of 6-(10-phenylanthracen-9-yl)benzo[b]triphenyleno-[2,3-d]thiophene (Compound 5)

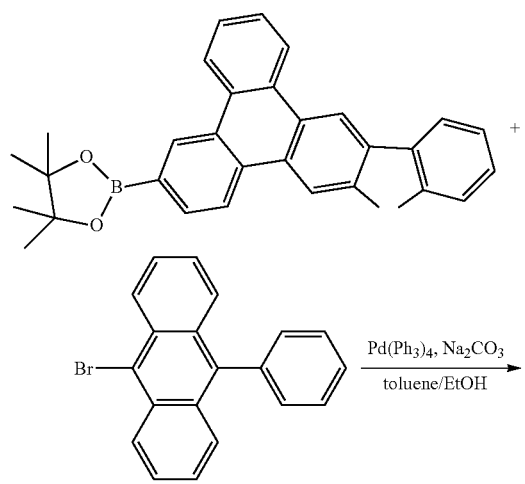

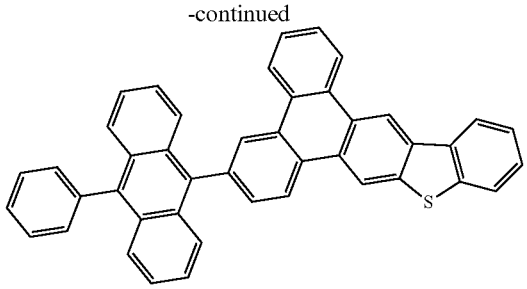

-continued

A mixture of 3 g (6.51 mmol) of 2-(benzo[b]triphenyleno[2,3-d]-thiophen-6-yl)-4,4,5,5-tetramethyl-1,3,2-dioxaborolane, 2.4 g (7.17 mmol) of 9-bromo-10-phenylanthracene, 0.15 g (0.13 mmol) of Pd(Ph$_3$)$_4$, 6.5 ml of 2M Na$_2$CO$_3$, 20 ml of EtOH and 40 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 2.5 g of 6-(10-phenylanthracen-9-yl)benzo[b]triphenyleno-[2,3-d]thiophene as yellow solid (65.4%). $^1$H NMR (CDCl$_3$, 400 MHz): chemical shift (ppm) 8.94-8.89 (m, 3H), 8.47 (d, 1H), 8.34 (s, 1H), 8.13-8.08 (m, 3H), 7.96-7.92 (m, 5H), 7.86-7.83 (m, 2H), 7.52-7.45 (m, 6H), 7.41-7.35 (m, 5H).

Example 19-35

We have used the same synthesis methods to get a series of intermediates and the following compounds are synthesized analogously.

| Ex. | Intermediate III | Intermediate IV | Product | Yield |
|---|---|---|---|---|
| 19 | | | Compound 2 | 63% |
| 20 | | | Compound 3 | 64% |
| 21 | | | Compound 10 | 57% |

-continued

| Ex. | Intermediate III | Intermediate IV | Product | Yield |
|---|---|---|---|---|
| 22 | | | Compound 14 | 59% |
| 23 | | | Compound 17 | 52% |
| 24 | | | Compound 38 | 58% |

| Ex. | Intermediate III | Intermediate IV | Product | Yield |
|---|---|---|---|---|
| 25 | | | Compound 47 | 66% |
| 26 | | | Compound 56 | 63% |
| 27 | | | Compound 86 | 60% |

-continued
| Ex. | Intermediate III | Intermediate IV | Product | Yield |
|---|---|---|---|---|
| 28 | 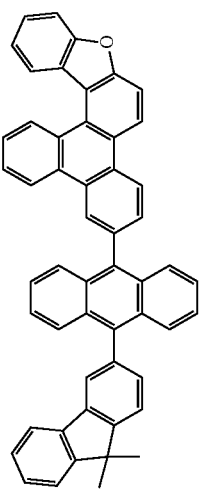 | 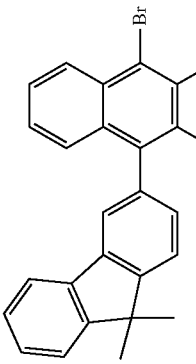 | 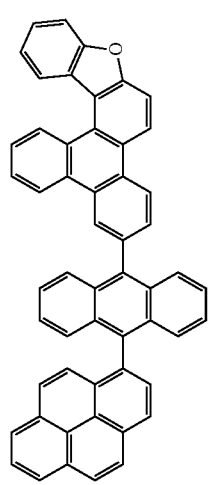 Compound 87 | 57% |
| 29 | 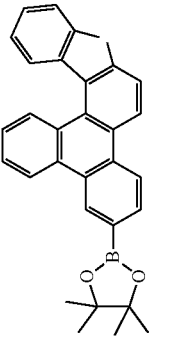 | 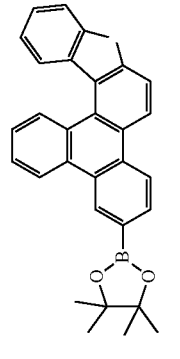 | 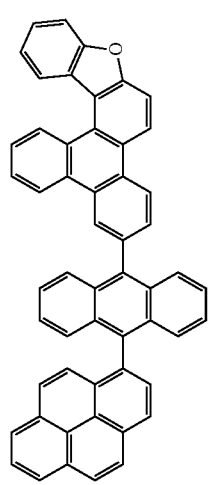 Compound 109 | 51% |
| 30 | 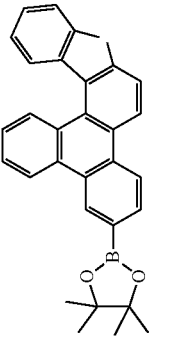 | 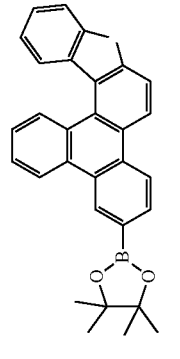 | 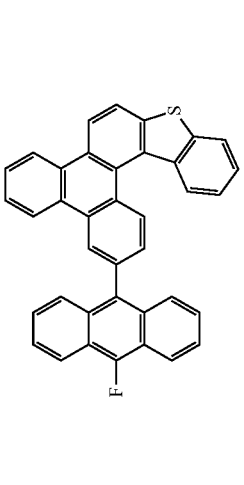 Compound 134 | 55% |

-continued

| Ex. | Intermediate III | Intermediate IV | Product | Yield |
|---|---|---|---|---|
| 31 | | | Compound 135 | 49% |
| 32 | | | Compound 138 | 59% |
| 33 | | | Compound 141 | 52% |

-continued

| Ex. | Intermediate III | Intermediate IV | Product | Yield |
|---|---|---|---|---|
| 34 | | | Compound 144 | 57% |
| 35 | | | Compound 149 | 48% |

General Method of Producing Organic EL Device

ITO-coated glasses with 9~12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1-0.3 nm/sec) are precisely monitored or set with the aid of a quartz-crystal monitor. It is also possible, as described above, for individual layers to consist of more than one compound, i.e. in general a host material doped with a dopant material and/or co-deposited with a co-host. This is successfully achieved by co-vaporization from two or more sources, which means the triphenylenobenzofuran and triphenylenobenzothiophene derivatives of the present invention are thermally stable.

Dipyrazino[2,3-f:2,3-]quinoxaline-2,3,6,7,10,11-hexacarbonitrile(HA T-CN) is used as hole injection layer in this organic EL device. N,N-Bis(naphthalene-1-yl)-N,N-bis (phenyl)-benzidine (NPB) is most widely used as the hole transporting layer. 10,10-dimethyl-13-(3-(pyren-1-yl)-phenyl)-10H-indeno[2,1-b]triphenylene (H1) and 10,10-dimethyl-13-(10-(3-(naphthalen-2-yl)phenyl)anthracen-9-yl)-10H-indeno-[2,1-b]triphenylene (H2) are used as emitting hosts for comparison, and N1,N1,N6,N6-tetra-m-tolylpyrene-1,6-diamine (D1) is used as blue guest in the emitting layer. HB3 (see the following chemical structure) is used as hole blocking material (HBM), and 2-(naphthalen-1-yl)-9-(4-(1-(4-(10-(naphthalene-2-yl)anthracen-9-yl)-phenyl)-1H-benzo[d]imidazol-2-yl)phenyl)-1,10-phenanthroline (ET2) is used as electron transporting material to co-deposit with 8-hydroxyquinolato-lithium (LiQ) in organic EL devices. The chemical structures of conventional OLED materials and the exemplary organic compounds of the present invention for producing control and exemplary organic EL devices in this invention are shown as follows:

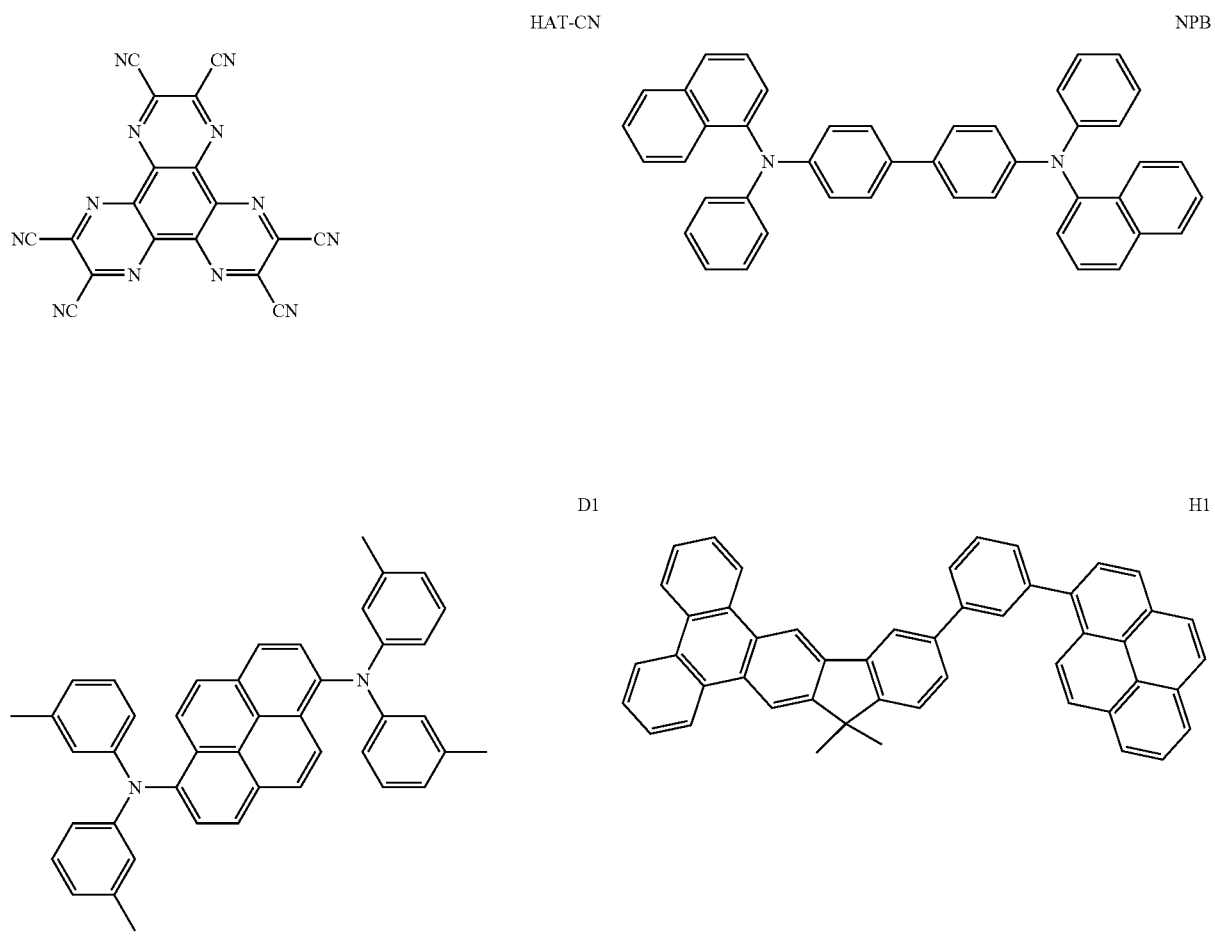

-continued
H2
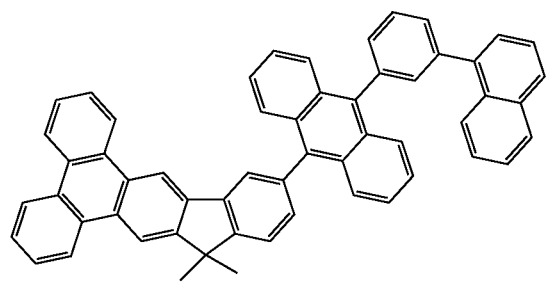
HB3
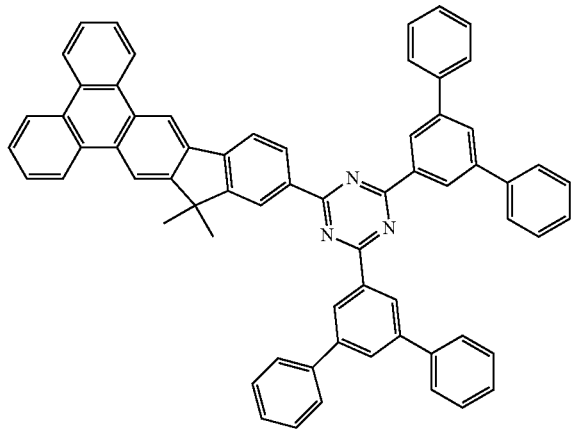
ET2
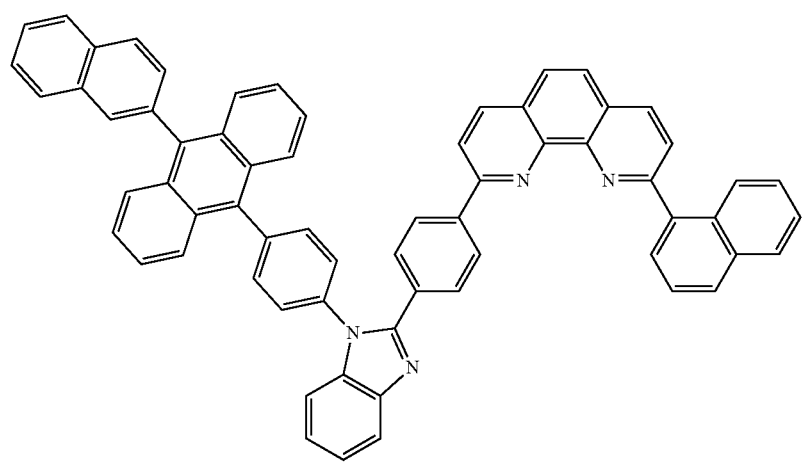
Compound 2
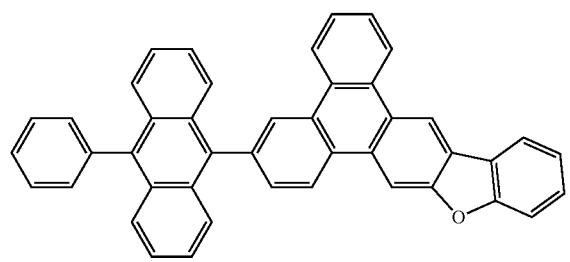
Compound 5
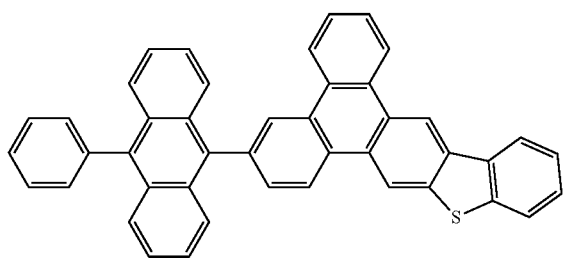
Compound 10
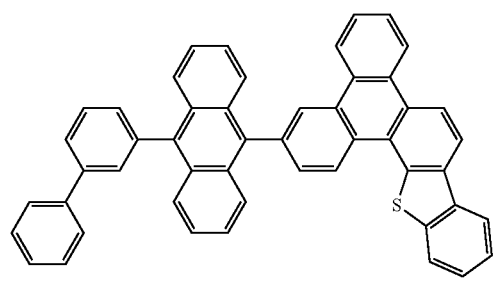
Compound 14
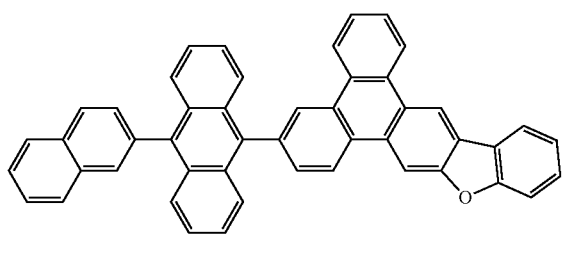

-continued
Compound 17
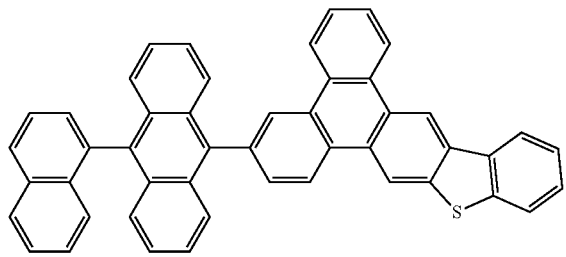
Compound 20
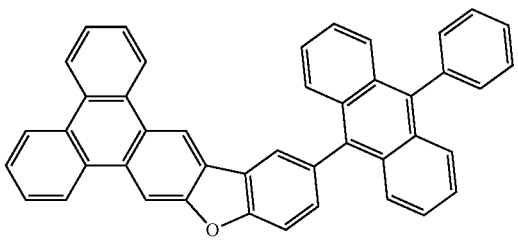
Compound 26
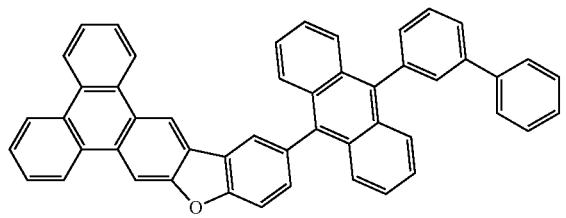
Compound 35
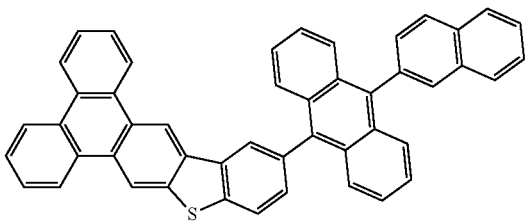
Compound 38
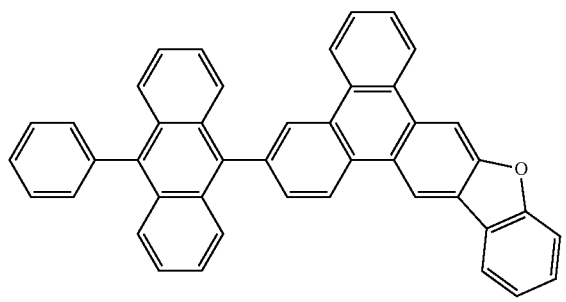
Compound 69
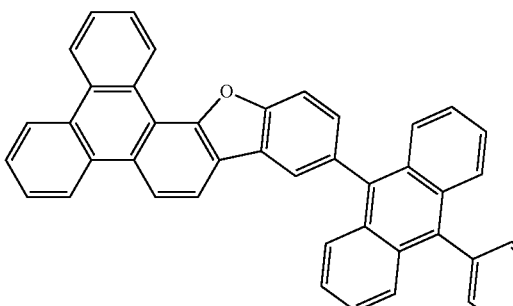
Compound 85
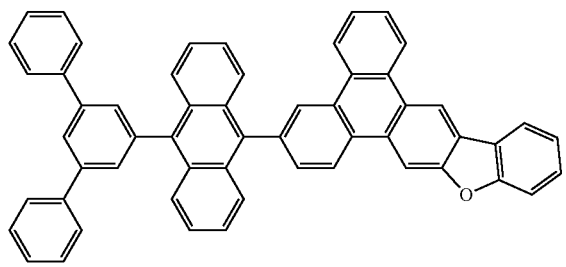
Compound 87
Compound 98
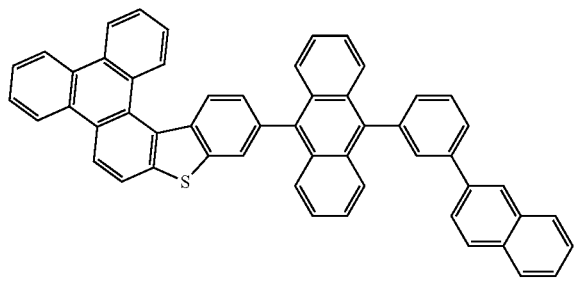
Compound 109
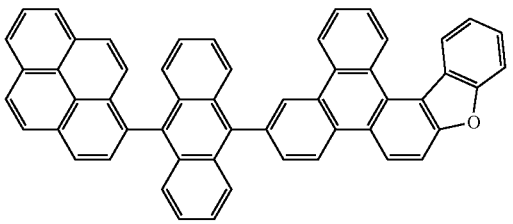

-continued
Compound 121
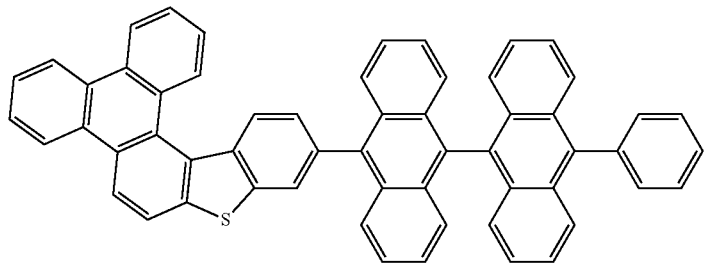
Compound 130
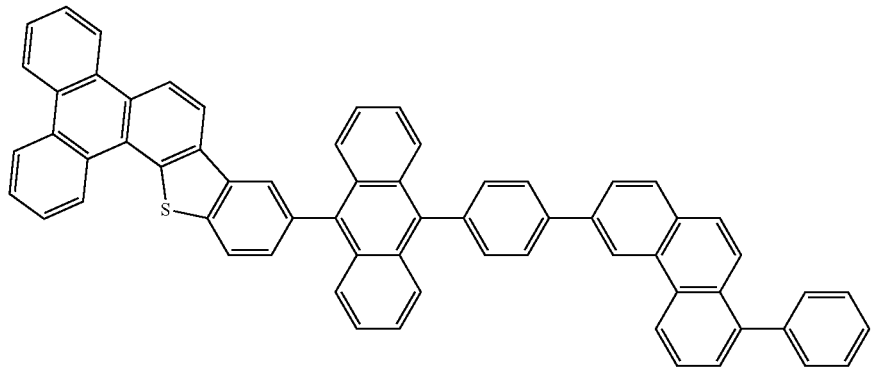
Compound 134
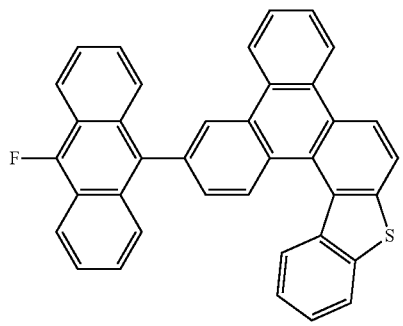
Compound 135
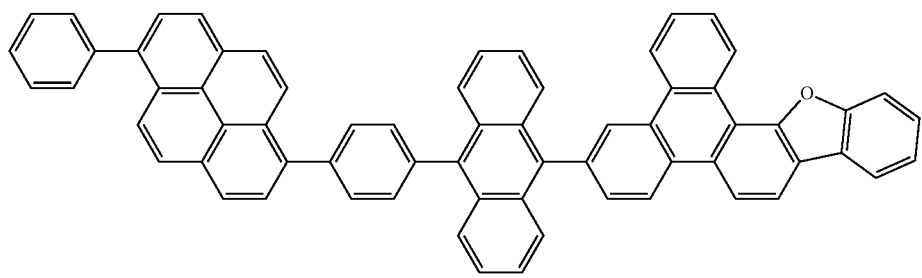
Compound 138
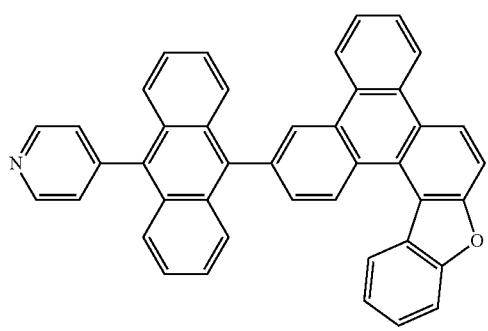
Compound 141
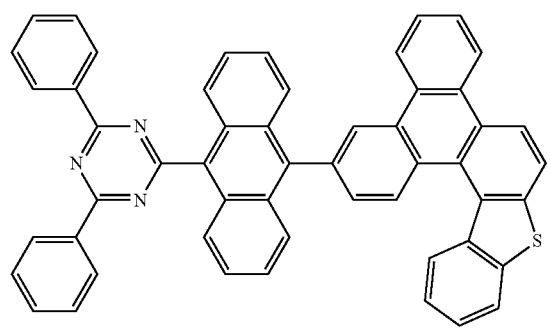

Compound 151
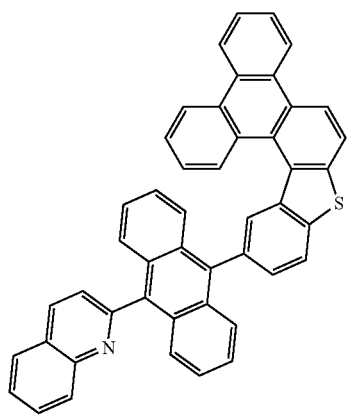
Compound 152
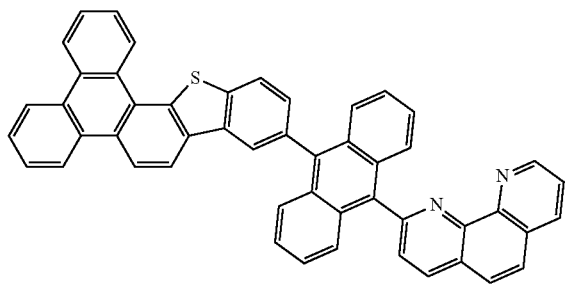
Compound 163
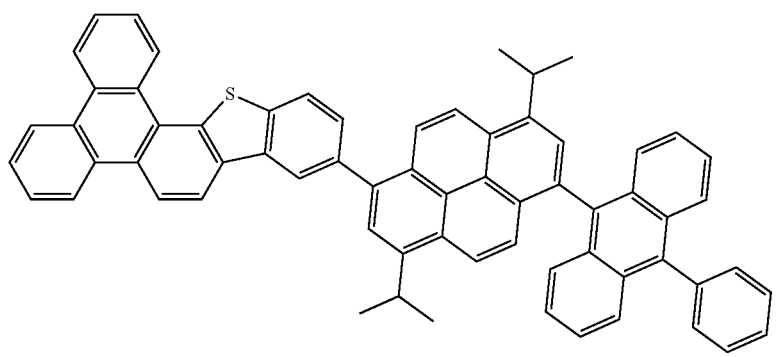 [SMILES: CC(C)c1cc(-c2ccc3sc4c(ccc5c6ccccc6c6ccccc6c54)c3c2)c2ccc3c(C(C)C)cc(-c4c5ccccc5c(-c5ccccc5)c5ccccc45)c4ccc1c2c43]
Compound 165
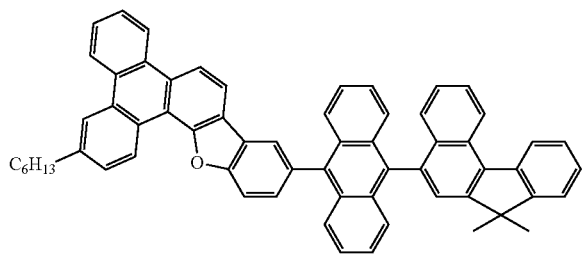
Compound 168
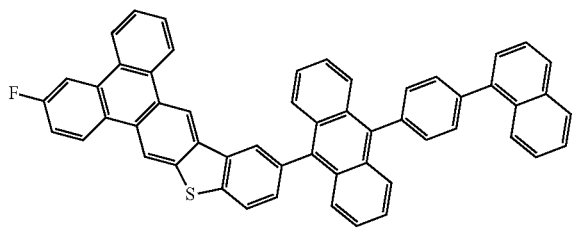
Compound 169
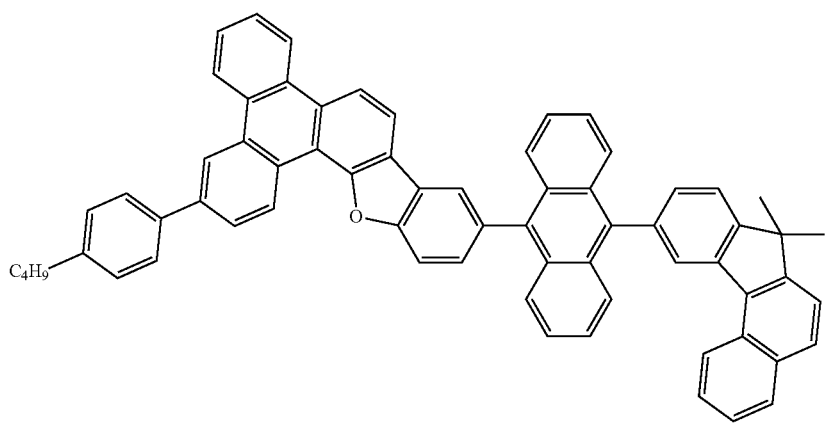

-continued

Compound 171

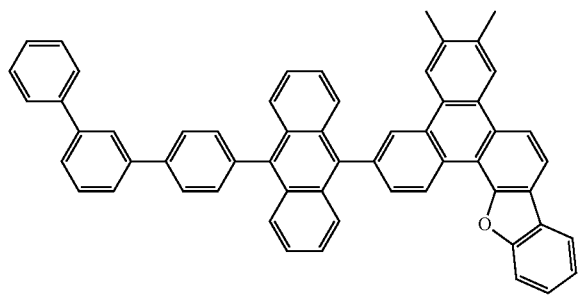

Compound 173

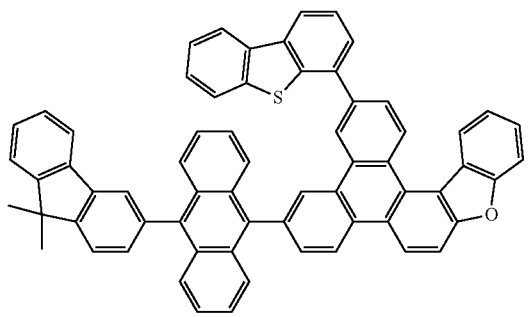

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

Example 36

Using a procedure analogous to the above mentioned general method, organic EL devices emitting blue light and having the following device structure as shown in the FIGURE were produced: ITO/HAT-CN (20 nm)/NPB (110 nm)/Emitting host doped with 5% Emitting guest (30 nm)/HB3/ET2 doped 50% LiQ (35 nm)/LiQ (1 nm)/Al (160 nm). In the device illustrated in the FIGURE, the hole injection layer 20 is deposited onto the transparent electrode 10, the hole transport layer 30 is deposited onto the hole injection layer 20, the emitting layer 40 is deposited onto the hole transport layer 30, the hole blocking layer 50 is deposited onto the emitting layer 40, the electron transport layer 60 is deposited onto the hole blocking layer 50, the electron injection layer 70 is deposited onto the electron transport layer 60, and the metal electrode 80 is deposited onto the electron injection layer 70. The I-V-B (at 1000 nits) test reports of these organic EL devices are summarized in Table 1 below. The half-life time is defined as the time the initial luminance of 1000 $cd/m^2$ has dropped to half.

TABLE 1

| Emitting Host | Emitting Guest | Voltage (V) | Yield (cd/A) | CIE(y) | Half-life time (hour) |
|---|---|---|---|---|---|
| H1 | D1 | 4.4 | 4.5 | 0.181 | 240 |
| H2 | D1 | 4.3 | 4.6 | 0.182 | 250 |
| Compound 2 | D1 | 2.6 | 6.9 | 0.179 | 680 |
| Compound 5 | D1 | 2.7 | 6.8 | 0.180 | 660 |
| Compound 10 | D1 | 2.9 | 6.9 | 0.181 | 650 |

TABLE 1-continued

| Emitting Host | Emitting Guest | Voltage (V) | Yield (cd/A) | CIE(y) | Half-life time (hour) |
|---|---|---|---|---|---|
| Compound 14 | D1 | 3.2 | 7.0 | 0.181 | 600 |
| Compound 17 | D1 | 3.0 | 6.5 | 0.180 | 620 |
| Compound 20 | D1 | 2.8 | 6.4 | 0.179 | 670 |
| Compound 26 | D1 | 3.1 | 6.6 | 0.182 | 630 |
| Compound 35 | D1 | 3.0 | 6.7 | 0.178 | 650 |
| Compound 38 | D1 | 2.7 | 6.8 | 0.182 | 670 |
| Compound 69 | D1 | 3.1 | 6.4 | 0.181 | 590 |
| Compound 86 | D1 | 3.4 | 6.2 | 0.183 | 510 |
| Compound 87 | D1 | 3.5 | 6.0 | 0.182 | 480 |
| Compound 98 | D1 | 3.2 | 6.5 | 0.181 | 550 |
| Compound 109 | D1 | 3.6 | 6.1 | 0.179 | 520 |
| Compound 121 | D1 | 3.3 | 5.9 | 0.178 | 490 |
| Compound 130 | D1 | 3.4 | 6.0 | 0.180 | 470 |
| Compound 134 | D1 | 4.2 | 4.8 | 0.176 | 290 |
| Compound 135 | D1 | 3.7 | 5.8 | 0.179 | 430 |
| Compound 138 | D1 | 4.1 | 4.9 | 0.177 | 310 |
| Compound 141 | D1 | 3.5 | 6.1 | 0.182 | 460 |
| Compound 151 | D1 | 4.1 | 5.4 | 0.178 | 340 |
| Compound 152 | D1 | 4.1 | 5.2 | 0.178 | 320 |
| Compound 163 | D1 | 4.0 | 5.1 | 0.177 | 300 |
| Compound 165 | D1 | 3.6 | 5.5 | 0.182 | 450 |
| Compound 168 | D1 | 3.4 | 5.3 | 0.180 | 460 |
| Compound 169 | D1 | 3.8 | 5.9 | 0.179 | 420 |
| Compound 171 | D1 | 3.7 | 5.7 | 0.181 | 390 |
| Compound 173 | D1 | 3.9 | 5.4 | 0.178 | 360 |

In the above test report of organic EL devices (see Table 1), we show that the organic material with formula(A) used as emitting host material for organic EL devices in the present invention displays better performance than the prior art organic EL materials. More specifically, the organic EL devices of the present invention use the organic material with formula (A) as emitting host material to collocate with emitting guest material, such as D1, showing lower power consumption, higher efficiency, and longer half-life time.

To sum up, the present invention discloses an organic compound, which can be used as the fluorescent host material of the light emitting layer in organic EL devices. The mentioned organic compound is represented by the following formula (A):

What is claimed is:

1. An organic compound of formula (A) below:

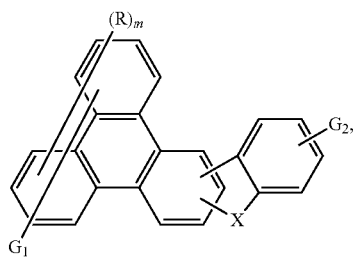

formula (A)

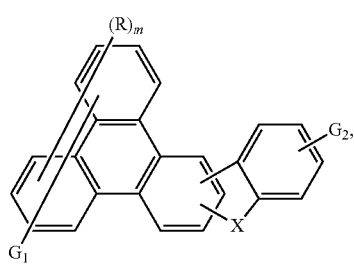

wherein at least one of $G_1$ and $G_2$ exists and represents formula (B) below:

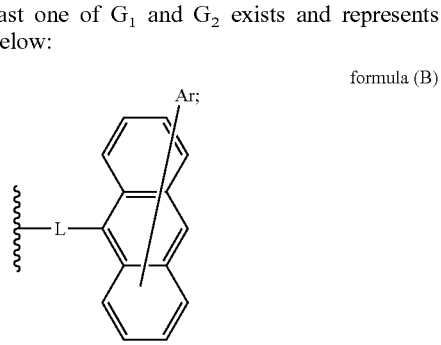

formula (B)

X is a divalent bridge selected from the group consisting of O and S; m is an integer of 0 to 8; L represents a single bond, a substituted or unsubstituted divalent arylene group having 6 to 30 ring carbon atoms, or a substituted or unsubstituted divalent heteroarylene group having 6 to 30 ring carbon atoms; Ar represents a halogen, a substituted or unsubstituted aryl group having 6 to 30 carbon atoms, or a substituted or unsubstituted heteroaryl group having 3 to 30 carbon atoms; and R represents a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms.

wherein at least one of $G_1$ and $G_2$ exists and represents formula (B) having a 9-anthryl below:

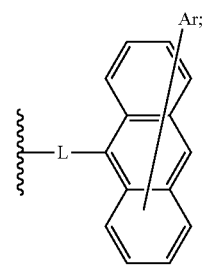

formula (B)

X is a divalent bridge selected from the group consisting of O and S; m is an integer of 0 to 8; L represents a single bond, a substituted or unsubstituted divalent arylene group having 6 to 30 ring carbon atoms, or a substituted or unsubstituted divalent heteroarylene group having 6 to 30 ring carbon atoms; Ar represents a halogen, a substituted or unsubstituted aryl group having 6 to 30 carbon atoms, or a substituted or unsubstituted heteroaryl group having 3 to 30 carbon atoms; and R represents a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms.

2. The organic compound according to claim 1, wherein the organic compound is represented by one of the following formula (1) to formula (12):

formula (1)

formula (2)

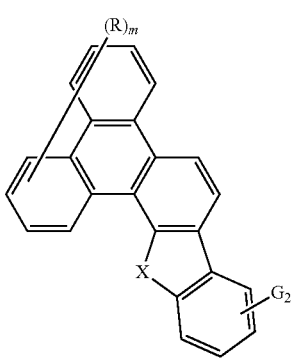

formula (3)
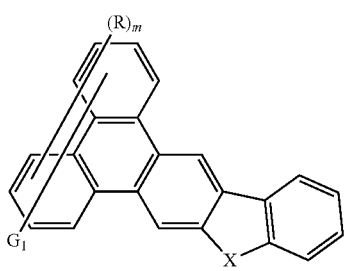
formula (4)
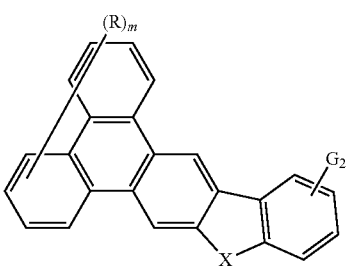
formula (5)
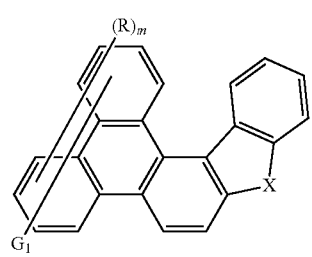
formula (6)
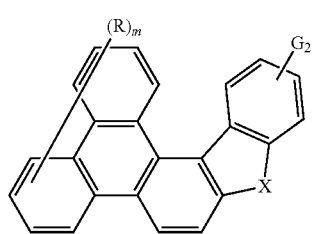
formula (7)
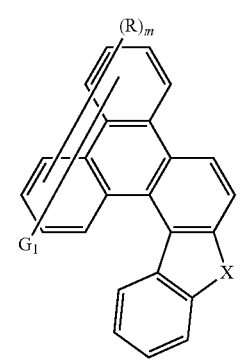
formula (8)
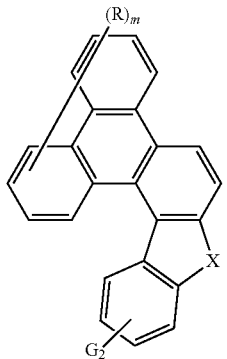
formula (9)
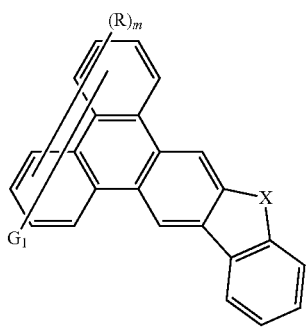
formula (10)
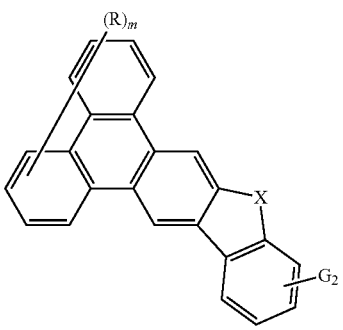
formula (11)
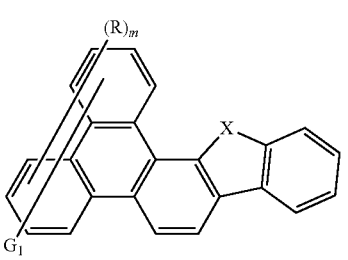
and
formula (12)
3. The organic compound according to claim 1, wherein the alkyl group, aralkyl group, aryl group, or heteroaryl group is substituted by a halogen, an alkyl group, an aryl group, or a heteroaryl group.

4. The organic compound according to claim 1, wherein Ar represents a substituted or unsubstituted phenyl group, a substituted or unsubstituted biphenyl group, a substituted or unsubstituted terphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, or a substituted or unsubstituted chrysenyl group.

5. The organic compound according to claim 1, wherein Ar represents one of the following substituents:

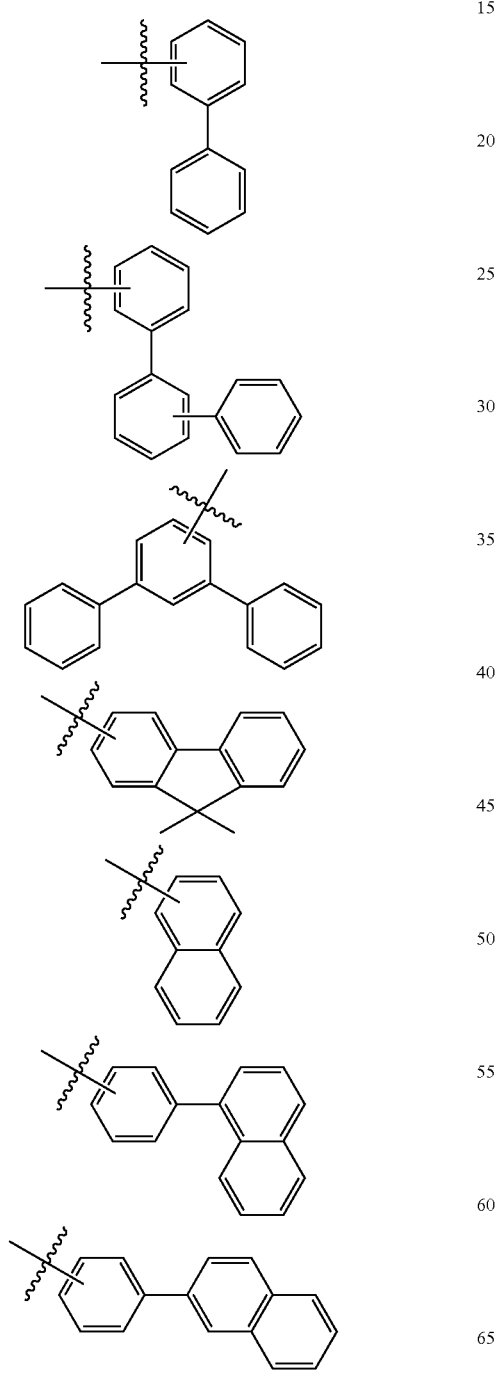

-continued

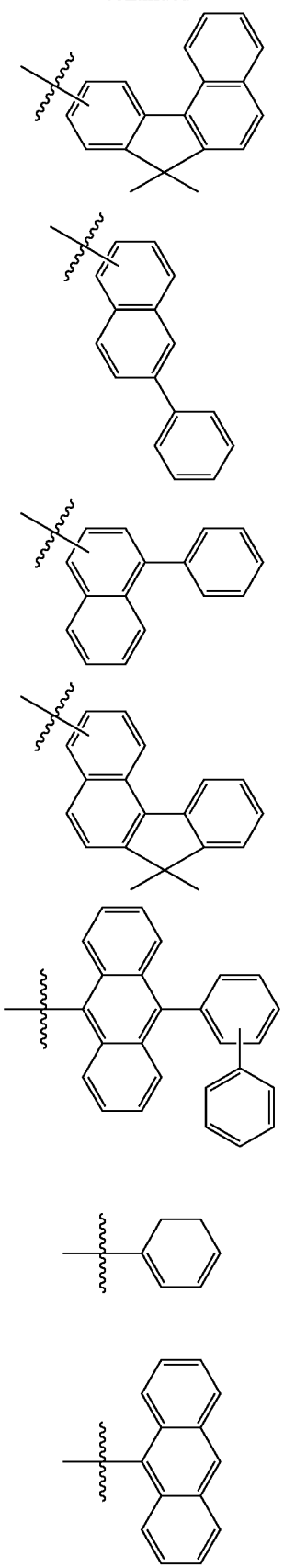

111
-continued
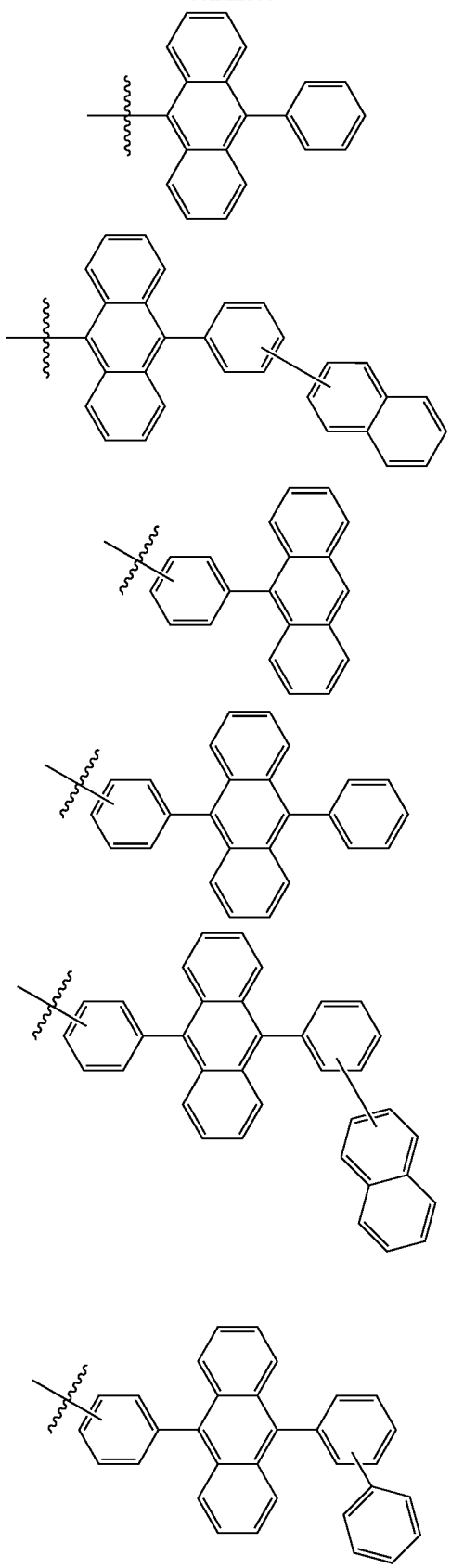
112
-continued
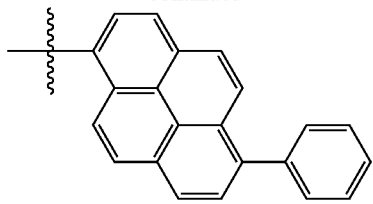
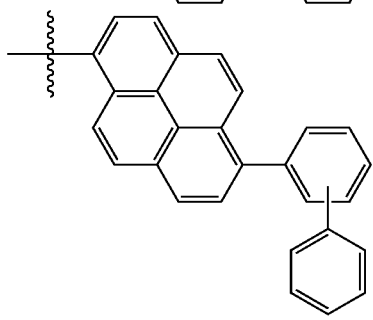
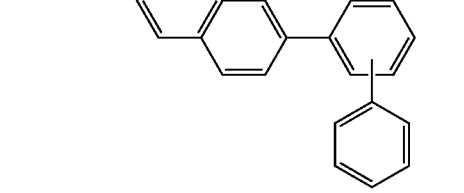
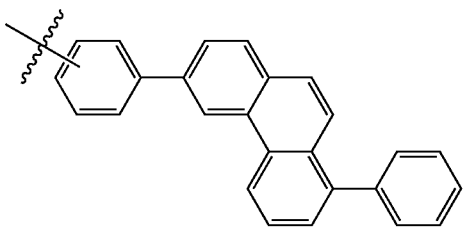
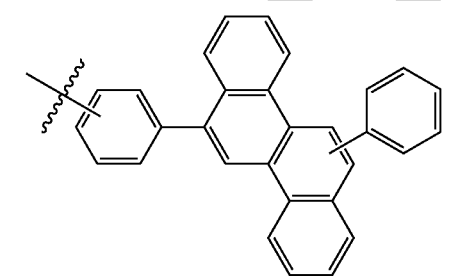
6. An organic compound is one of the following compounds:

Compound 1
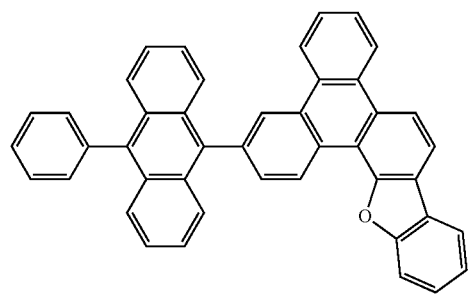
Compound 2
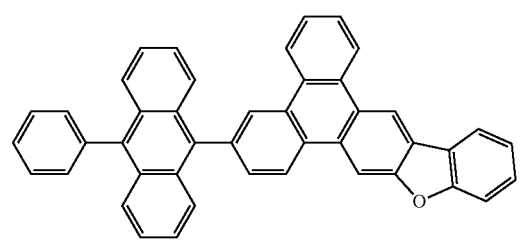 [SMILES: c1ccc(-c2c3ccccc3c(-c3ccc4c(c3)c3ccccc3c3cc5c(cc43)oc3ccccc35)c3ccccc23)cc1]
Compound 3
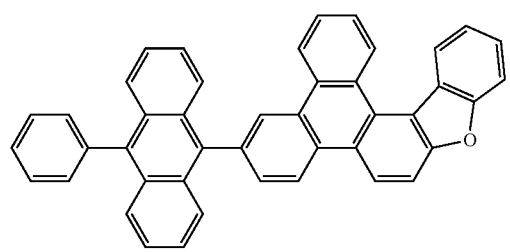
Compound 4
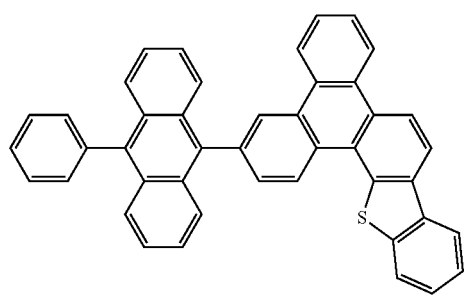
Compound 5
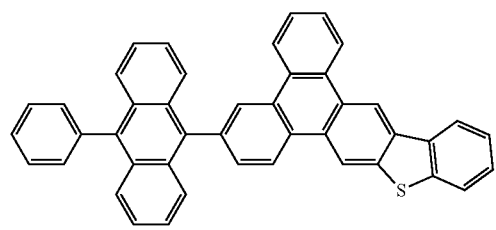
Compound 6
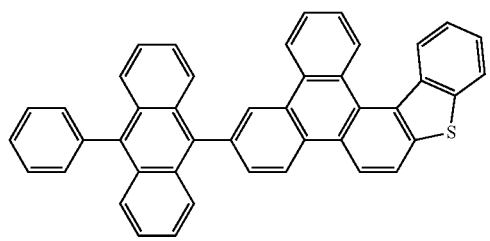 [SMILES: c1ccc(-c2c3ccccc3c(-c3ccc4c(c3)c3ccccc3c3c4ccc4oc5ccccc5c43)c3ccccc23)cc1]
Compound 7
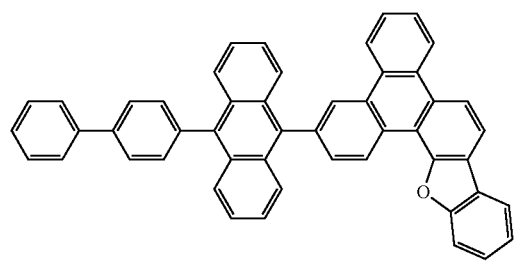
Compound 8
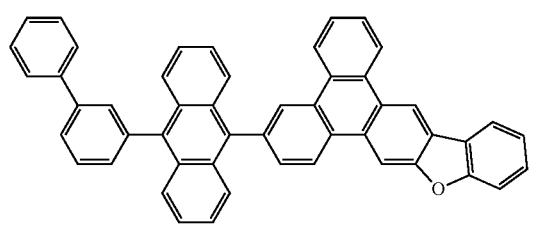

-continued
Compound 9
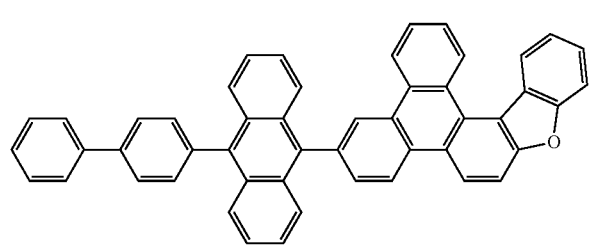
Compound 10
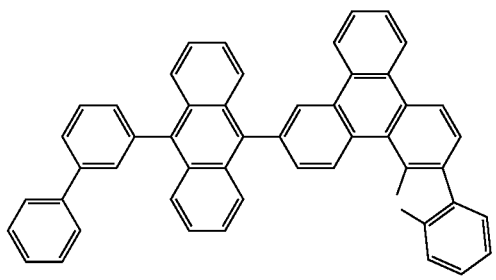 [SMILES: c1ccc(-c2cccc(-c3c4ccccc4c(-c4ccc5c(c4)c4ccccc4c4ccc6c7ccccc7sc6c45)c4ccccc34)c2)cc1]
Compound 11
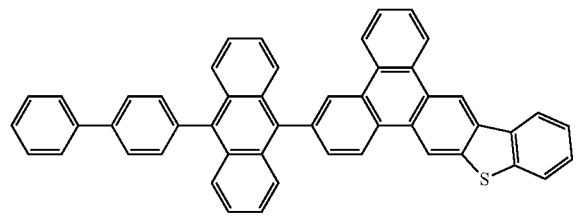
Compound 12
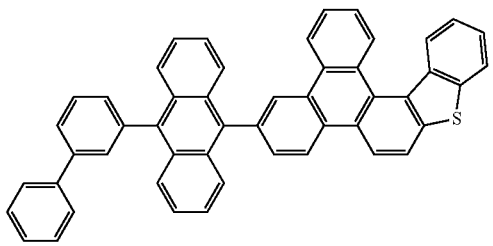
Compound 13
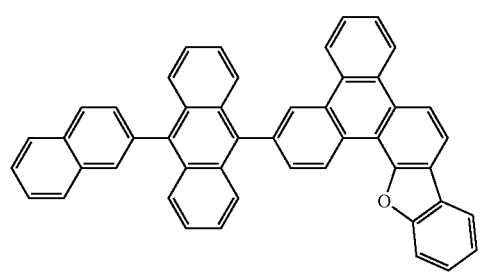
Compound 14
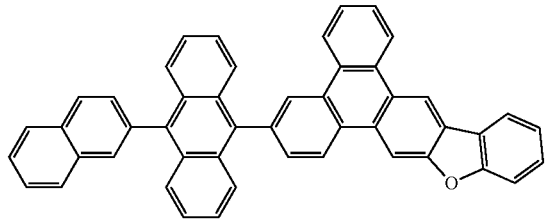 [SMILES: c1ccc2cc(-c3c4ccccc4c(-c4ccc5c(c4)c4ccccc4c4cc6c(cc54)oc4ccccc46)c4ccccc34)ccc2c1]
Compound 15
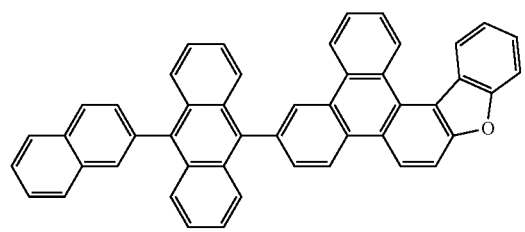
Compound 16
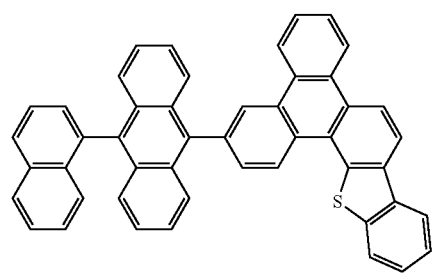

-continued
Compound 17
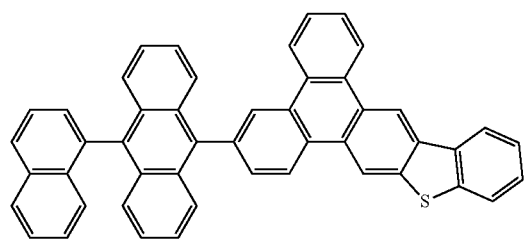 [SMILES: c1ccc2c(-c3c4ccccc4c(-c4ccc5c(c4)c4ccccc4c4cc6c(cc54)sc4ccccc46)c4ccccc34)cccc2c1]
Compound 18
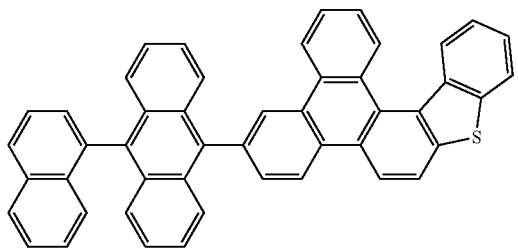
Compound 19
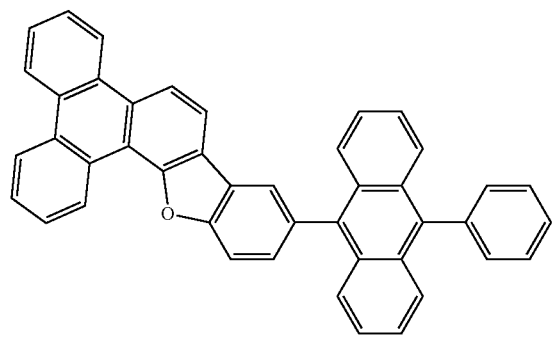
Compound 20
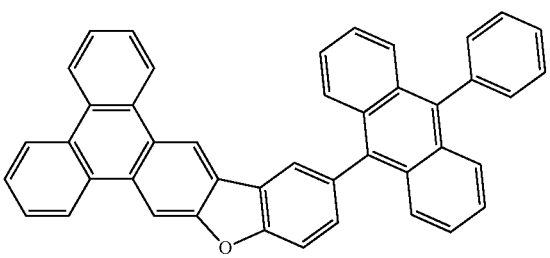
Compound 21
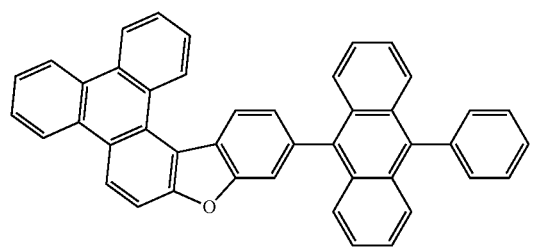
Compound 22
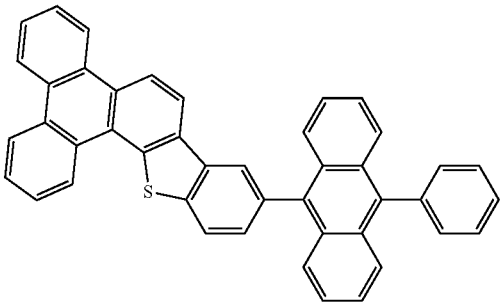
Compound 23
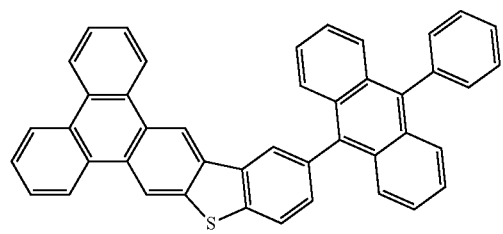
Compound 24
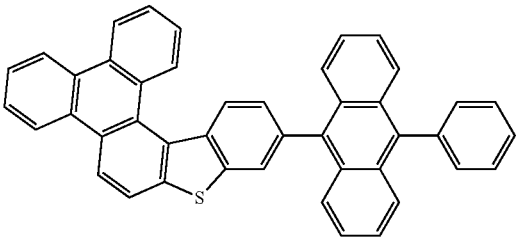
Compound 25
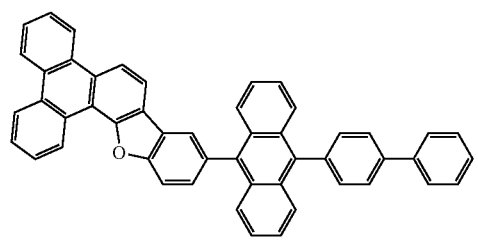
Compound 26
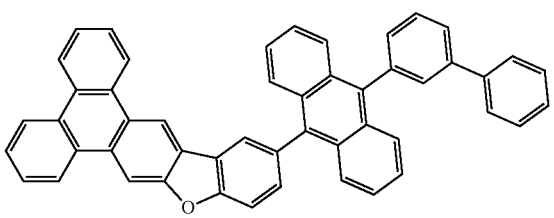

-continued
Compound 27
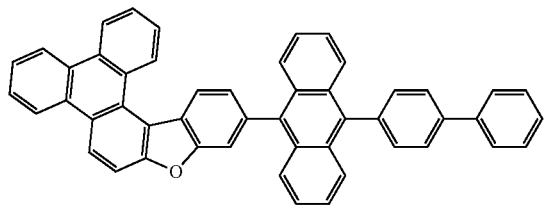
Compound 28
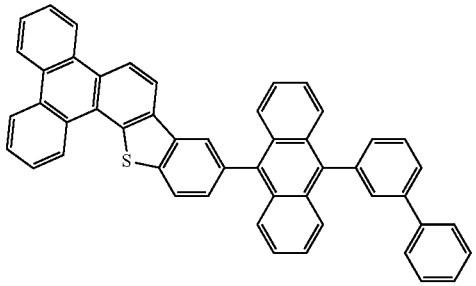
Compound 29
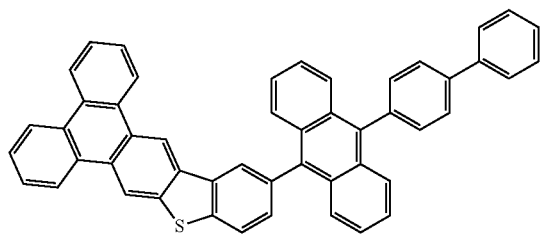
Compound 30
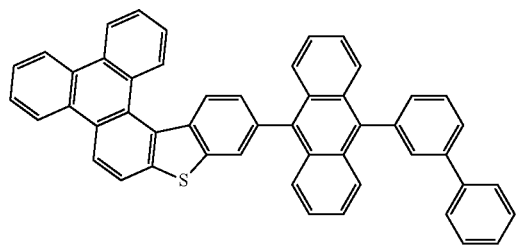
Compound 31
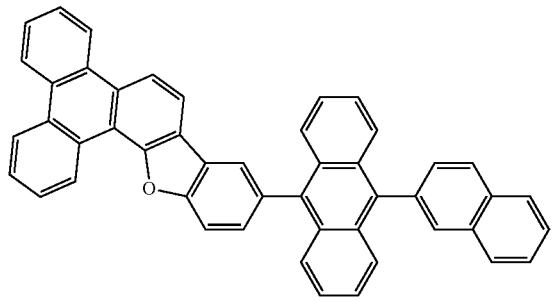
Compound 32
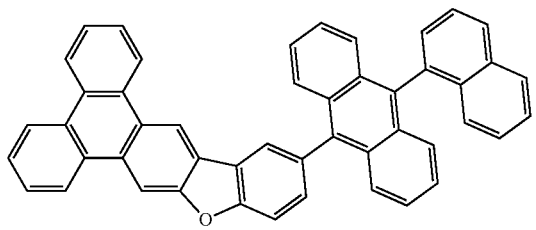
Compound 33
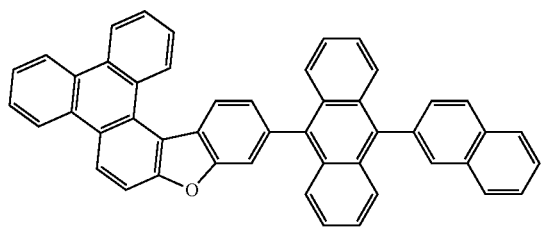
Compound 34
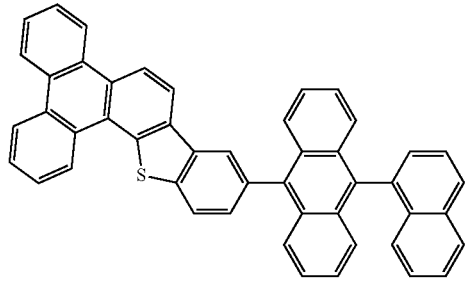

-continued
Compound 35
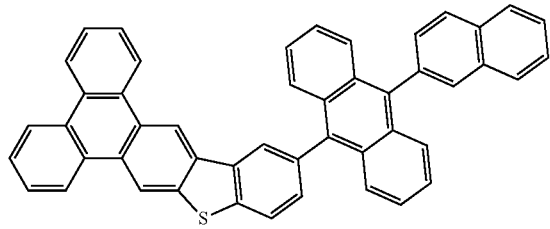
Compound 36
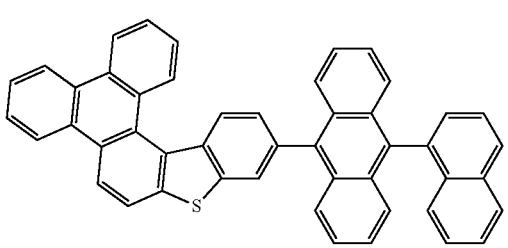
Compound 37
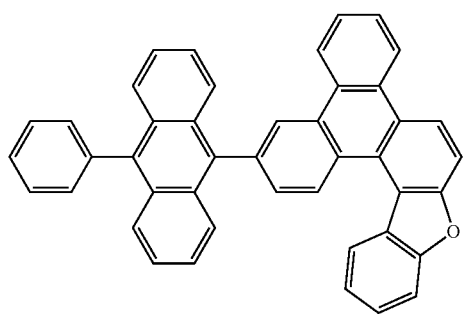
Compound 38
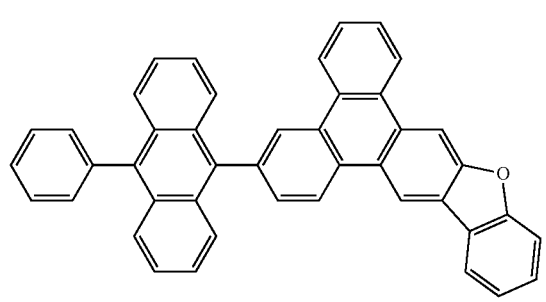 [SMILES: c1ccc(-c2c3ccccc3c(-c3ccc4c(c3)c3ccccc3c3cc5oc6ccccc6c5cc43)c3ccccc23)cc1]
Compound 39
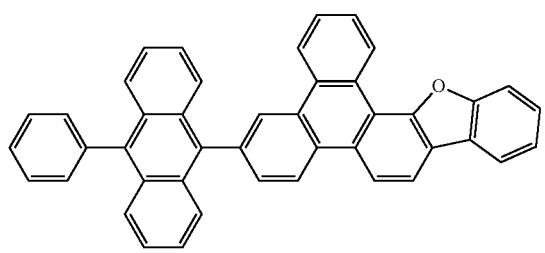
Compound 40
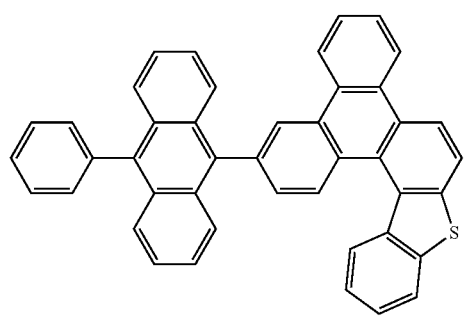
Compound 41
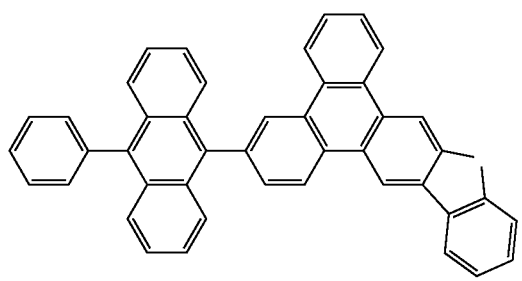
Compound 42
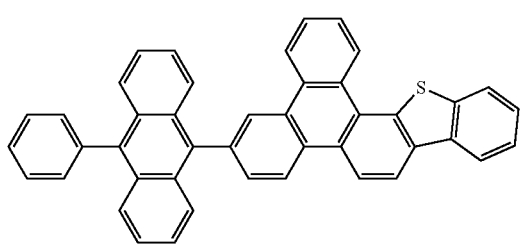

-continued
Compound 43
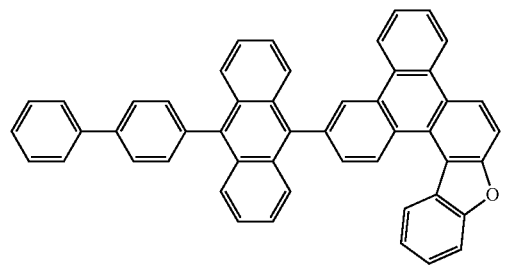
Compound 44
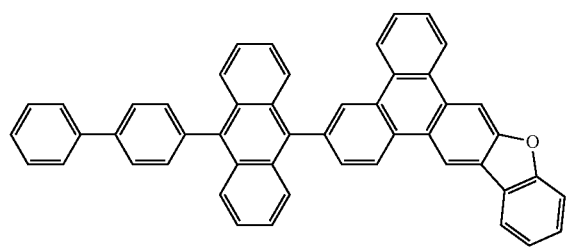
Compound 45
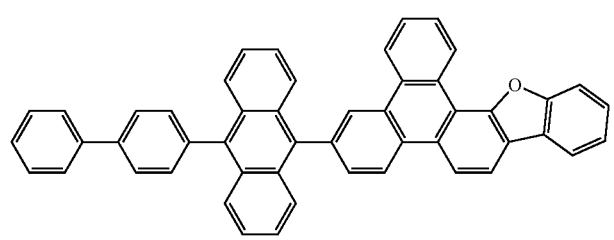
Compound 46
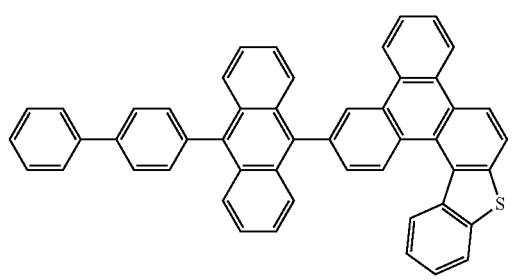
Compound 47
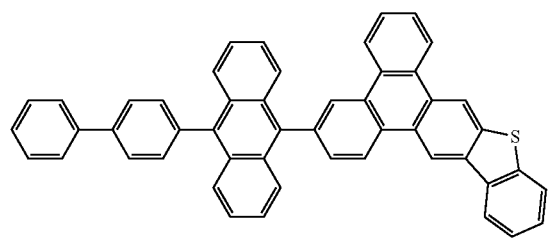 [SMILES: c1ccc(-c2ccc(-c3c4ccccc4c(-c4ccc5c(c4)c4ccccc4c4cc6sc7ccccc7c6cc54)c4ccccc34)cc2)cc1]
Compound 48
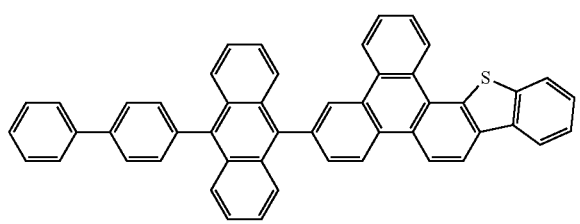
Compound 49
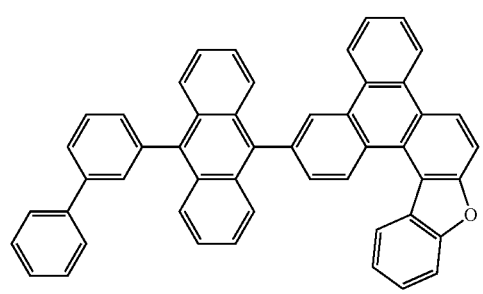
Compound 48
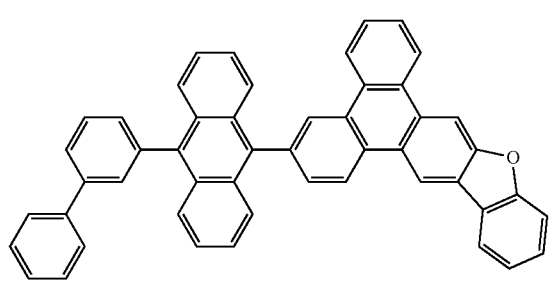
Compound 47
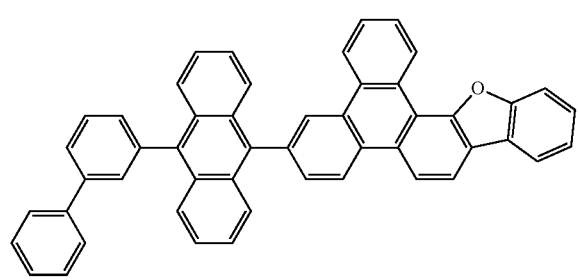
Compound 46
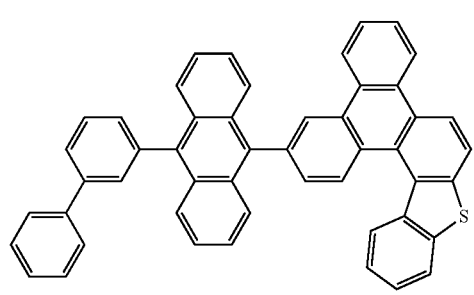

-continued
Compound 53
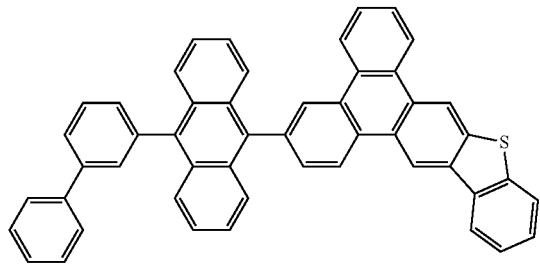
Compound 54
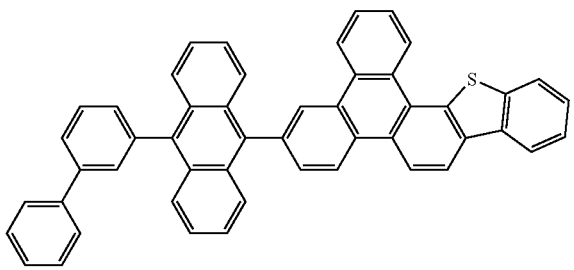
Compound 55
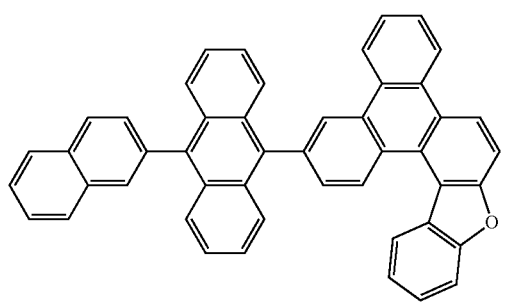
Compound 56
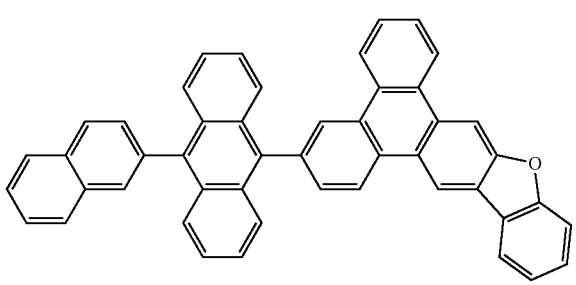 [SMILES: c1ccc2cc(-c3c4ccccc4c(-c4ccc5c(c4)c4ccccc4c4cc6oc7ccccc7c6cc54)c4ccccc34)ccc2c1]
Compound 57
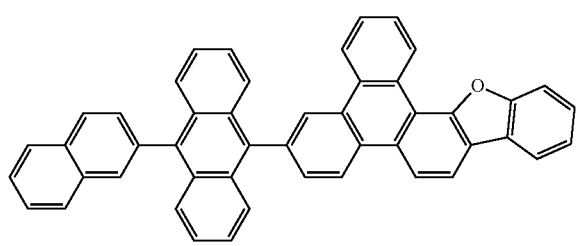
Compound 58
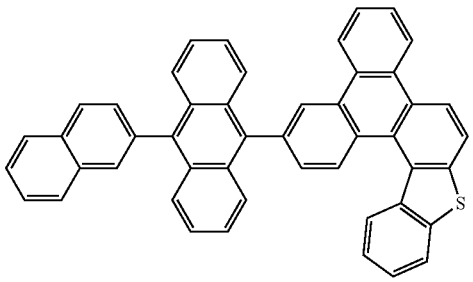
Compound 59
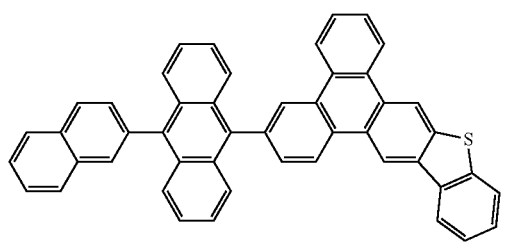
Compound 60
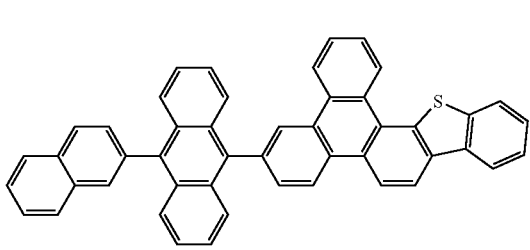
Compound 61
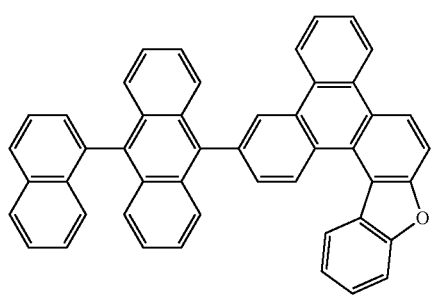
Compound 62
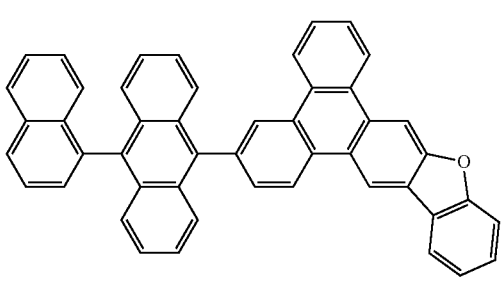

-continued
Compound 63
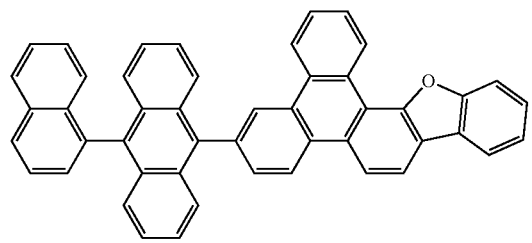
Compound 64
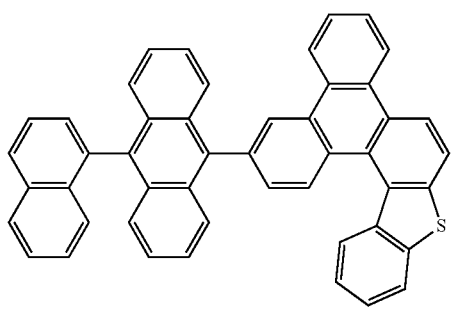
Compound 65
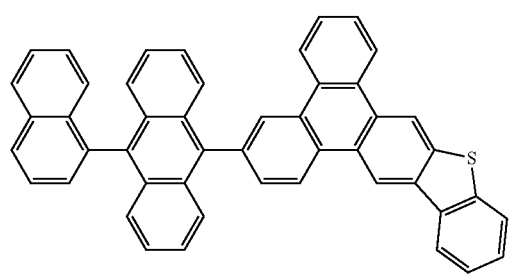
Compound 66
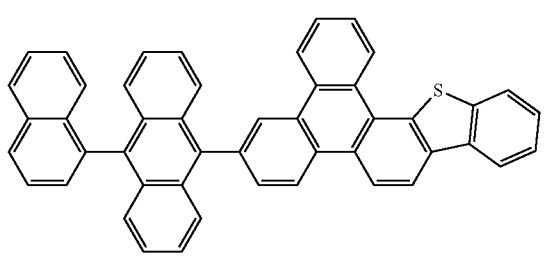
Compound 67
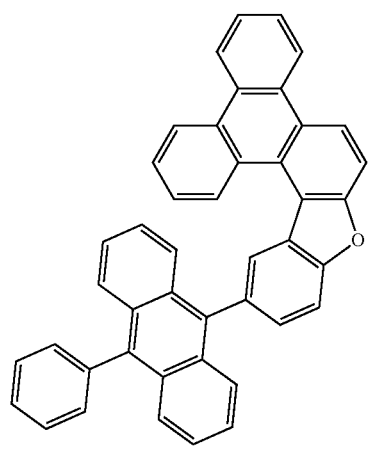
Compound 68
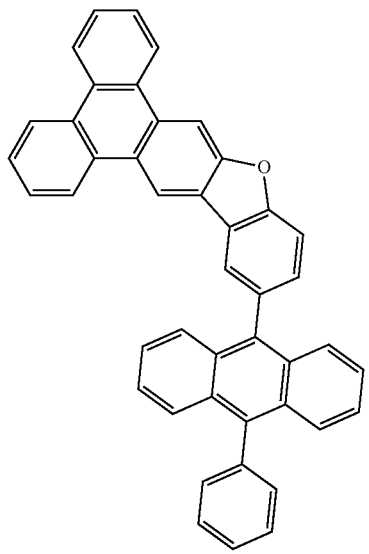

-continued
Compound 69
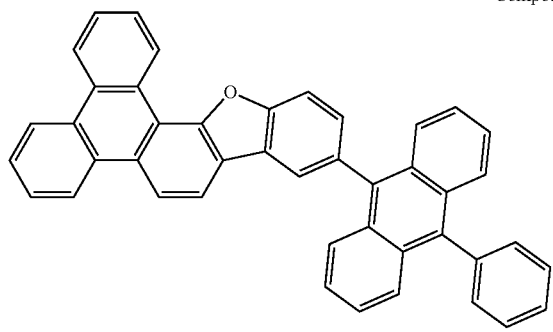
Compound 70
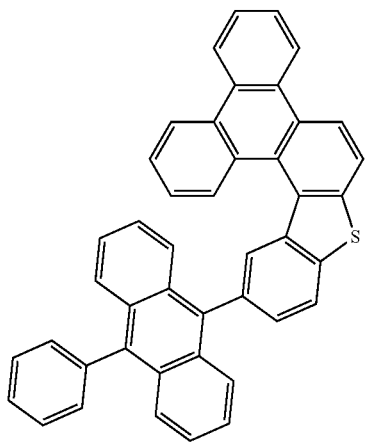
Compound 71
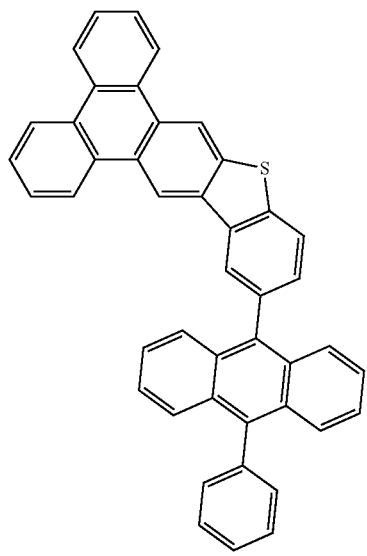
Compound 72
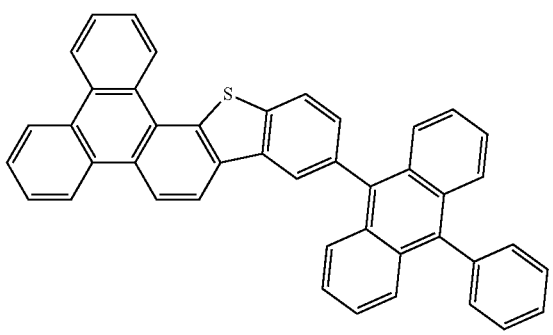

-continued
Compound 73
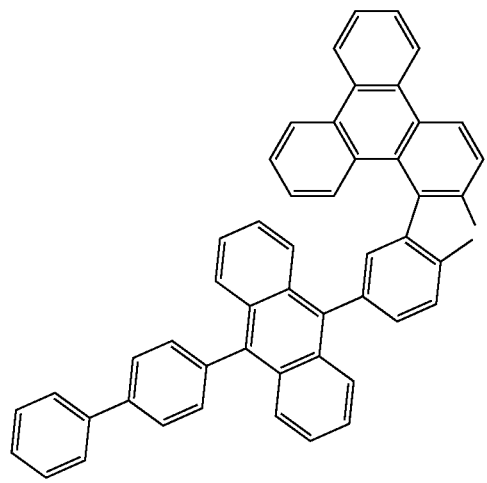
Compound 74
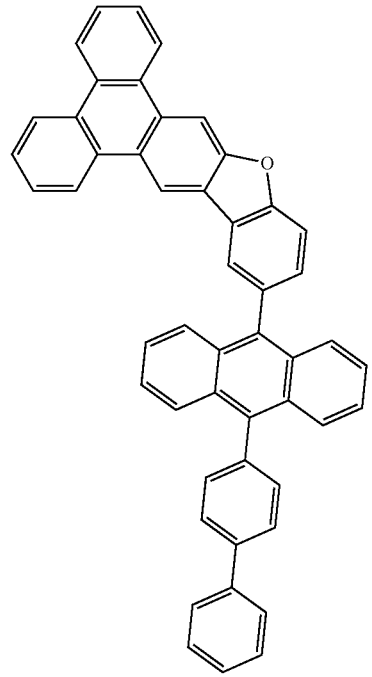
Compound 75
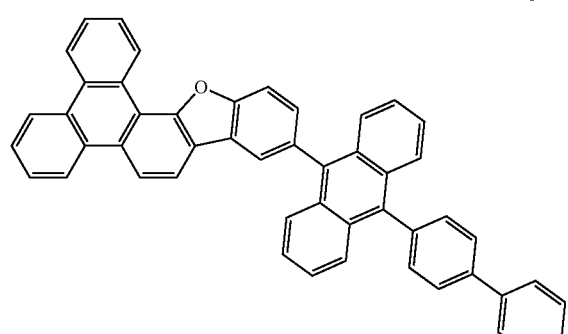
Compound 76
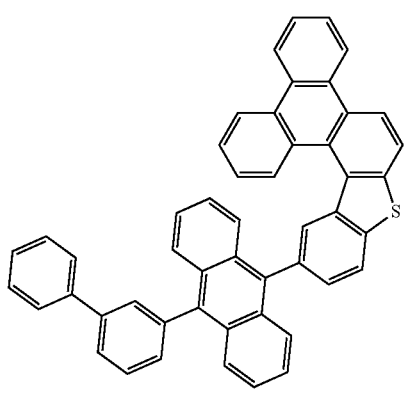

Compound 77
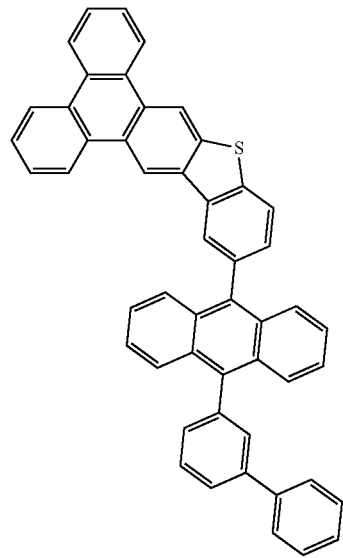
Compound 78
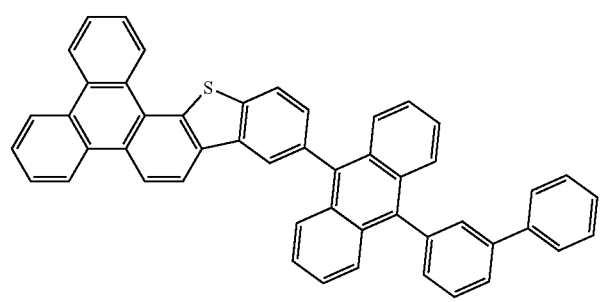
Compound 79
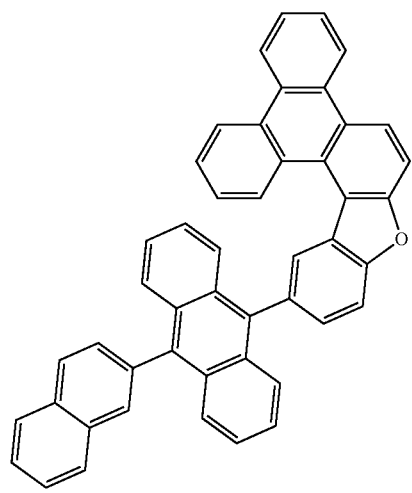
Compound 80
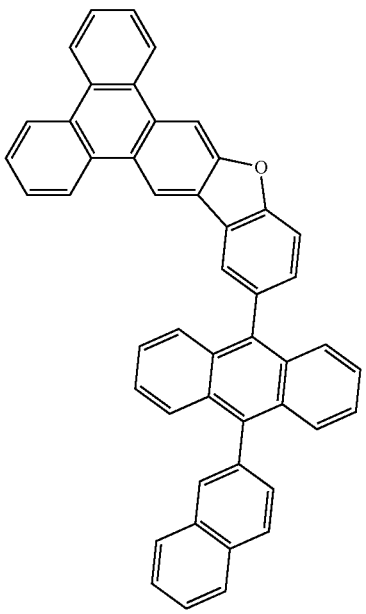

-continued
Compound 81
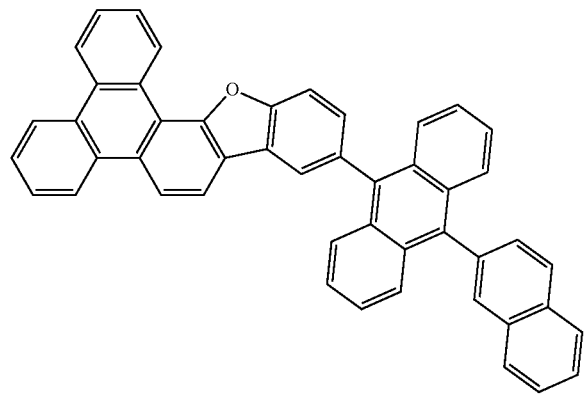
Compound 82
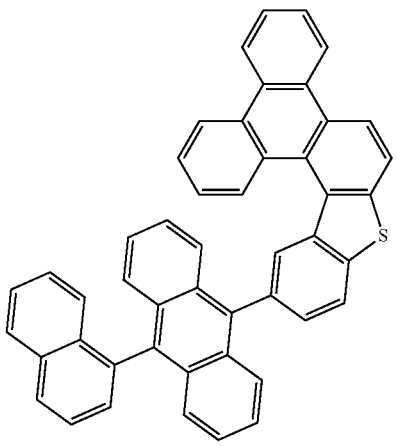
Compound 83
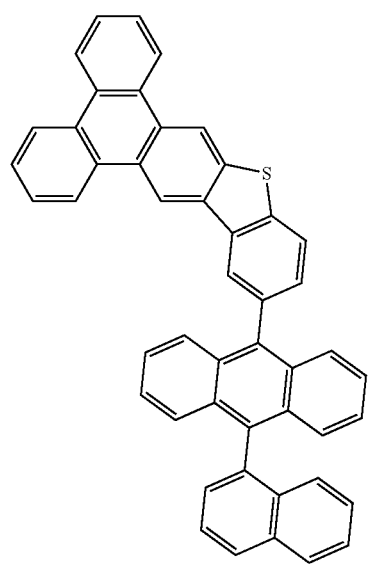
Compound 84
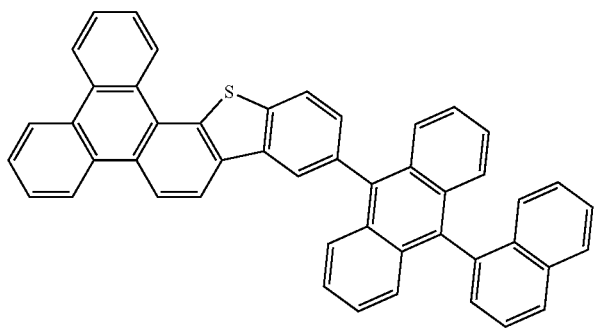
Compound 85
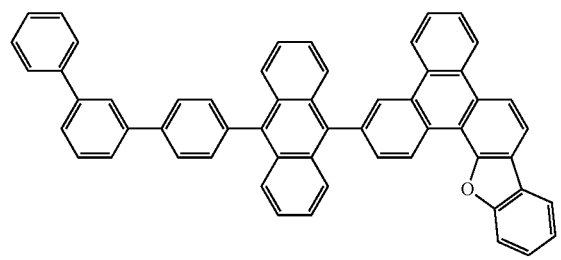
Compound 86
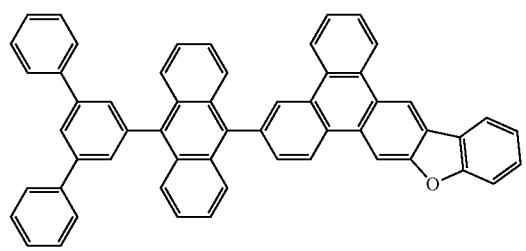 [SMILES: c1ccc(-c2cc(-c3ccccc3)cc(-c3c4ccccc4c(-c4ccc5c(c4)c4ccccc4c4cc6c(cc54)oc4ccccc46)c4ccccc34)c2)cc1]

-continued
Compound 87
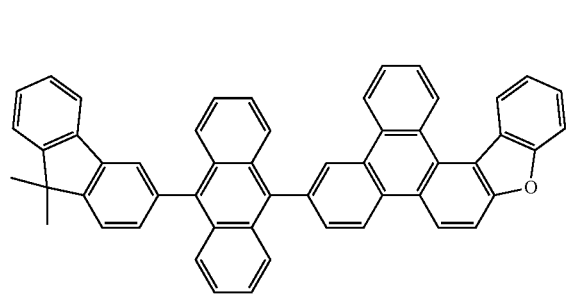 [SMILES: CC1(C)c2ccccc2-c2cc(-c3c4ccccc4c(-c4ccc5c(c4)c4ccccc4c4c5ccc5oc6ccccc6c54)c4ccccc34)ccc21]
Compound 88
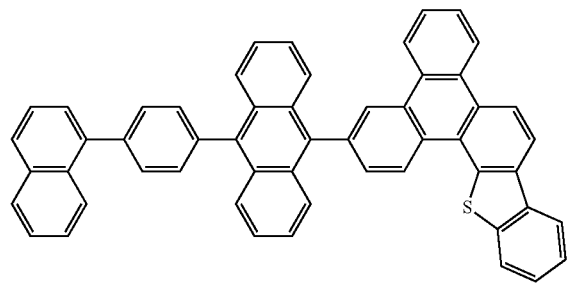
Compound 89
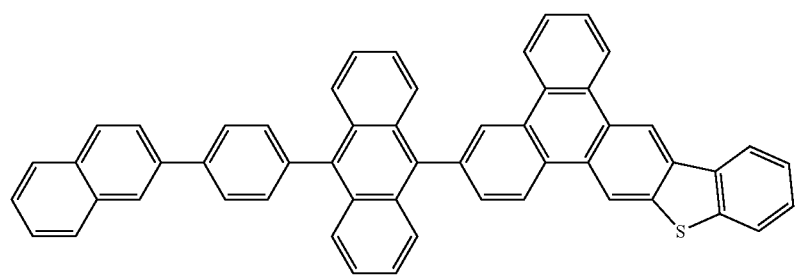
Compound 90
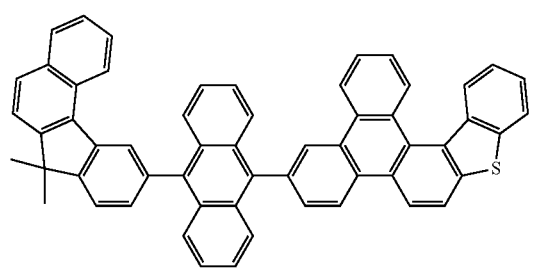
Compound 91
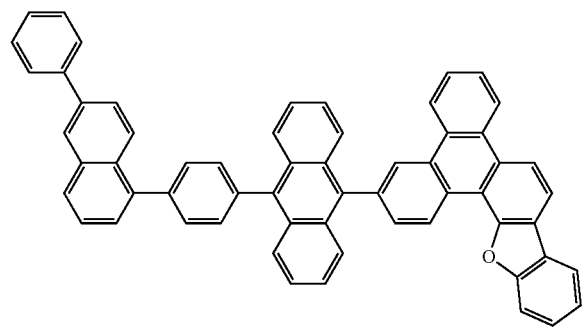
Compound 92
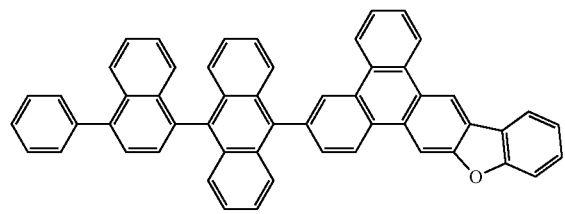
Compound 93
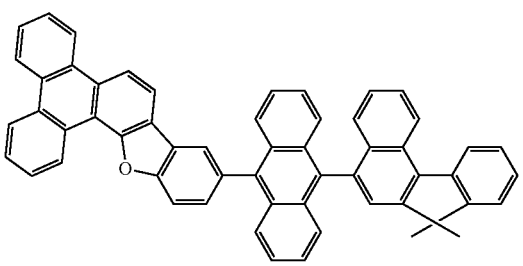
Compound 94
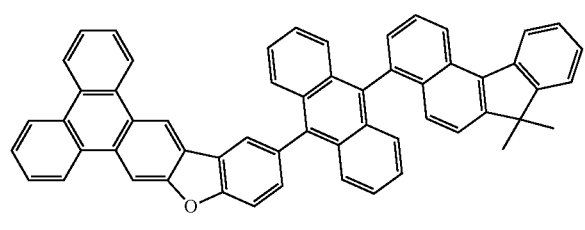
Compound 95
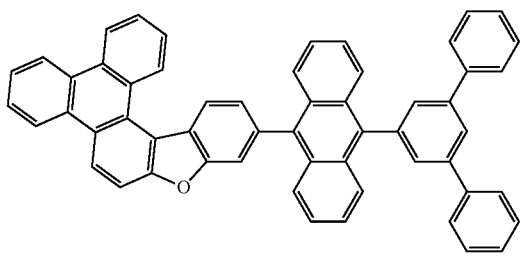

-continued
Compound 96
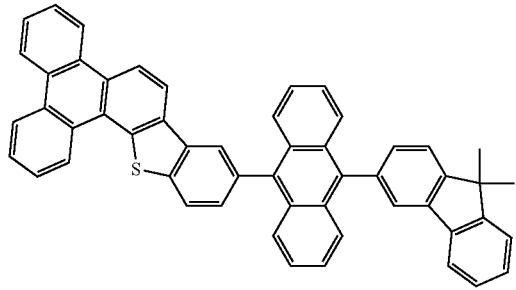
Compound 97
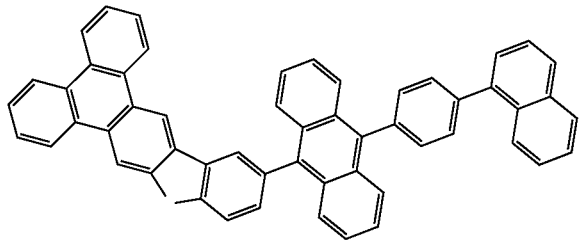
Compound 98
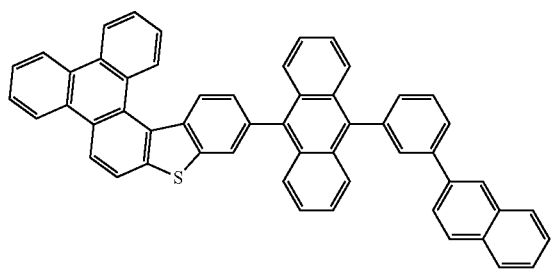
Compound 99
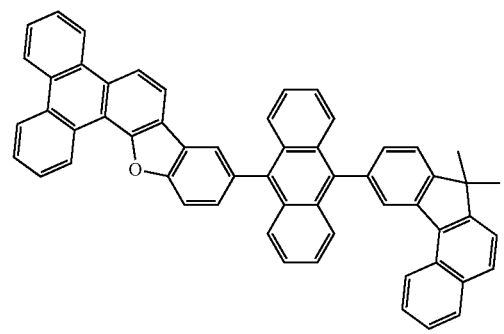
Compound 100
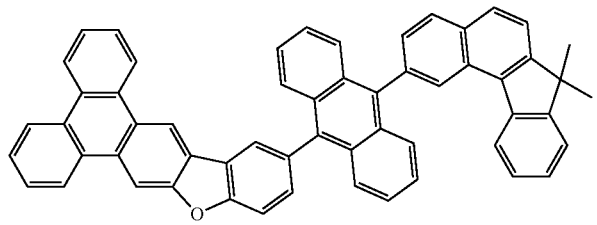
Compound 101
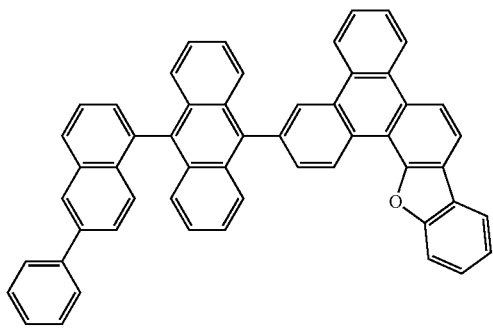
Compound 102
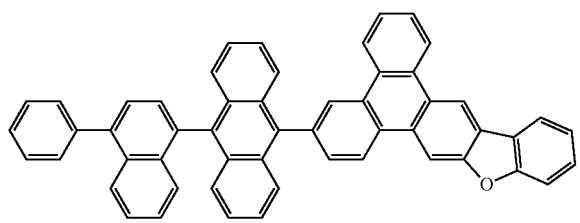
Compound 103
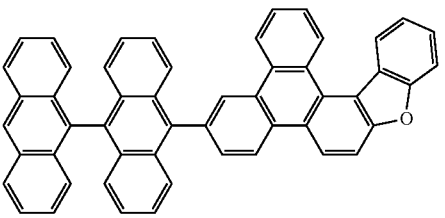
Compound 104
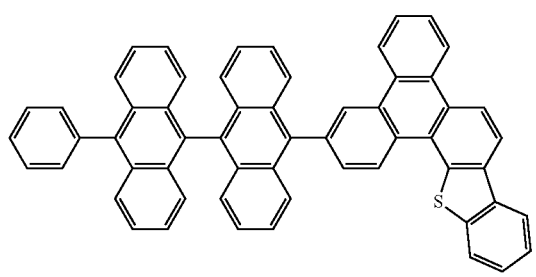
Compound 105
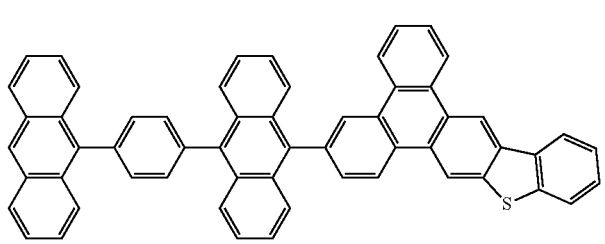

-continued
Compound 106
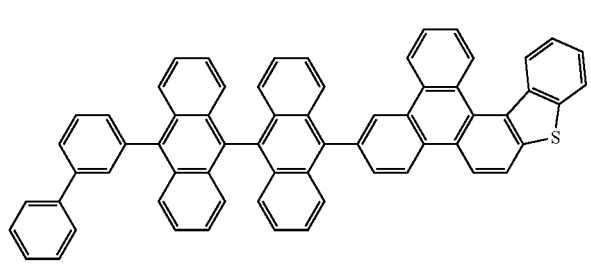
Compound 107
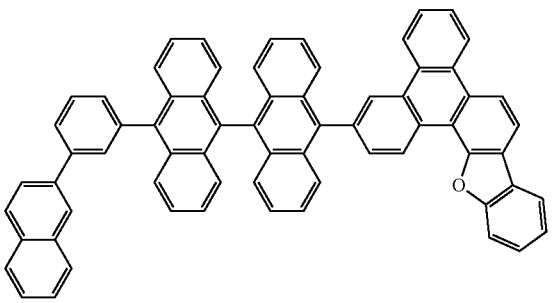
Compound 108
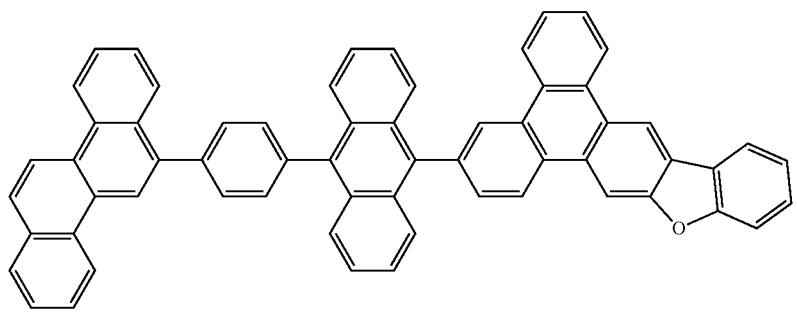
Compound 109
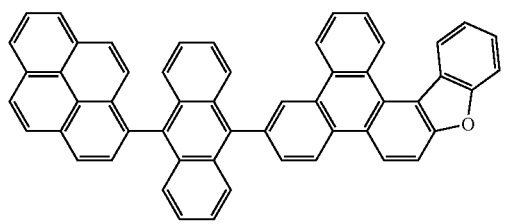 [SMILES: c1cc2ccc3ccc(-c4c5ccccc5c(-c5ccc6c(c5)c5ccccc5c5c6ccc6oc7ccccc7c65)c5ccccc45)c4ccc(c1)c2c34]
Compound 110
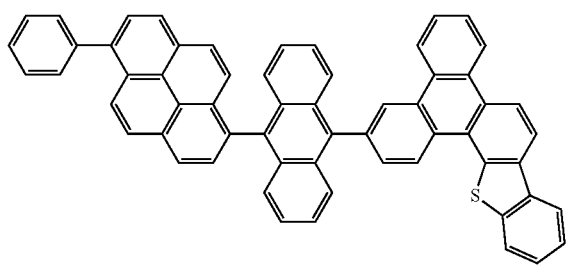
Compound 111
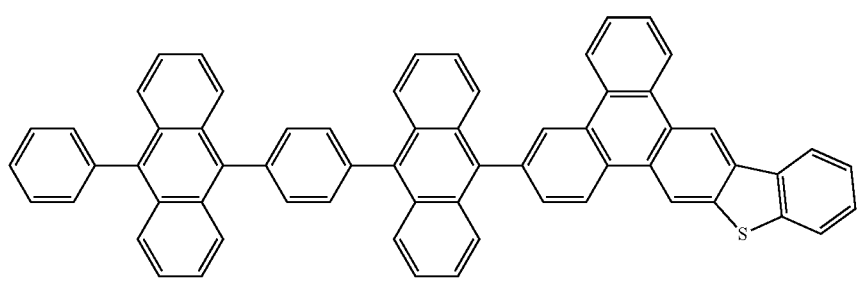
Compound 112
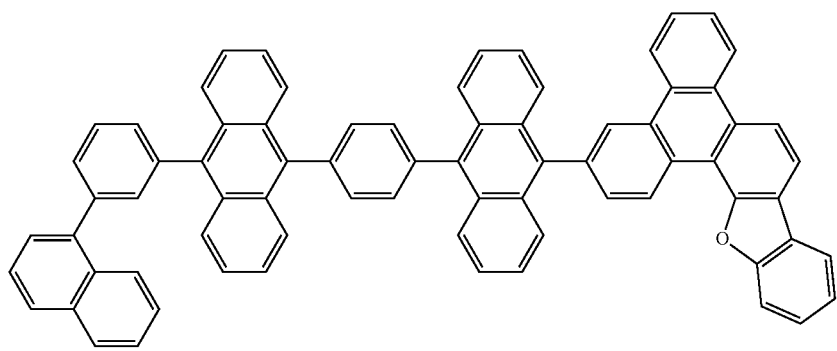

Compound 113
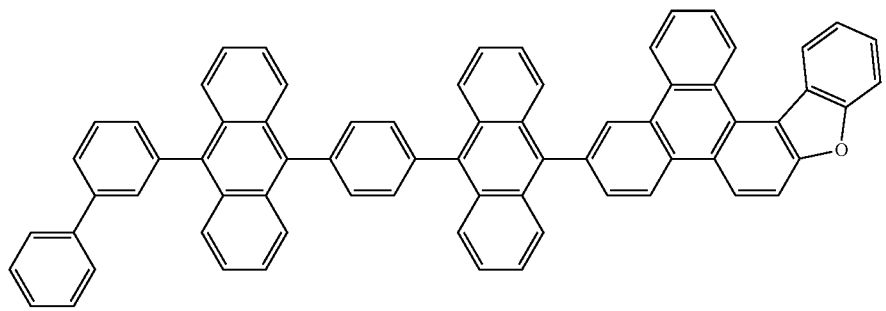
Compound 114
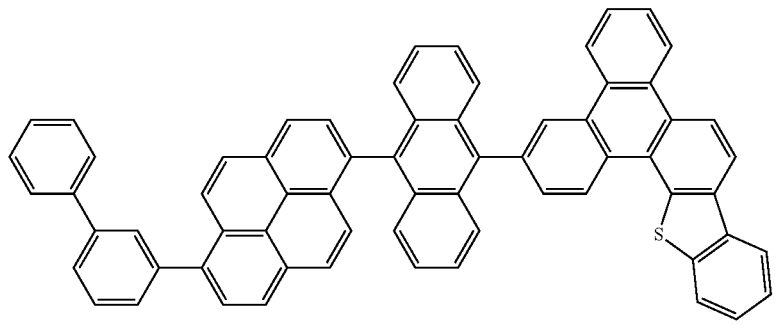
Compound 115
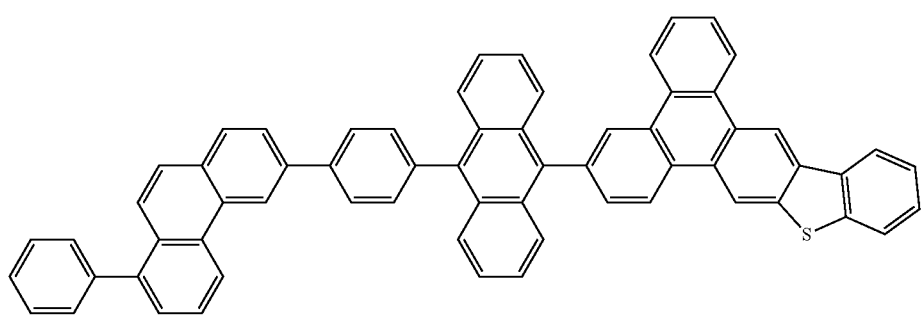
Compound 116          Compound 117
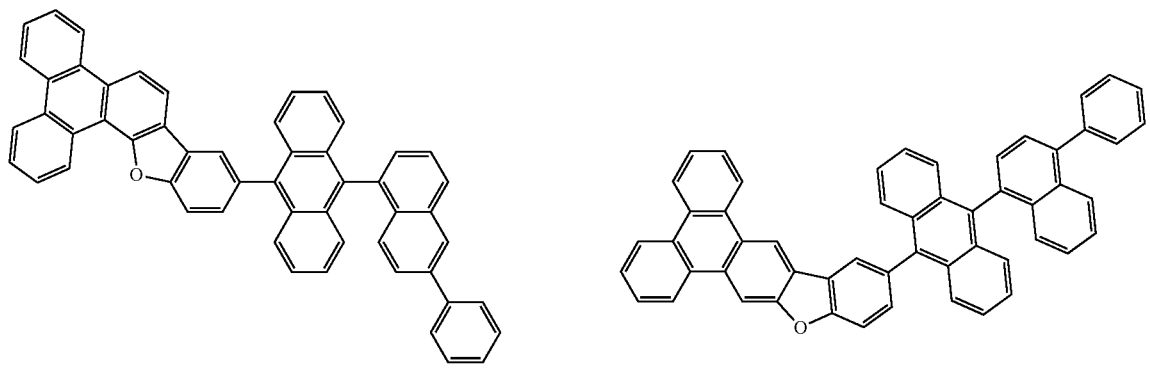
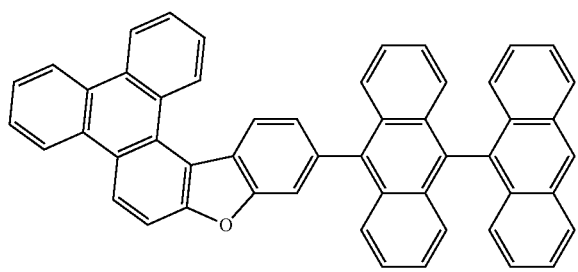

-continued
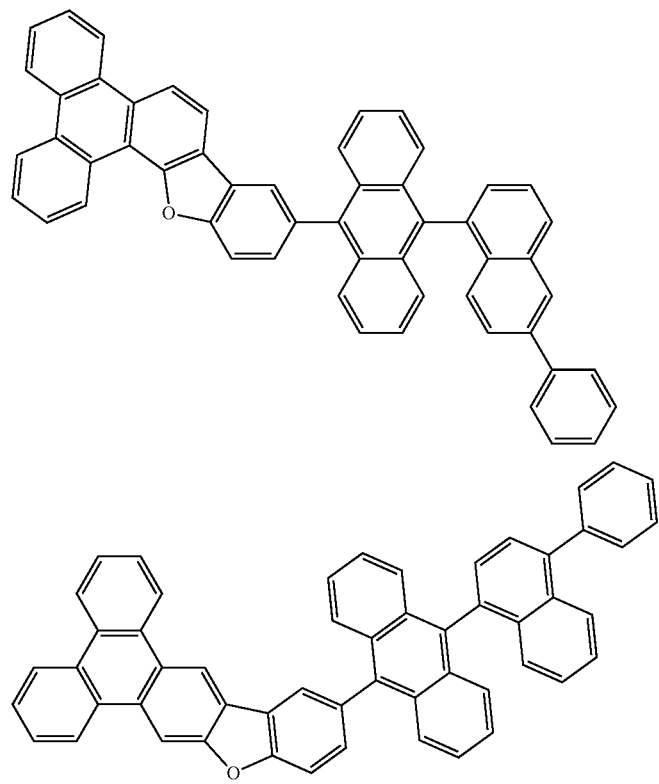
Compound 118
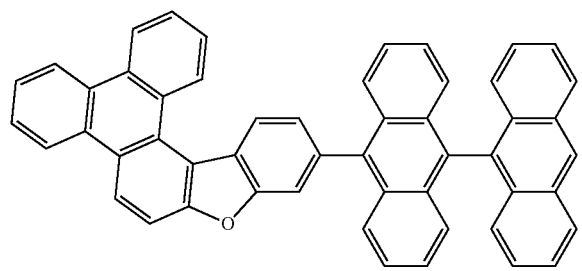
Compound 118
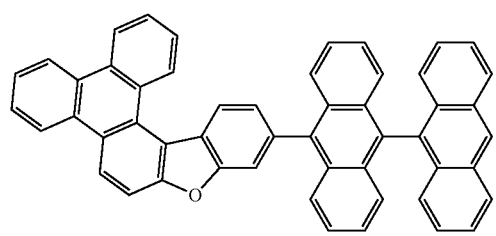
Compound 119
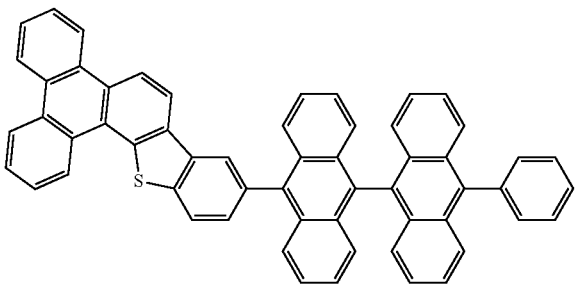

-continued
Compound 120
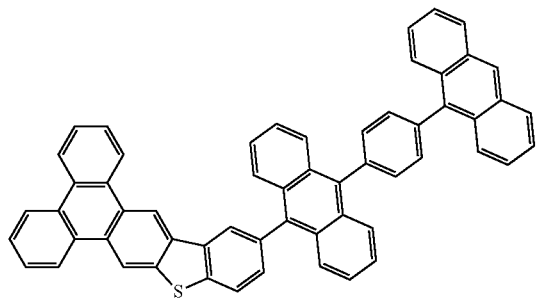
Compound 121
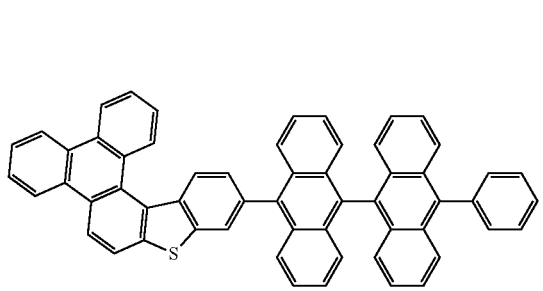
Compound 122
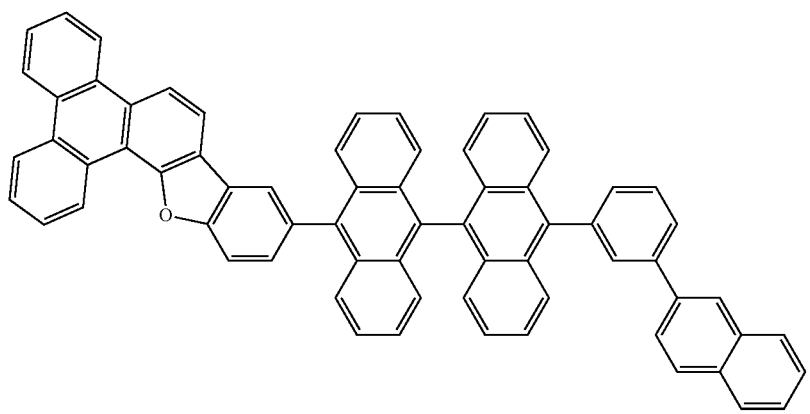
Compound 123
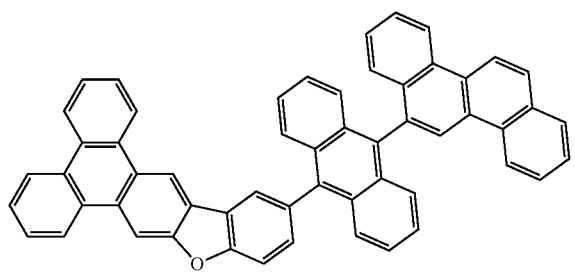
Compound 124
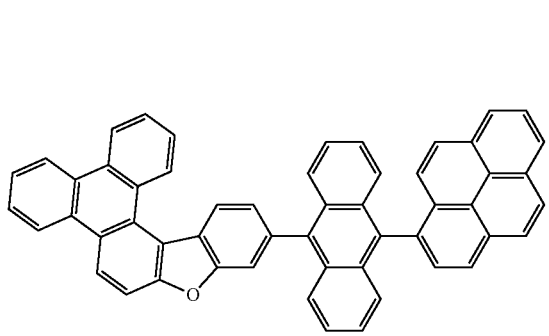
Compound 125
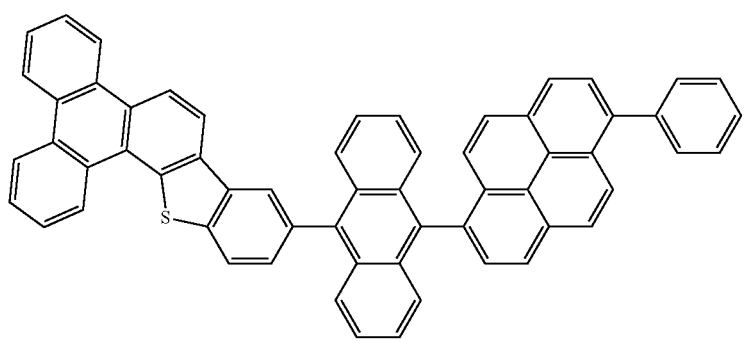

-continued
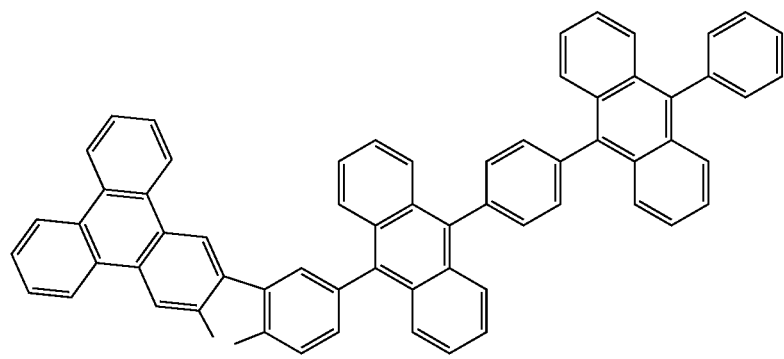
Compound 126
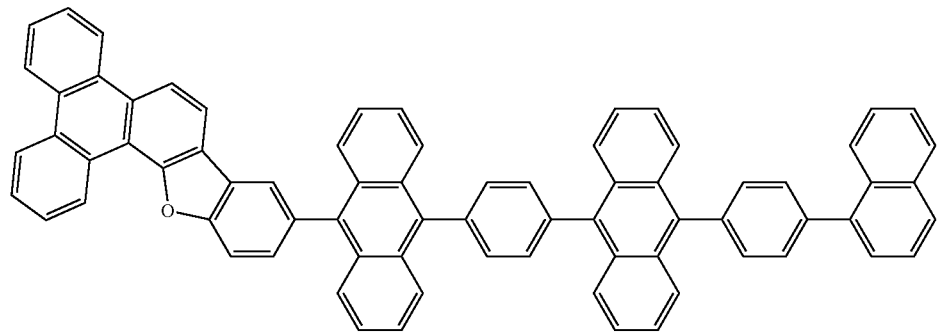
Compound 127
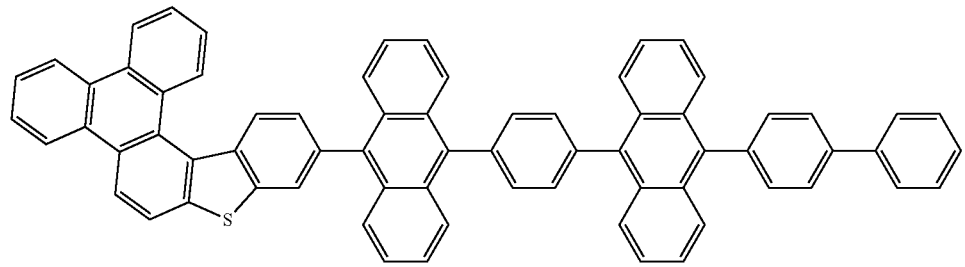
Compound 128
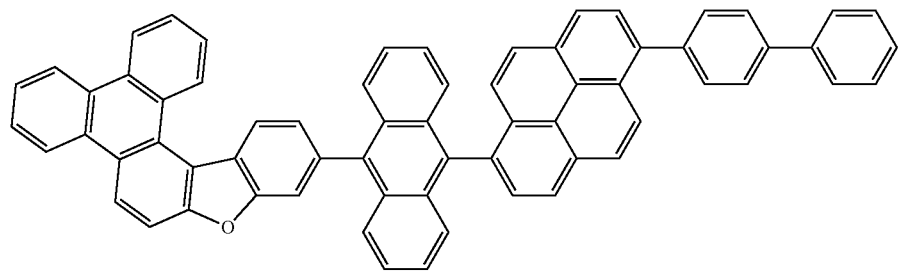
Compound 129
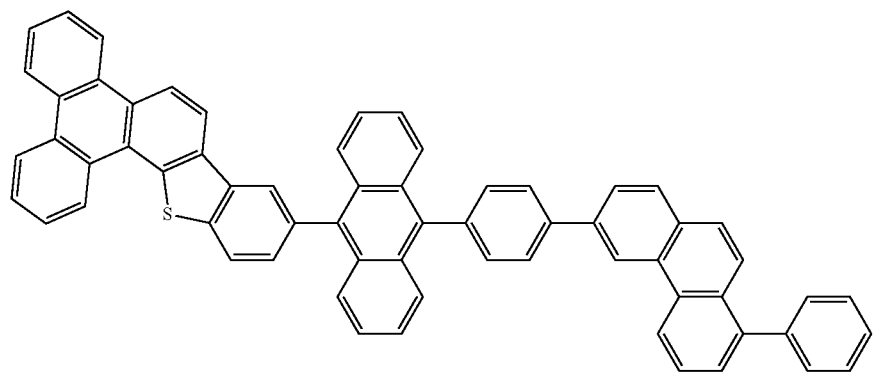
Compound 130

Compound 131
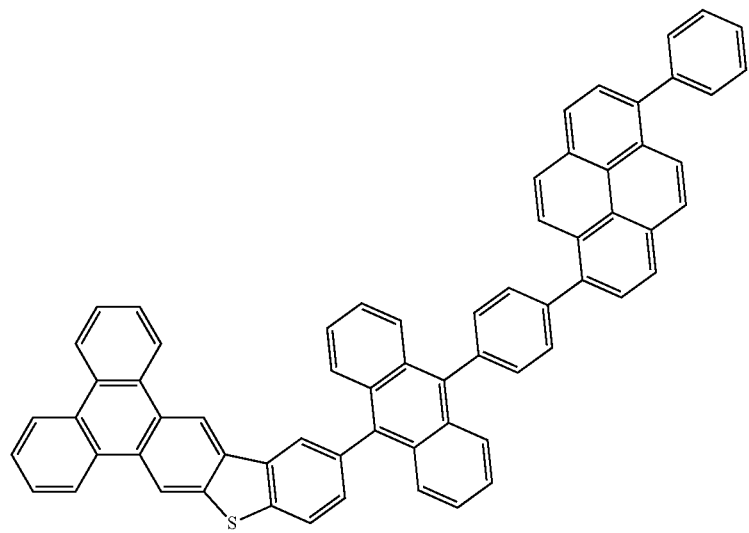
Compound 132
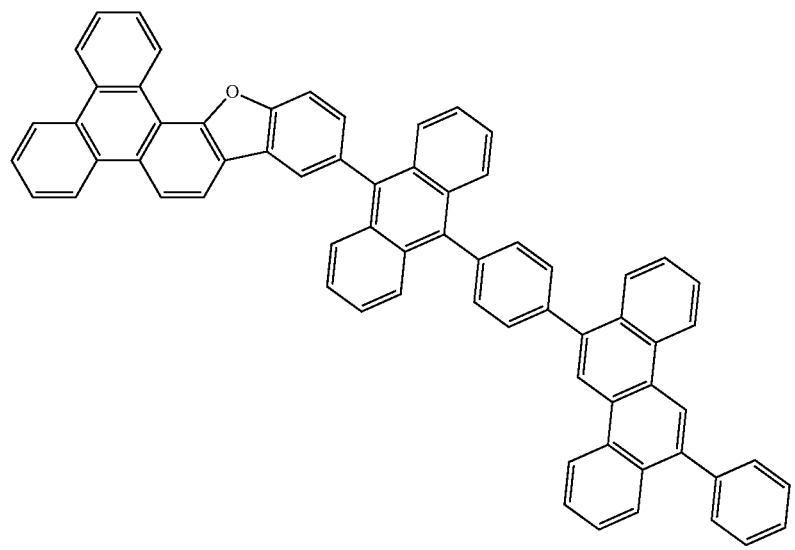
Compound 133
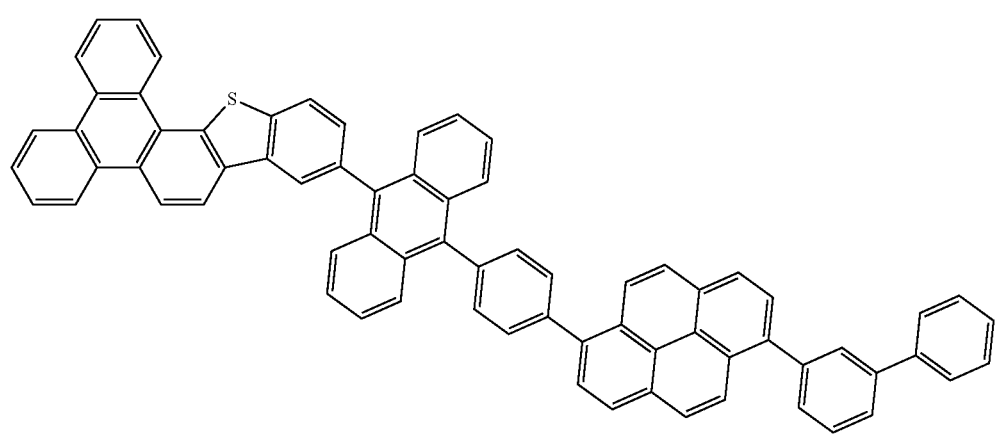

-continued
Compound 134
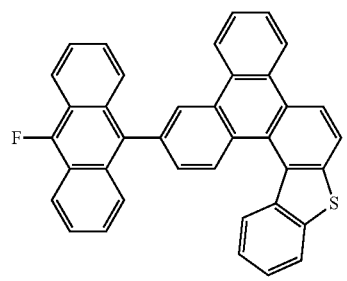 [SMILES: Fc1c2ccccc2c(-c2ccc3c(c2)c2ccccc2c2ccc4sc5ccccc5c4c23)c2ccccc12]
Compound 135
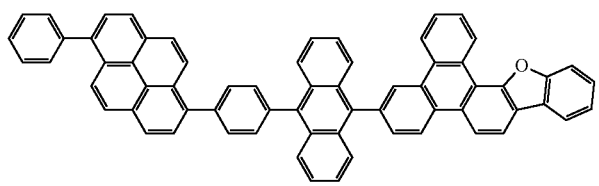 [SMILES: c1ccc(-c2ccc3ccc4c(-c5ccc(-c6c7ccccc7c(-c7ccc8c(c7)c7ccccc7c7c8ccc8c9ccccc9oc87)c7ccccc67)cc5)ccc5ccc2c3c54)cc1]
Compound 136
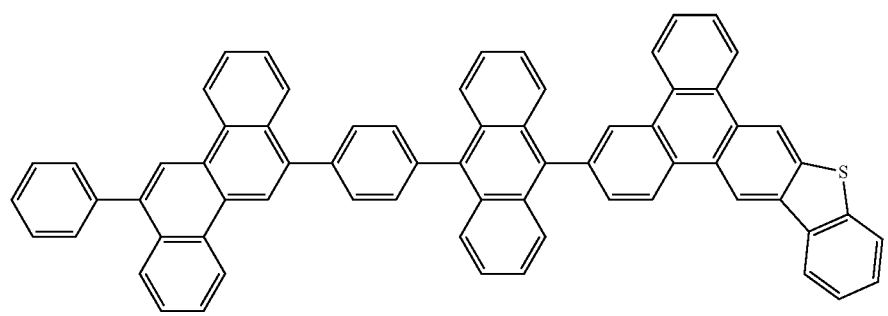
Compound 137
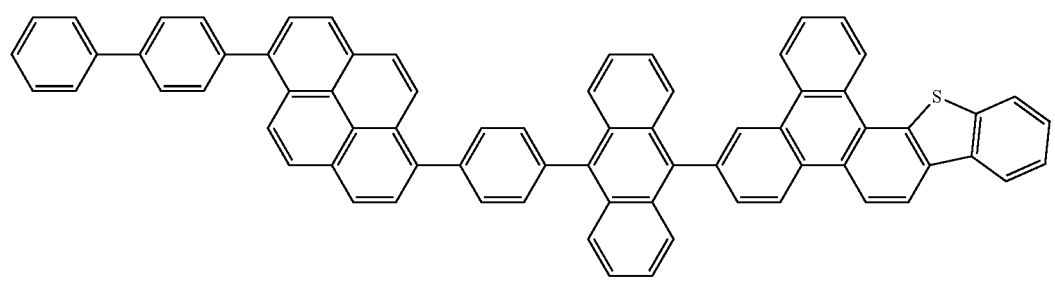
Compound 138
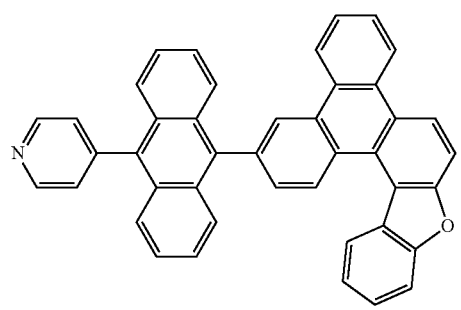 [SMILES: c1ccc2c(c1)oc1ccc3c4ccccc4c4cc(-c5c6ccccc6c(-c6ccncc6)c6ccccc56)ccc4c3c12]
Compound 139
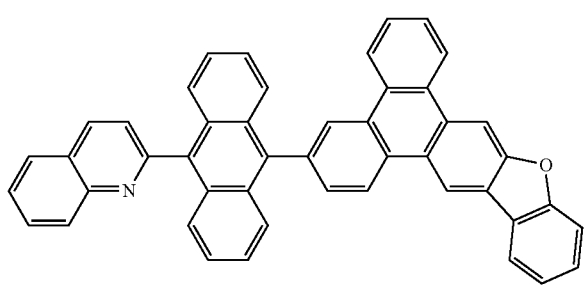
Compound 140
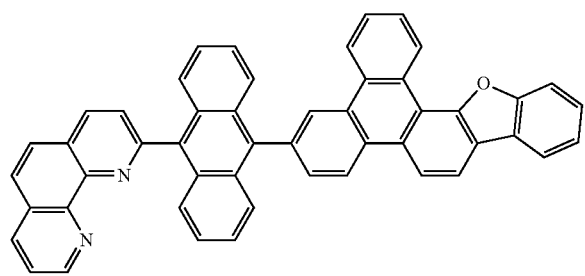
Compound 141
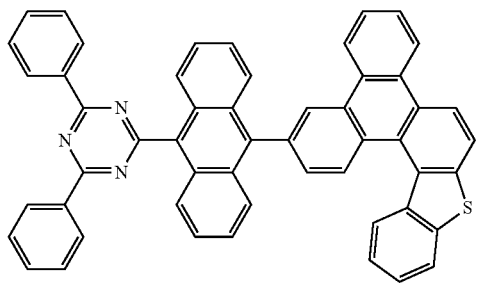 [SMILES: c1ccc(-c2nc(-c3ccccc3)nc(-c3c4ccccc4c(-c4ccc5c(c4)c4ccccc4c4ccc6sc7ccccc7c6c45)c4ccccc34)n2)cc1]

-continued
Compound 142
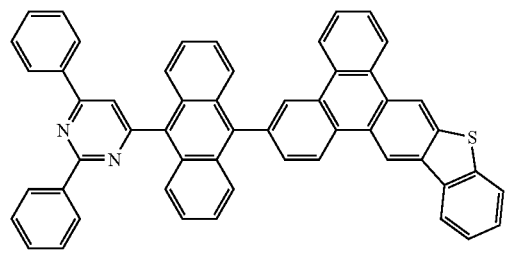
Compound 143
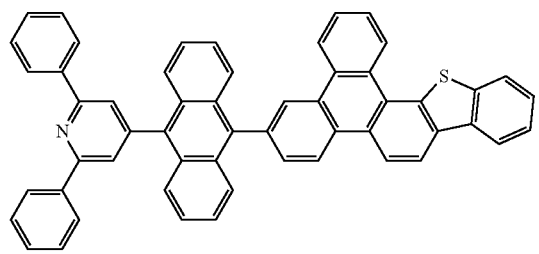
Compound 144
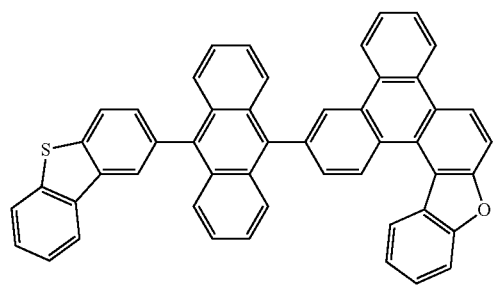 [SMILES: c1ccc2c(c1)oc1ccc3c4ccccc4c4cc(-c5c6ccccc6c(-c6ccc7sc8ccccc8c7c6)c6ccccc56)ccc4c3c12]
Compound 145
Compound 146
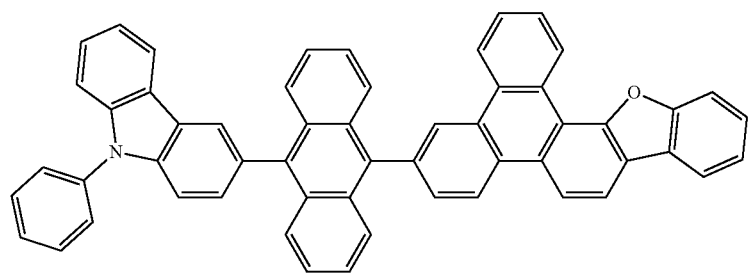
Compound 147
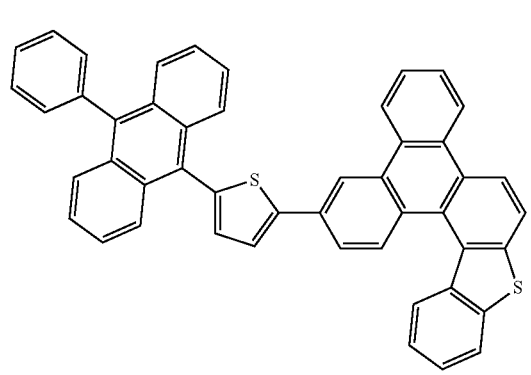
Compound 148
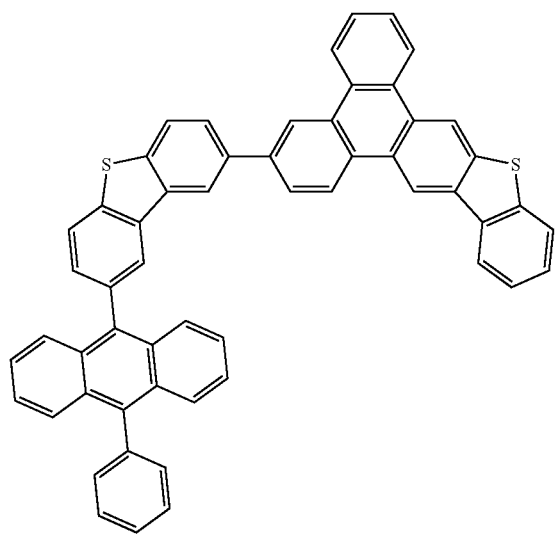

Compound 149
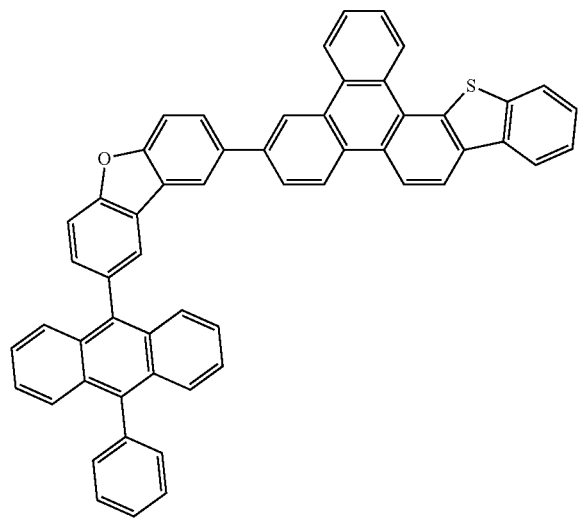 [SMILES: c1ccc(-c2c3ccccc3c(-c3ccc4oc5ccc(-c6ccc7c(c6)c6ccccc6c6c7ccc7c8ccccc8sc76)cc5c4c3)c3ccccc23)cc1]
Compound 150
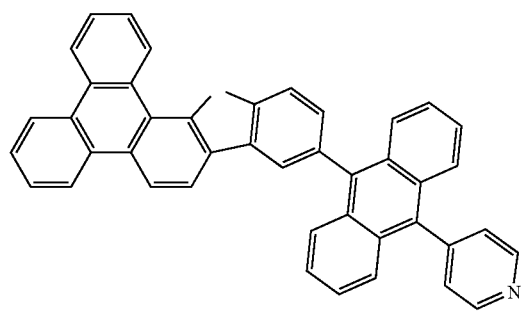
Compound 151
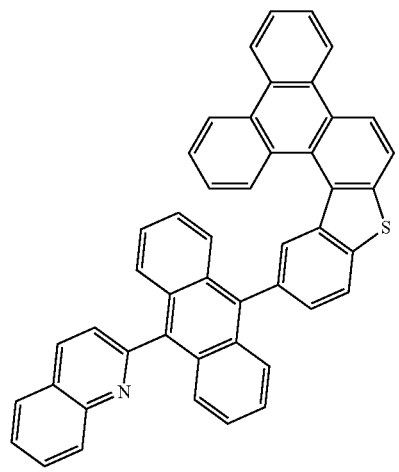
Compound 152
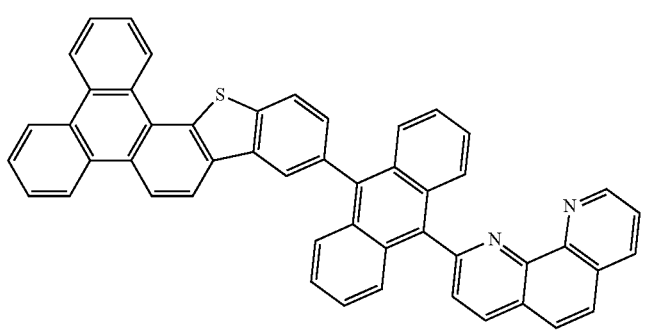

-continued
Compound 153
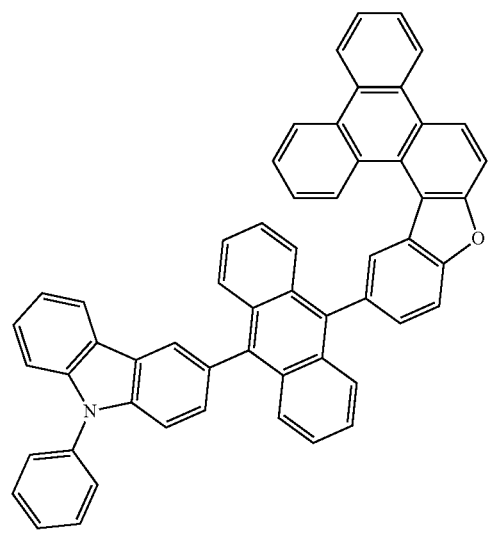
Compound 154
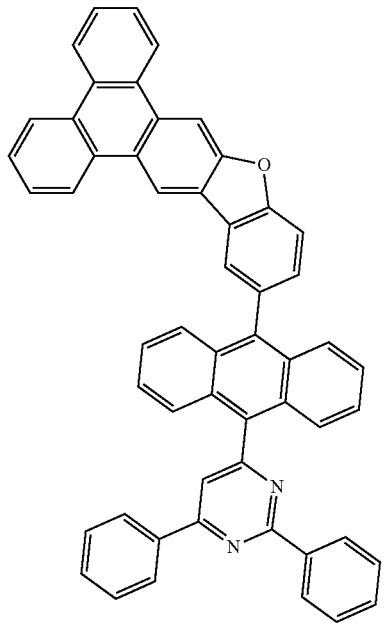
Compound 155
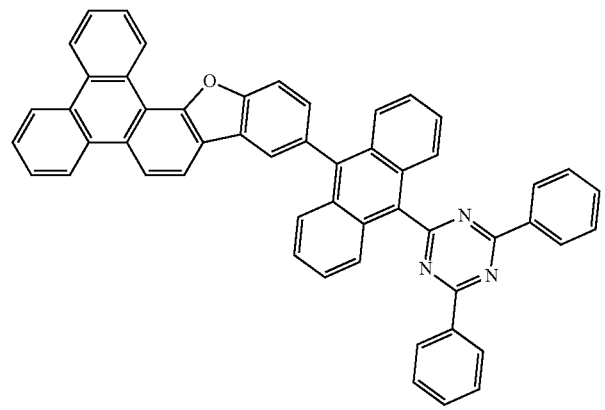
Compound 156
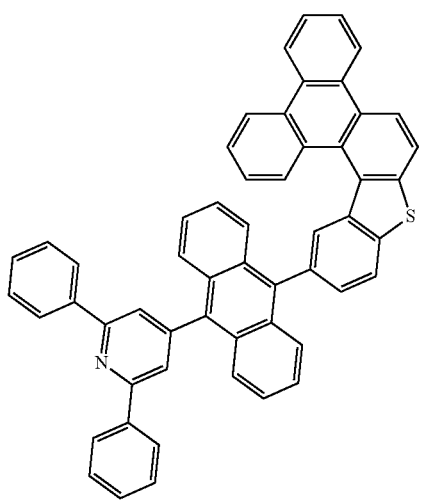

-continued
Compound 157
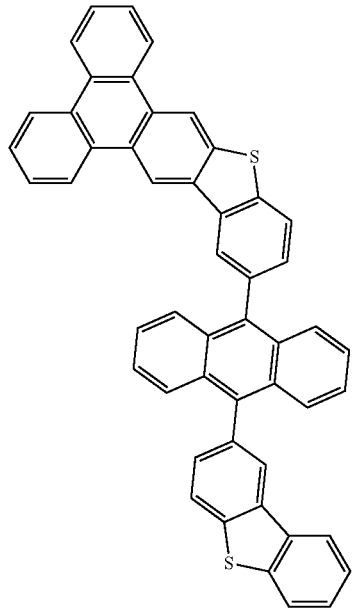
Compound 158
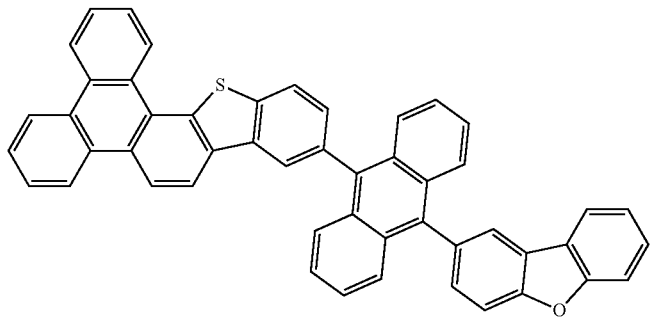
Compound 159
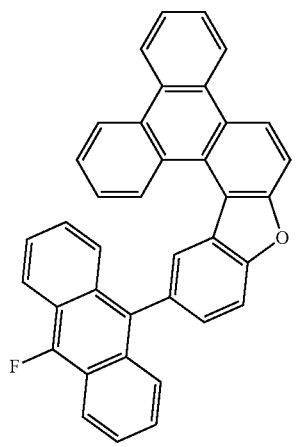
Compound 160
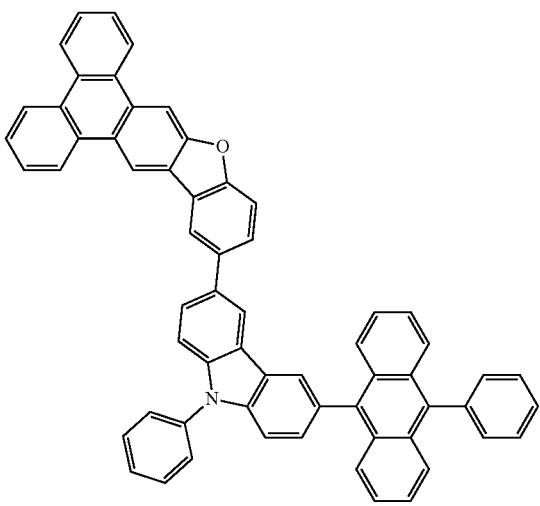
Compound 161
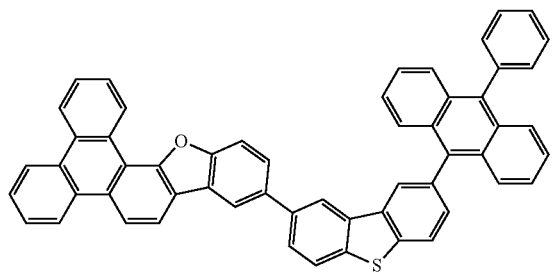
Compound 162
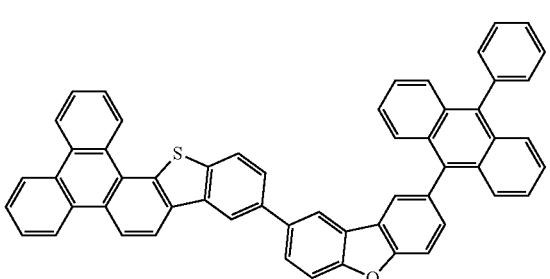

-continued
Compound 163
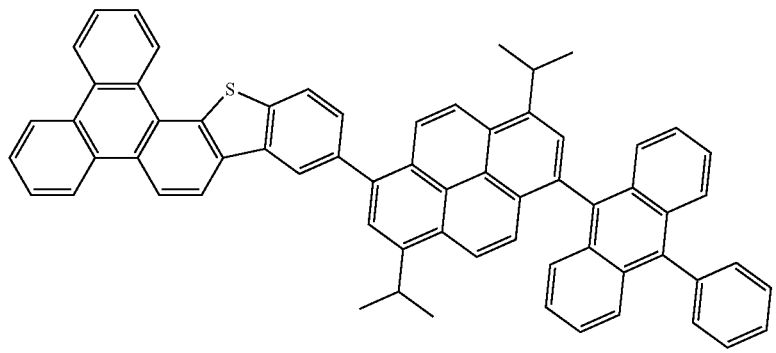
Compound 165
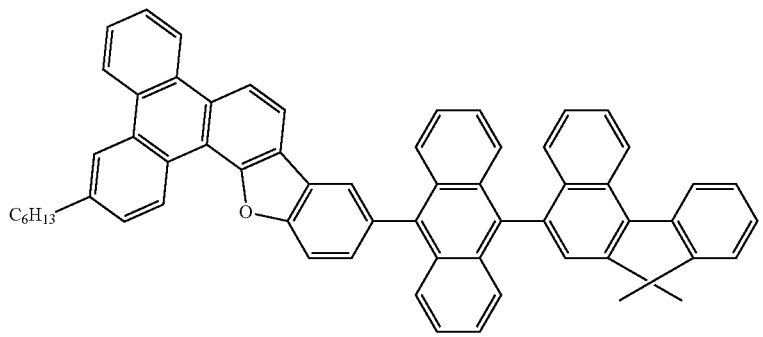
Compound 166
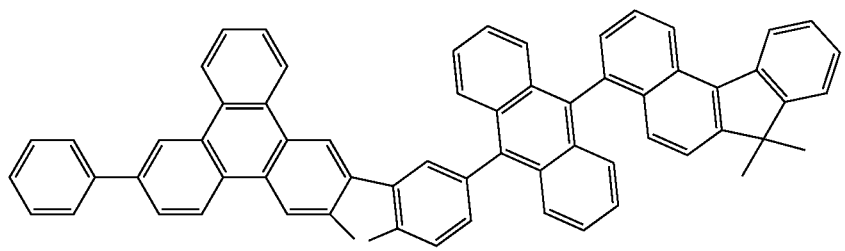
Compound 167
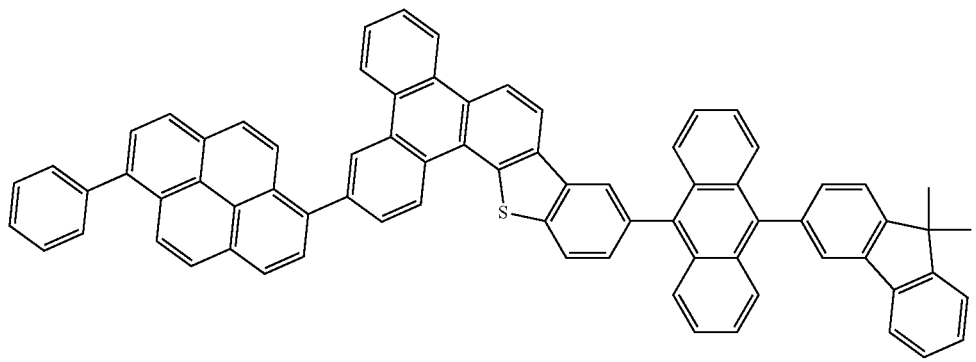
Compound 168
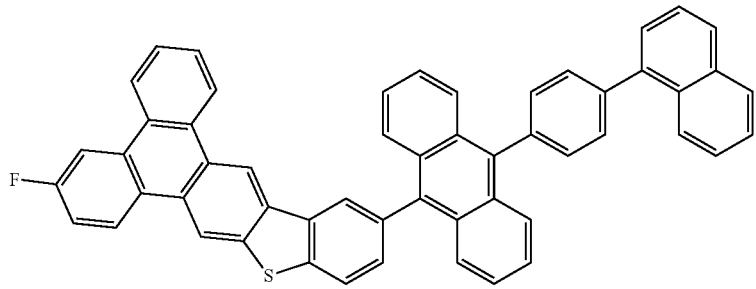

-continued
Compound 169
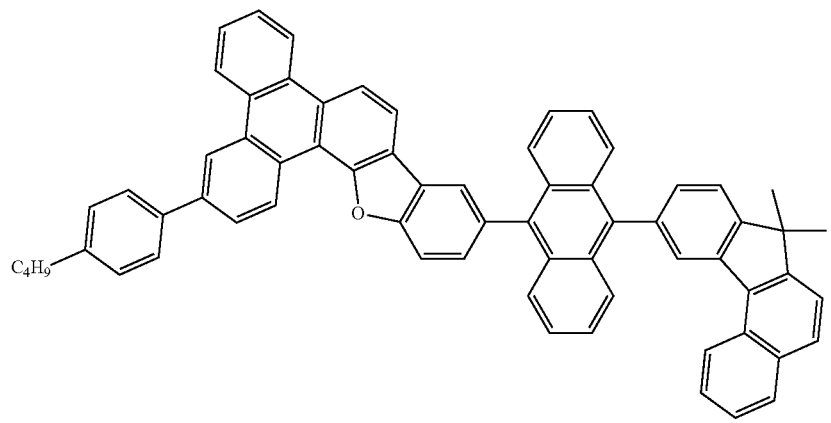
Compound 170
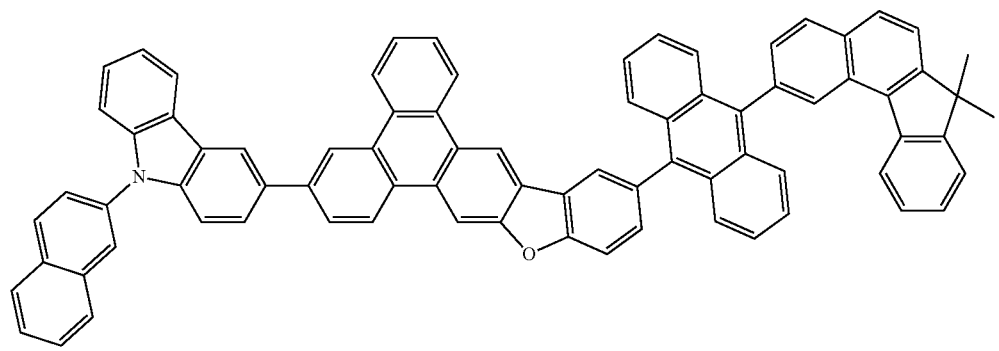
Compound 171
Compound 172
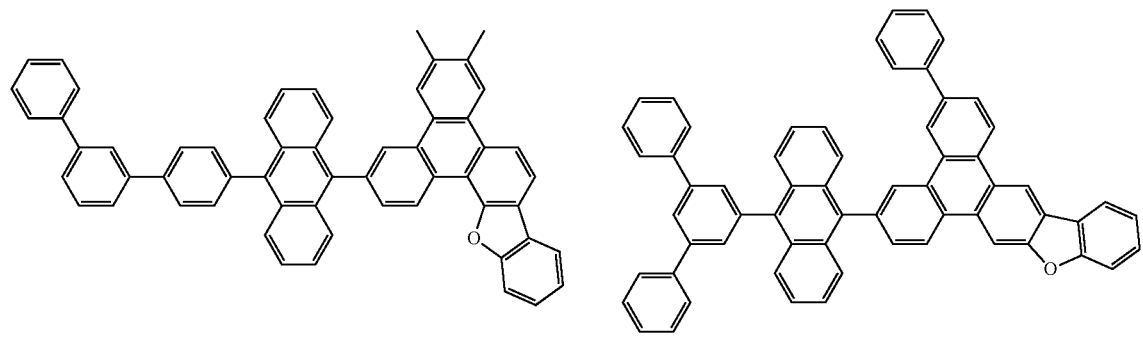
Compound 173
Compound 174
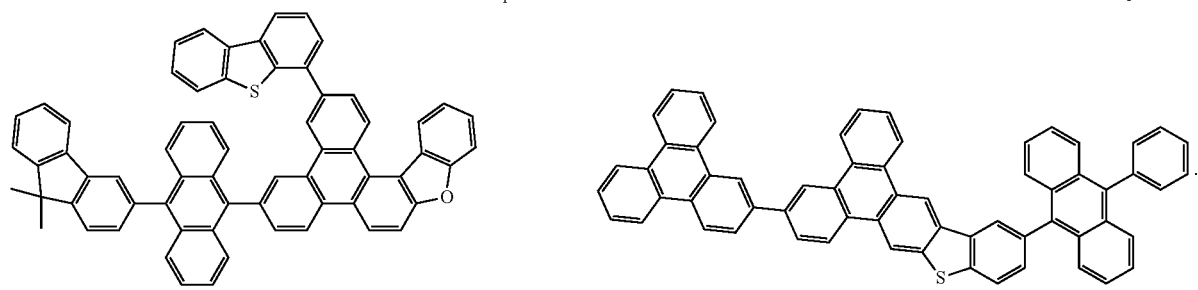

7. An organic electroluminescence device, comprising a pair of electrodes composed of a cathode and an anode, and a light emitting layer between the pair of electrodes, wherein the light emitting layer comprises the organic compound of claim 6.

8. The organic electroluminescence device according to claim 7, wherein the light emitting layer comprising the organic compound is a host material.

9. The organic electroluminescence device according to claim 7, wherein the organic electroluminescence device is a lighting panel.

10. The organic electroluminescence device according to claim 7, wherein the organic electroluminescence device is a backlight panel.

* * * * *